United States Patent
Breslow et al.

(10) Patent No.: US 6,511,990 B1
(45) Date of Patent: Jan. 28, 2003

(54) CLASS OF CYTODIFFERENTIATING AGENTS AND HISTONE DEACETYLASE INHIBITORS, AND METHODS OF USE THEREOF

(75) Inventors: Ronald Breslow, Englewood, NJ (US); Sandro Belvedere, New York, NY (US); Leland Gershell, New York, NY (US); Thomas A. Miller, New York, NY (US); Paul A. Marks, Washington, CT (US); Victoria M. Richon, New York, NY (US); Richard A. Rifkind, New York, NY (US)

(73) Assignees: Sloan-Kettering Institute for Cancer Research, New York, NY (US); The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/645,430

(22) Filed: Aug. 24, 2000

Related U.S. Application Data
(60) Provisional application No. 60/208,688, filed on Jun. 1, 2000, and provisional application No. 60/152,755, filed on Sep. 8, 1999.

(51) Int. Cl.[7] ................ A61K 31/4709; A61K 31/167; C07D 215/40; C07D 401/12; C07C 259/04; A61P 35/00

(52) U.S. Cl. ............... 514/314; 514/249; 514/261; 514/266; 514/307; 514/309; 514/311; 514/316; 514/318; 514/354; 514/355; 514/575; 544/277; 544/258; 546/171; 546/141; 546/146; 546/314; 546/316; 562/623; 562/622

(58) Field of Search ................ 546/171, 316, 546/314, 141, 146; 544/277, 258; 562/623, 622; 514/575, 355, 354, 311, 307, 309, 261, 266, 249, 316, 318, 314

(56) References Cited

U.S. PATENT DOCUMENTS

| | | | |
|---|---|---|---|
| 2,279,560 A | 4/1942 | Dietrich | 252/47 |
| 2,346,665 A | 4/1944 | Cupery | 260/500 |
| 2,895,991 A | 7/1959 | Randall et al. | 260/558 |
| 3,450,673 A | 6/1969 | McKillip | 260/75 |
| 3,632,783 A | 1/1972 | Stonis | 424/320 |
| 3,875,301 A | 4/1975 | Windheuser | 424/45 |
| 4,056,524 A | 11/1977 | Walker | 260/239 BF |
| 4,442,305 A | 4/1984 | Weitl et al. | 562/451 |
| 4,480,125 A | 10/1984 | Haas et al. | 564/144 |
| 4,537,781 A | 8/1985 | Darling | 514/616 |
| 4,611,053 A | 9/1986 | Sasa | 528/335 |
| 4,614,815 A | 9/1986 | Cognigni et al. | 560/88 |
| 4,801,748 A | 1/1989 | Murahashi et al. | 564/126 |
| 4,863,967 A | 9/1989 | Hall et al. | 514/615 |
| 4,882,346 A | 11/1989 | Driscoll et al. | 514/389 |
| 4,935,450 A | 6/1990 | Cone, Jr. | 514/728 |
| 4,983,636 A | 1/1991 | Takeuchi et al. | 514/699 |
| 5,055,608 A | 10/1991 | Marks et al. | 560/169 |
| 5,175,191 A | 12/1992 | Marks et al. | 514/575 |
| 5,330,744 A | 7/1994 | Pontremoli et al. | 424/10 |
| 5,366,982 A | 11/1994 | Dereu et al. | 514/340 |
| 5,668,179 A | 9/1997 | Breslow et al. | 514/629 |
| 5,773,474 A | 6/1998 | Breslow et al. | 514/616 |
| 5,846,960 A | 12/1998 | Labrie | 514/169 |
| 5,932,616 A * | 8/1999 | Breslow | 514/532 |

OTHER PUBLICATIONS

Sof'ina et al. Experimental evaluation of antitumor drugs in the USA and USSR and clinical correlations. Nationa Cancer Institute Monograph 55. Dec. 1980. NIH Publication No. 80–1933. pp. 76–78.*

Das, M.K., et al., "Synthesis of Some Dihydroxamic Acid Siderophores," *Chemical Abstracts*, 101(7):582 (1984). (From *J. Chem. Eng. Data*, 1984, 29(3):345–348, Abstract No. 54665t).

Chun, H.G., et al., "Hexamethylene Bisacetamide: A Polar–Planar Compound Entering Clinical Trials as a Differentiating Agent," *Cancer Treatment Reports*, 70(8):991–996 (1986).

Brown, D., et al., "A Facile Synthesis of Aliphatic Dihydroxamic Acids of General Formula $RONR^1$–CO–$(CH_2)_n$–CO–$NR^1OR$," 23–*Aliphatics*, 105:605 (1986). From *Synth. Commun.*, 1985, 15(13):1159–1164, Abstract No. 78501v).

(List continued on next page.)

*Primary Examiner*—Evelyn Mei Huang
(74) *Attorney, Agent, or Firm*—Hamilton, Brook, Smith & Reynolds, P.C.

(57) ABSTRACT

The present invention provides the compound having the formula:

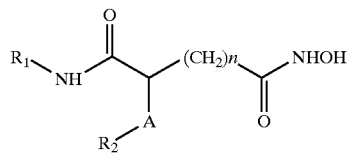

wherein each of $R_1$ and $R_2$ is, substituted or unsubstituted, aryl, cycloalkyl, cycloalkylamino, naphtha, pyridineamino, piperidino, t-butyl, aryloxy, arylalkyloxy, or pyridine group; wherein A is an amido moiety, —O—, —S—, —NH—, or —$CH_2$—; and wherein n is an integer from 3 to 8. The present invention also provides a method of selectively inducing growth arrest, terminal differentiation and/or apoptosis of neoplastic cells and thereby inhibiting proliferation of such cells. Moreover, the present invention provides a method of treating a patient having a tumor characterized by proliferation of neoplastic cells. Lastly, the present invention provides a pharmaceutical composition comprising a pharmaceutically acceptable carrier and a therapeutically acceptable amount of the compound above.

35 Claims, 16 Drawing Sheets

OTHER PUBLICATIONS

Brown, D.A., et al., "Design of Metal Chelates with Biological Activity. 5. Complexation Behavior of Dihydroxamic Acids with Metal Ions," *Inorganic Chemistry*, 25(21):3792–3796 (1986).

Linfield, W.M., et al., "Antibacterially Active Substituted Anilides of Carboxylic and Sulfonic Acids," *J. Med. Chem.*, 26(12):1741–1746 (1983).

Lea, M.A., and Tulsyan, N., "Discordant Effects of Butyrate Analogues on Erythroleukemia Cell Proliferation, Differentiation and Histone Deacetylase," *Anticancer Research*, 15:879–883 (1995).

Kwon, H.J., et al., "Depudecin Induces Morphological Reversion of Transformed Fibroblasts via the Inhibition of Histone Deacetylase," *Proc. Natl. Acad. Sci. USA*, 95(7):3356–3361 (1998).

Kim, Y.B., et al., "Oxamflatin is a Novel Antitumor Compound that Inhibits Mammalian Histone Deacetylase," *Oncogene*, 18:2461–2470 (1999).

Kijima, M., et al., "Trapoxin, an Antitumor Cyclic Tetrapeptide, Is an Irreversible Inhibitor of Mammalian Histone Deacetylase," *The Journal of Biological Chemistry*, 268(30):22429–22435 (1993).

Iwata, S., and Hirai, K., "Polyurethanes with Small Permanent Compressive Strain and Their Moldings," *Chemical Abstracts*, 125(18):28. (From Jpn. Kokai Tokkyo Koho JP 08,176,264 [96,176,263], 1996, Abstract No. 222822h.).

Hynes, J.B., "Hydroxylamine Derivatives as Potential Antimalarial Agents. 1. Hydroxamic Acids," *Jour. of Medicinal Chem.*, 13(6):1235–1237 (1970).

Hozumi, T., et al., "Induction of Erythroid Differentiation in Murine Erythroleukemia Cells by N–Substituted Polymethylene Diamides," *Int. J. Cancer*, 23:119–122 (1979).

Hozumi, T., et al., "Induction of Erythroid Differentiation in Murine Erythroleukemia Cells by Nitrogen Substituted Polymethylene Diamides," *Chemical Abstracts*, 90(13). (From *Int. J. Cancer*, 23(1):119–122, 1979) Abstract No. 1162482.

Haces, A., et al., "Chemical Differentiating Agents. Differentiation of HL–60 Cells by Hexamethylenebis[acetamide] Analogues," *J. Med. Chem.*, 30(2):405–409 (1987).

Fibach, E., et al., "Effect of Hexamethylene Bisacetamide on the Commitment to Differentiation of Murine Erythroleukemia Cells," *Cancer Research*, 37:440–444 (1977).

Egorin, M.J., et al., "Phase I Clinical and Pharmacokinetic Study of Hexamethylene Bisacetamide (NSC 95580)Administered as a Five–Day Continuous Infusion," *Cancer Research*, 47:617–623 (1987).

Yoshida, M., et al., "Potent and Specific Inhibition of Mammalian Histone Deacetylase Both in Vivo and in Vitro by Trichostatin A," *J. of Biol. Chem.*, 265(28):17174–17179 (1990).

Weitl, F., and Raymond, K.N., "Lipophilic Enterobactin Analogues[1]. Terminally N–Alkylated Spermine/Spermidine Catecholcarboxamides," *J. Org. Chem.*, 46(25):5234–5237 (1981).

Toi, K., and Izumi, Y., "Stereoisomers of alpha, alpha–diaminoadipic Acid," *Chemical Abstract*, Caold Accession No. CA55:6371e (1955).

Tanaka, M., et al., "Induction of Erythroid Differentiation in Murine Virus Infected Erythroleukemia Cells by Highly Polar Compounds," *Proc. Nat. Acad. Sci. USA*, 72(3):1003–1006 (1975).

Tabernero, E., et al., "Antitrypansomal (T. Venezuelense) and Antimycotic Effect of Various Hydroxamic Acids," *1–Pharmacology*, 98:27, 1983. (From *Acta Cient. Venez.*, 32(5):411–416, 1981).

Saito, A., et al., "A Synthetic Inhibitor of Histone Deacetylase, MS–27–275, with Marked in Vivo Antitumor Activity Against Human Tumors," *Proc. Natl. Acad. Sci. USA*, 96:4592–4597 (1999).

Rifkind, R.A., and Marks, P.A., "Regulation of Differentiation in Transformed Erythroid Cells," *Blood Cells*, 4:189–206 (1978).

Richon, V.M., et al., "A Class of Hybrid Polar Inducers of Transformed Cell Differentiation Inhibits Histone Deacetylases," *Proc. Natl. Acad. Sci. USA*, 95:3003–3007 (1998).

Reuben, R.C., et al., "A New Group of Potent Inducers of Differentiation in Murine Erythroleukemia Cells," *Proc. Natl. Acad. Sci. USA*, 73(3):862–866 (1976).

Morrison, R.T., and Boyd, R.N., "Conversion of Amines Into Substituted Amides." In *Organic Chemistry* ($3^{rd}$ Edition, Allyn and Bacon, Boston, Massachusetts), pp. 755–758 (1973).

Melloni, E., et al., "Vincristine–Resistant Erythroleukemia Cell Line has Marked Increased Sensitivity to Hexamethylenebisacetamide–Induced Differentiation," *Proc. Natl. Acad. Sci. USA*, 85:3835–3839 (1988).

Marks, P.A., et al., "Polar/Apolar Chemical Inducers of Differentiation of Transformed Cells: Strategies to Improve Therapeutic Potential," *Proc. Natl. Acad. Sci. USA*, 86:6358–6362 (1989).

Marks, P.A., and Rifkind, R.A., "Hexamethylene Bisacetamide–Induced Differentiation of Transformed Cells: Molecular And Cellular Effects and Therapeutic Application," *Int. J. of Cell Cloning*, 6:230–240 (1988).

Marks, P.A., et al., "Induction of Murine Erythroleukemia Cells to Differentiate: A Model for the Detection of New Anti–Tumor Drugs," *Antibiotics Chemother.*, 23:33–41 (1978).

Nakajima, H., et al., "FR901228, A Potent Antitumor Antibiotic, Is a Novel Histone Deacetylase Inhibitor," *Exp. Cell Res.*, 241:126–133 (1998).

Prabhaker, Y.S., et al., "Quantitative Correlations of Biological Activities of Dactinomycin Analogs and Methotrexate Derivatives with van der Waals Volume," *Arzneim.–Forsch./Drug Res.*, 35(7):1030–1033 (1985).

Reuben, R.C., et al., "Chemically Induced Murine Erythroleukemic Differentiation," *Biochimica et Biophysica Acta*, 605:325–346 (1980).

Reuben, R.C., et al., "Inducers of Erythroleukemic Differrentiation," *J. of Biol. Chemistry*, 253(12):4214–4218 (1978).

* cited by examiner

CLASS OF CYTODIFFERENTIATING AGENTS AND HISTONE DEACETYLASE INHIBITORS, AND METHODS OF USE THEREOF

This application claims the benefit of U.S. Provisional Application No. 60/208,688, filed Jun. 1, 2000, and U.S. Provisional Application No. 60/152,755, filed Sep. 8, 1999 now abandoned.

Throughout this application various publications are referenced by Arabic numerals within parentheses. Full citations for these publications may be found at the end of the specification immediately preceding the claims. The disclosures of these publications in their entireties are hereby incorporated by reference into this application in order to more fully describe the state of the art to which this invention pertains.

BACKGROUND OF THE INVENTION

Cancer is a disorder in which a population of cells has become, in varying degrees, unresponsive to the control mechanisms which normally govern proliferation and differentiation. A recent approach to cancer therapy has been to attempt induction of terminal differentiation of the neoplastic cells (1). In cell culture models differentiation has been reported by exposure of cells to a variety of stimuli, including: cyclic AMP and retinoic acid (2,3), aclarubicin and other anthracyclines (4).

There is abundant evidence that neoplastic transformation does not necessarily destroy the potential of cancer cells to differentiate (1,5,6). There are many examples of tumor cells which do not respond to the normal regulators of proliferation and appear to be blocked in the expression of their differentiation program, and yet can be induced to differentiate and cease replicating. A variety of agents, including some relatively simple polar compounds (5,7–9), derivatives of vitamin D and retinoic acid (10–12), steroid hormones (13), growth factors (6,14), proteases (15,16), tumor promoters (17,18), and inhibitors of DNA or RNA synthesis (4,19–24), can induce various transformed cell lines and primary human tumor explants to express more differentiated characteristics.

Early studies by the some of present inventors identified a series of polar compounds that were effective inducers of differentiation in a number of transformed cell lines (8,9). One such effective inducer was the hybrid polar/apolar compound N,N'-hexamethylene bisacetamide (HMBA) (9), another was suberoylanilide hydroxamic acid (SAHA) (39, 50). The use of these compounds to induce murine erythroleukemia (MEL) cells to undergo erythroid differentiation with suppression of oncogenicity has proved a useful model to study inducer-mediated differentiation of transformed cells (5,7–9).

HMBA-induced MEL cell terminal erythroid differentiation is a multistep process. Upon addition of HMBA to MEL cells (745A-DS19) in culture, there is a latent period of 10 to 12 hours before commitment to terminal differentiation is detected. Commitment is defined as the capacity of cells to express terminal differentiation despite removal of inducer (25). Upon continued exposure to HMBA there is progressive recruitment of cells to differentiate. The present inventors have reported that MEL cell lines made resistant to relatively low levels of vincristine become markedly more sensitive to the inducing action of HMBA and can be induced to differentiate with little or no latent period (26).

HMBA is capable of inducing phenotypic changes consistent with differentiation in a broad variety of cells lines (5). The characteristics of the drug induced effect have been most extensively studied in the murine erythroleukemia cell system (5,25,27,28). MEL cell induction of differentiation is both time and concentration dependent. The minimum concentration required to demonstrate an effect in vitro in most strains is 2 to 3 mM; the minimum duration of continuous exposure generally required to induce differentiation in a substantial portion (>20%) of the population without continuing drug exposure is about 36 hours.

There is evidence that protein kinase C is involved in the pathway of inducer-mediated differentiation (29). The in vitro studies provided a basis for evaluating the potential of HMBA as a cytodifferentiation agent in the treatment of human cancers (30). Several phase I clinical trials with HMBA have been completed (31–36). Clinical trials have shown that this compound can induce a therapeutic response in patients with cancer (35,36). However, these phase I clinical trials also have demonstrated that the potential efficacy of HMBA is limited, in part, by dose-related toxicity which prevents achieving optimal blood levels and by the need for intravenous administration of large quantities of the agent, over prolonged periods. Thus, some of the present inventors have turned to synthesizing compounds that are more potent and possibly less toxic than HMBA (37).

Recently, a class of compounds that induce differentiation, have been shown to inhibit histone deacetylases. Several experimental antitumor compounds, such as trichostatin A (TSA), trapoxin, suberoylanilide hydroxamic acid (SAHA), and phenylbutyrate have been shown to act, at least in part, by inhibiting histone deacetylases (38, 39, 42). Additionally, diallyl sulfide and related molecules (43), oxamflatin, (44), MS-27-275, a synthetic benzamide derivative, (45) butyrate derivatives (46), FR901228 (47), depudecin (48), and m-carboxycinnamic acid bishydroxamide (39) have been shown to inhibit histone deacetylases. In vitro, these compounds can inhibit the growth of fibroblast cells by causing cell cycle arrest in the G1 and G2 phases (49–52), and can lead to the terminal differentiation and loss of transforming potential of a variety of transformed cell lines (49–51). In vivo, phenylbutyrate is effective in the treatment of acute promyelocytic leukemia in conjunction with retinoic acid (53). SAHA is effective in preventing the formation of mammary tumors in rats, and lung tumors in mice (54, 55).

U.S. Pat. No. 5,369,108 (41) issued to some of the present inventors discloses compounds useful for selectively inducing terminal differentiation of neoplastic cells, which compounds have two polar end groups separated by a flexible chain of methylene groups, wherein one or both of the polar end groups is a large hydrophobic group. Such compounds are stated to be more active than HMBA and HMBA related compounds.

However, U.S. Pat. No. 5,369,108 does not disclose that an additional large hydrophobic group at the same end of the molecule as the first hydrophobic group would further increase differentiation activity about 100 fold in an enzymatic assay and about 50 fold in a cell differentiation assay.

This new class of compounds of the present invention may be useful for selectively inducing terminal differentiation of neoplastic cells and therefore aid in treatment of tumors in patients.

SUMMARY OF THE INVENTION

The subject invention provides a compound having the formula:

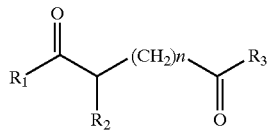

wherein $R_1$ and $R_2$ are the same or different and are each a hydrophobic moiety; wherein $R_3$ is hydroxamic acid, hydroxylamino, hydroxyl, amino, alkylamino, or alkyloxy group; and n is an integer from 3 to 10, or a pharmaceutically acceptable salt thereof.

The subject invention also provides A compound having the formula:

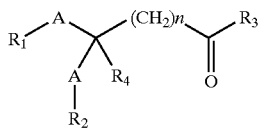

wherein each of $R_1$ and $R_2$ is, substituted or unsubstituted, aryl, cycloalkyl, cycloalkylamino, naphtha, pyridineamino, piperidino, 9-purine-6-amine, thiazoleamino group, hydroxyl, branched or unbranched alkyl, alkenyl, alkyloxy, aryloxy, arylalkyloxy, or pyridine group; wherein $R_3$ is hydroxamic acid, hydroxylamino, hydroxyl, amino, alkylamino, or alkyloxy group; wherein $R_4$ is hydrogen, a halogen, a phenyl, or a cycolalkyl moiety; wherein A may be the same or different and represents an amide moiety, —O—, —S—, —$NR_5$—, or —$CH_2$—, where $R_5$ is a substituted or unsubstituted $C_1$–$C_5$ alkyl; and wherein n is an integer from 3 to 10, or a pharmaceutically acceptable salt thereof.

The subject invention also provides a method of selectively inducing terminal differentiation of neoplastic cells and thereby inhibiting proliferation of such cells which comprises contacting the cells under suitable conditions with an effective amount of the aforementioned compound.

DETAILED DESCRIPTION OF THE INVENTION

Figure 1:
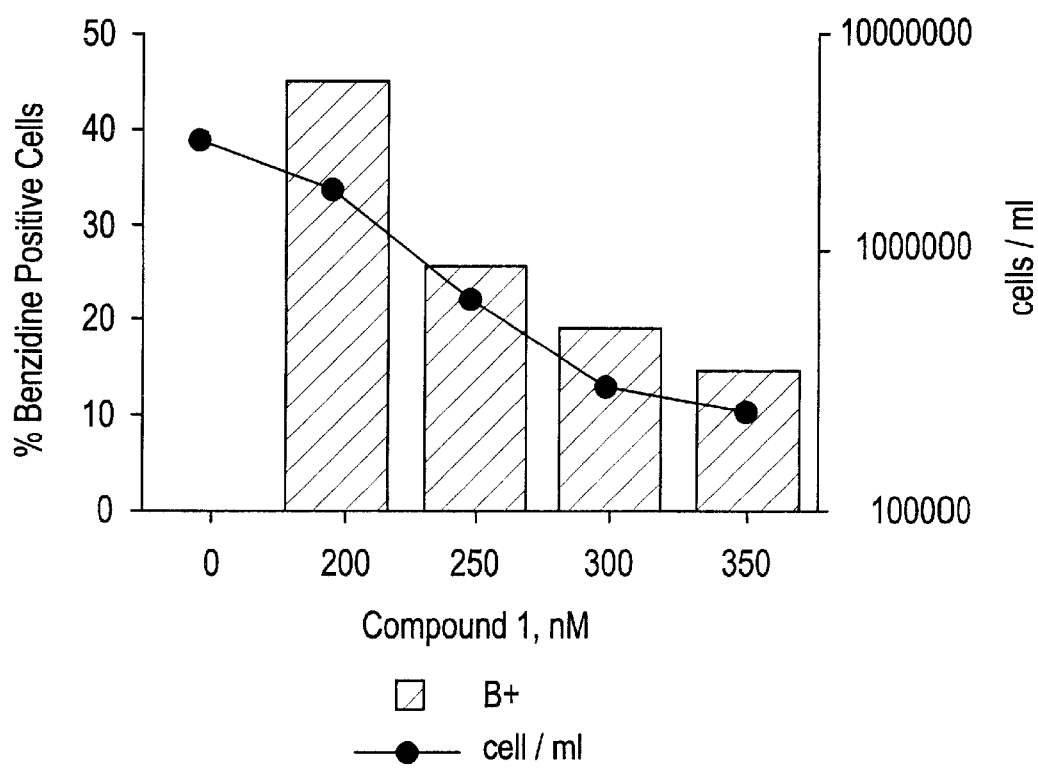
FIG. 1. The effect of Compound 1 according to the subject invention on MEL cell differentiation.

The subject invention provides a compound having the formula:

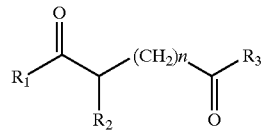

wherein $R_1$ and $R_2$ are the same or different and are each a hydrophobic moiety; wherein $R_3$ is hydroxamic acid, hydroxylamino, hydroxyl, amino, alkylamino, or alkyloxy group; and n is an integer from 3 to 10; or a pharmaceutically acceptable salt of the compound.

In the foregoing compound each of $R_1$ and $R_2$ is directly attached or through a linker, and is, substituted or unsubstituted, aryl, cycloalkyl, cycloalkylamino, naphtha, pyridineamino, piperidino, 9-purine-6-amine, thiazoleamino group, hydroxyl, branched or unbranched alkyl, alkenyl, alkyloxy, aryloxy, arylalkyloxy, or pyridine group.

Where a linker is used, the linker may be an amide moiety, —O—, —S—, —NH—, or —$CH_2$—.

According to this invention, n may be 3–10, preferably 3–8, more preferably 3–7, yet more preferably 4, 5 or 6, and most preferably 5.

In another embodiment of the invention, the compound has the formula:

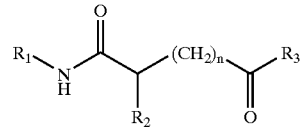

wherein each of $R_1$ is, substituted or unsubstituted, aryl, cycloalkyl, cycloalkylamino, naphtha, pyridineamino, piperidino, 9-purine-6-amine, thiazoleamino group, hydroxyl, branched or unbranched alkyl, alkenyl, alkyloxy, aryloxy, arylalkyloxy, or pyridine group. $R_2$ may be -amide-$R_5$, wherein $R_5$ is, substituted or unsubstituted, aryl, cycloalkyl, cycloalkylamino, naptha, pyridineamino, piperidino, 9-purine-6-amine, thiazoleamino group, hydroxyl, branched or unbranched alkyl, alkenyl, alkyloxy, aryloxy, arylalkyloxy, or pyridine group.

In a further embodiment of the invention the compound has the formula:

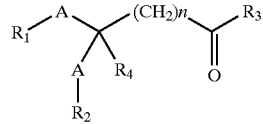

wherein each of $R_1$ and $R_2$ is, substituted or unsubstituted, aryl, cycloalkyl, cycloalkylamino, naphtha, pyridineamino, piperidino, 9-purine-6-amine, thiazoleamino group, hydroxyl, branched or unbranched alkyl, alkenyl, alkyloxy, aryloxy, arylalkyloxy, or pyridine group; wherein $R_3$ is hydroxamic acid, hydroxylamino, hydroxyl, amino, alkylamino, or alkyloxy group; wherein $R_4$ is hydrogen, a halogen, a phenyl, or a cycolalkyl moiety; wherein A may be the same or different and represents an amide moiety, —O—, —S—, —$NR_5$—, or —$CH_2$—, where $R_5$ is a substituted or unsubstituted $C_1$–$C_5$ alkyl; and wherein n is an integer from 3 to 10, or a pharmaceutically acceptable salt thereof.

In another embodiment the compound has the formula:

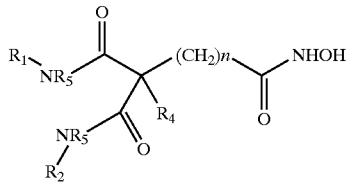

In yet another embodiment, the compound has the formula:

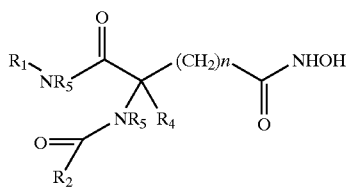

In a further embodiment, the compound has the formula:

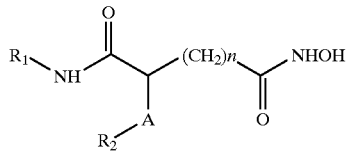

wherein each of $R_1$ and $R_2$ is, substituted or unsubstituted, aryl, cycloalkyl, cycloalkylamino, naphtha, pyridineamino, piperidino, t-butyl, aryloxy, arylalkyloxy, or pyridine group; and wherein n is an integer from 3 to 8.

The aryl or cycloalkyl group may be substituted with a methyl, cyano, nitro, trifluoromethyl, amino, aminocarbonyl, methylcyano, chloro, fluoro, bromo, iodo, 2,3-difluoro, 2,4-difluoro, 2,5-difluoro, 3,4-difluoro, 3,5-difluoro, 2,6-difluoro, 1,2,3-trifluoro, 2,3,6-trifluoro, 2,4,6-trifluoro, 3,4,5-trifluoro, 2,3,5,6-tetrafluoro, 2,3,4,5,6-pentafluoro, azido, hexyl, t-butyl, phenyl, carboxyl, hydroxyl, methoxy, phenyloxy, benzyloxy, phenylaminooxy, phenylaminocarbonyl, methyoxycarbonyl, methylaminocarbonyl, dimethylamino, dimethylaminocarbonyl, or hydroxylaminocarbonyl group.

In a further embodiment, the compound has the formula:

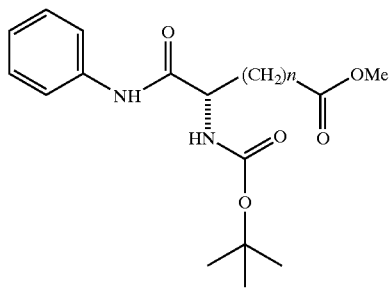

or an enantiomer thereof.

In a yet further embodiment, the compound has the formula:

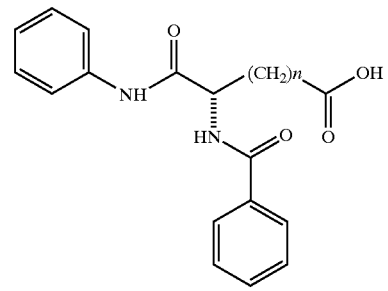

or an enantiomer thereof.

In a further embodiment, the compound has the formula:

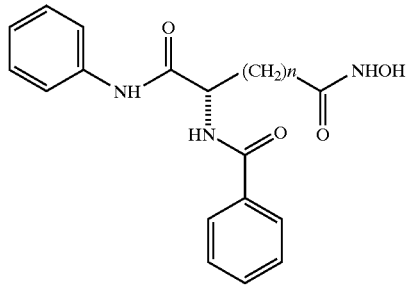

or an enantiomer thereof.

In a yet further embodiment, the compound has the formula:

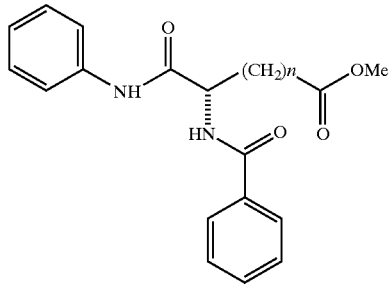

or an enantiomer thereof.

In a further embodiment, the compound has the formula:

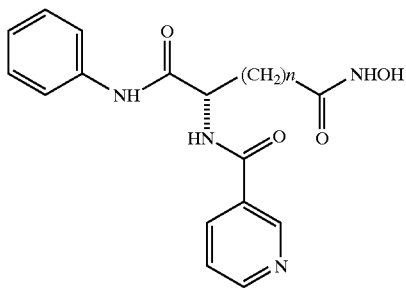

or an enantiomer thereof.

In a yet further embodiment, the compound has the formula:

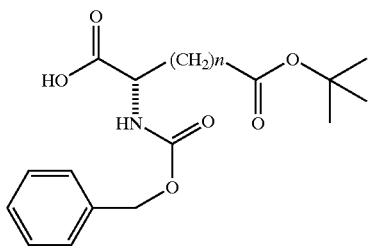

or an enantiomer thereof.

In a yet further embodiment, the compound has the formula:

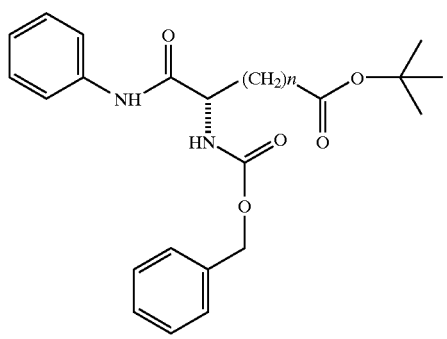

or an enantiomer thereof.

In a further embodiment, the compound has the formula:

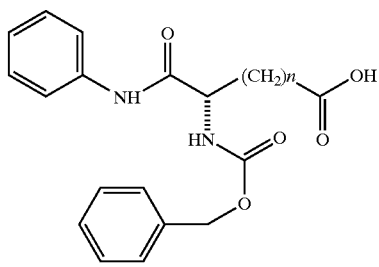

or an enantiomer thereof.

In a further embodiment, the compound has the formula:

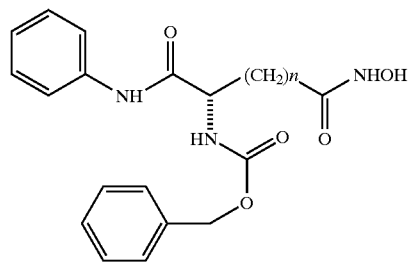

or an enantiomer thereof.

In a yet further embodiment, the compound has the formula:

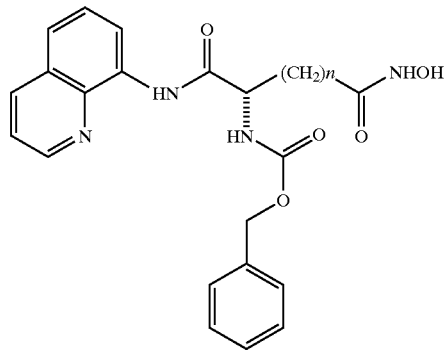

or an enantiomer thereof.

In a further embodiment, the compound has the formula:

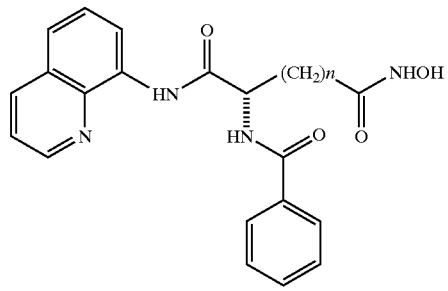

or an enantiomer thereof.

This invention is also intended to encompass enantiomers and salts of the compounds listed above.

In a further embodiment, the compound has the formula:

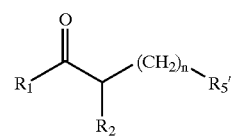

wherein $R_1$ and $R_2$ are the same or different and are each a hydrophobic moiety:
  wherein $R_5'$ is —C(O)—NHOH (hydroxamic acid), —C(O)—CF$_3$ (trifluoroacetyl), —NH—P(O))H—CH$_3$, —SO$_2$NH$_2$ (sulfonamide), —SH (thiol), —C(O)—R$_6$, wherein R$_6$ is hydroxyl, amino, alkylamino, or alkyloxy group; and
  n is an integer from 3 to 10, or a pharmaceutically acceptable salt thereof.

In the foregoing compound, each of $R_1$ and $R_2$ may be directly attached or through a linker, and is, substituted or unsubstituted, aryl, cycloalkyl, cycloalkylamino, naphtha, pyridineamino, piperidino, 9-purine-6-amine, thiazoleamino group, hydroxyl, branched or unbranched alkyl, alkenyl, alkyloxy, aryloxy, arylalkyloxy, or pyridine group.

The linker may be an amide moiety, —O—, —S—, —NH—, or —CH$_2$—.

In another embodiment, the compound has the formula:

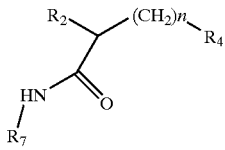

wherein each of $R_7$ is, substituted or unsubstituted, aryl, cycloalkyl, cycloalkylamino, naphtha, pyridineamino, piperidino, 9-purine-6-amine, thiazoleamino group, hydroxyl, branched or unbranched alkyl, alkenyl, alkyloxy, aryloxy, arylalkyloxy, or pyridine group.

In the foregoing compound, $R_2$ may be -sulfonamide-$R_8$, or -amide-$R_8$, wherein $R_8$ is, substituted or unsubstituted, aryl, cycloalkyl, cycloalkylamino, naphtha, pyridineamino, piperidino, 9-purine-6-amine, thiazoleamino group, hydroxyl, branched or unbranched alkyl, alkenyl, alkyloxy, aryloxy, arylalkyloxy, or pyridine group.

The $R_2$ may be —NH—C(O)—Y, —NH—SO$_2$—Y, wherein Y is selected from the group consisting of:

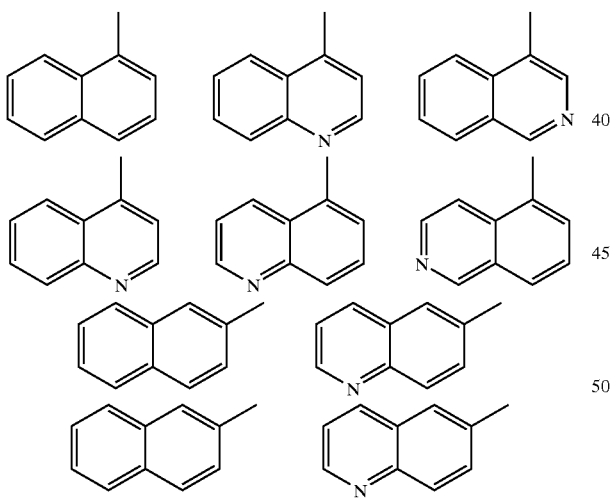

The $R_7$ may be selected from the group consisting of the following and designated $R_7'$:

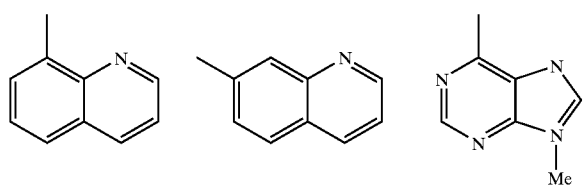

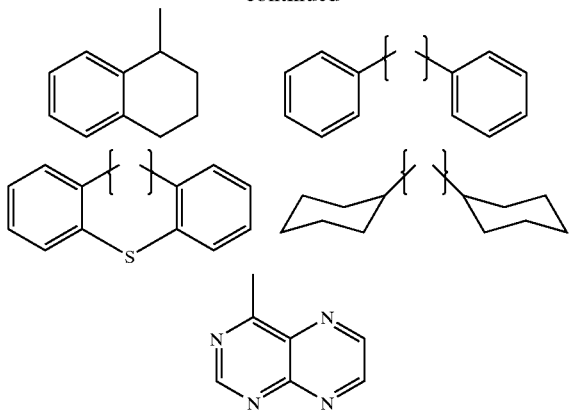

In yet another embodiment, the compound has the formula:

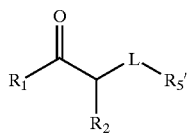

wherein $R_1$ and $R_2$ are the same or different and are each a hydrophobic moiety:

wherein $R_5'$ is —C(O)—NHOH (hydroxamic acid), —C(O)—CF$_3$ (trifluoroacetyl), —NH—P(O))H—CH$_3$, —SO$_2$NH$_2$ (sulfonamide), —SH (thiol), —C(O)—R$_6$, wherein R$_6$ is hydroxyl, amino, alkylamino, or alkyloxy group; and wherein L is a linker consisting of —(CH$_2$)—, —C(O)—, —S—, —O—, —(CH=CH)—, -phenyl-, or -cycloalkyl-, or any combination thereof, or a pharmaceutically acceptable salt thereof.

L may also be a linker consisting of —(CH$_2$)$_n$—, —C(O)—, —S—, —O—, —(CH=CH)$_m$—, -phenyl-, or -cycloalkyl-, or any combination thereof, wherein n is an integer from 3 to 10, and m is an integer from 0 to 10, In the foregoing compound, n may be from 4–7, and m is from 0–7. Preferably n is 5 or 6, most preferably n is 6. Preferably m is from 1–6, more preferably m is 2–5, most preferably m is 3 or 4, In the compound, each of $R_1$ and $R_2$ may be directly attached or through a linker, and is, substituted or unsubstituted, aryl, cycloalkyl, cycloalkylamino, naphtha, pyridineamino, piperidino, 9-purine-6-amine, thiazoleamino group, hydroxyl, branched or unbranched alkyl, alkenyl, alkyloxy, aryloxy, arylalkyloxy, or pyridine group.

The linker may be an amide moiety, —O—, —S—, —NH—, or —CH$_2$—.

This invention is also intended to encompass enantiomers, salts and pro-drugs of the compounds disclosed herein.

In another embodiment the compound may have the formula:

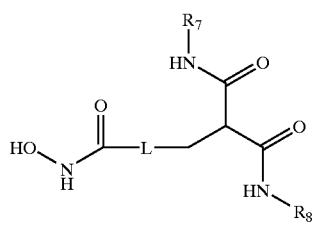

wherein L is a linker selected from the group consisting of —(CH$_2$)—, —(CH=CH)—, -phenyl-, -cycloalkyl-, or any combination thereof; and wherein each of R$_7$ and R$_1$ are independently substituted or unsubstituted, aryl, cycloalkyl, cycloalkylamino, naphtha, pyridineamino, piperidino, 9-purine-6-amine, thiazoleamino group, hydroxyl, branched or unbranched alkyl, alkenyl, alkyloxy, aryloxy, arylalkyloxy, or pyridine group.

In a preferred embodiment, the linker L comprises the moiety

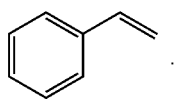

In another preferred embodiment, the compound has the formula:

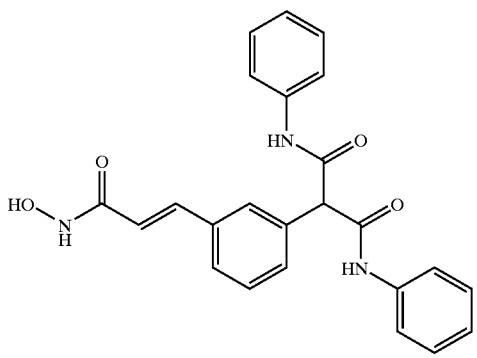

Any of the disclosed compounds can be formed into a pharmaceutical composition together with a pharmaceutically acceptable carrier.

Any of the compounds can also be formed into a pharmaceutically acceptable salt of the compound using well known pharmacological techniques.

A prodrug of any of the compounds can also be made using well known pharmacological techniques.

Any of the compounds can be used in a method of inducing differentiation of tumor cells in a tumor comprising contacting the cells with an effective amount of the compound so as to thereby differentiate the tumor cells.

Any of the compounds can also be used in a method of inhibiting the activity of histone deacetylase comprising contacting the histone deacetylase with an effective amount of the compound so as to thereby inhibit the activity of histone deacetylase.

This invention, in addition to the above listed compounds, is further intended to encompass the use of homologs and analogs of such compounds. In this context, homologs are molecules having substantial structural similarities to the above-described compounds and analogs are molecules having substantial biological similarities regardless of structural similarities.

In a further embodiment, the subject invention provides a pharmaceutical composition comprising a pharmaceutically effective amount of any one of the aforementioned compounds and a pharmaceutically acceptable carrier.

In a yet further embodiment, the subject invention provides a method of selectively inducing growth arest, terminal differentiation and/or apoptosis of neoplastic cells and thereby inhibiting proliferation of such cells which comprises contacting the cells under suitable conditions with an effective amount of any one of the aforementioned compounds.

The contacting should be performed continuously for a prolonged period of time, i.e. for at least 48 hours, preferably for about 4–5 days or longer.

The method may be practiced in vivo or in vitro. If the method is practiced in vitro, contacting may be effected by incubating the cells with the compound. The concentration of the compound in contact with the cells should be from about 1 nM to about 25 mM, preferably from about 20 nM to about 25 mM, more preferably from about 40 nM to 100 μM, yet more preferably from about 40 nM to about 200 nM. The concentration depends upon the individual compound and the state of the neoplastic cells.

The method may also comprise initially treating the cells with an antitumor agent so as to render them resistant to an antitumor agent and subsequently contacting the resulting resistant cells under suitable conditions with an effective amount of any of the compounds above, effective to selectively induce terminal differentiation of such cells.

The present invention also provides a method of treating a patient having a tumor characterized by proliferation of neoplastic cells which comprises administering to the patient an effective amount of any of the compounds above, effective to selectively induce growth arrest, terminal differentiation and/or apoptosis of such neoplastic cells and thereby inhibit their proliferation.

The method of the present invention is intended for the treatment of human patients with tumors. However, it is also likely that the method would be effective in the treatment of tumors in other mammals. The term tumor is intended to include any cancer caused by the proliferation of neoplastic cells, such as prostate cancer, lung cancer, acute leukemia, multiple myeloma, bladder carcinoma, renal carcinoma, breast carcinoma, colorectal carcinoma, neuroblastoma or melanoma.

Routes of administration for the compound of the present invention include any conventional and physiologically acceptable route, such as, for example, oral, pulmonary, parenteral (intramuscular, intraperitoneal, intravenous (IV) or subcutaneous injection), inhalation (via a fine powder formulation or a fine mist), transdermal, nasal, vaginal, rectal, or sublingual routes of administration and can be formulated in dosage forms appropriate for each route of administration.

The present invention also provides a pharmaceutical composition comprising a pharmaceutically acceptable carrier, such as sterile pyrogen-free water, and a therapeutically acceptable amount of any of the compounds above. Preferably, the effective amount is an amount effective to selectively induce terminal differentiation of suitable neoplastic cells and less than an amount which causes toxicity in a patient.

The present invention provides the pharmaceutical composition above in combination with an antitumor agent, a hormone, a steroid, or a retinoid.

The antitumor agent may be one of numerous chemotherapy agents such as an alkylating agent, an antimetabolite, a hormonal agent, an antibiotic, colchicine, a vinca alkaloid, L-asparaginase, procarbazine, hydroxyurea, mitotane, nitrosoureas or an imidazole carboxamide. Suitable agents are those agents which promote depolarization of tubulin. Preferably the antitumor agent is colchicine or a vinca alkaloid; especially preferred are vinblastine and vincristine.

In embodiments where the antitumor agent is vincristine, an amount is administered to render the cells are resistant to vincristine at a concentration of about 5 mg/ml. The administration of the agent is performed essentially as described above for the administration of any of the compounds. Preferably, the administration of the agent is for a period of at least 3–5 days. The administration of any of the compounds above is performed as described previously.

The pharmaceutical composition may be administered daily in 2–6 hour infusions for a period of 3–21 days, for example, daily in a 4 hour infusion for a period of 5 days.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Examples 1–5 show the synthesis of substituted L-α-aminosuberic hydroxamic acids according to the subject invention, and Examples 6 and 7 show the effects of compounds 1–5 on MEL cell differentiation and Histone Deacetylase activity.

EXAMPLE 1

Synthesis of Compound 1

N-Boc-ω-methyl-(L)-α-aminosuberate, Boc-Asu(OMe) was prepared according to a published procedure (40). ("Boc"=t-butoxycarbonyl; "Asu"=α-aminosuberate (or α-aminosuberic acid)).

N-Cbz-ω-t-butyl-(L)-α-aminosuberate, dicyclohexylamine salt was purchased from Research Plus, Bayonne, N.J.

N-Boc-ω-methyl-(L)-α-aminosuberateanilide, Boc-Asu(OMe)—NHPh.

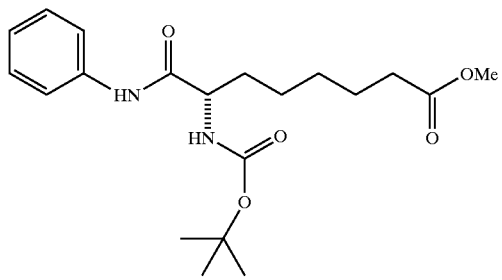

(I1)

N-Boc-ω-methyl-(L)-α-aminosuberate (493 mg, 1.63 mmoles) was dissolved under Ar in 7 mL of dry CH$_2$Cl$_2$. EDC (470 mg, 2.45 mmoles) was added, followed by aniline (230 μL, 2.52 mmoles). The solution was stirred at room temperature for 2 h 30 min, then washed with dilute HCl (pH 2.4, 2×5 mL), sat. NaHCO$_3$ (10 mL), and H$_2$O (2×10 mL). The product was purified by column chromatography (Silica gel, Hexanes:AcOEt 3.5:1). The isolated yield was 366 mg (60%).

$^1$H-NMR and Mass Spectroscopy were consistent with the product.

N-Benzoyl-ω-methyl-(L)-α-aminosuberateanilide, PhCOHN-Asu(OMe)—NHPh.

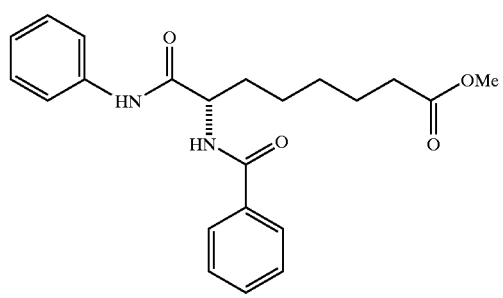

(I2)

90 mg of N-Bloc-ω-methyl-(L)-α-aminosuberateanilide (0.238 mmoles) were treated with 3.2 mL of 25% trifluoroacetic acid (TFA) CH$_2$Cl$_2$ for 30 min. The solvent was removed and the residue left under high vacuum for 12 h. It was dissolved under Ar in 3 mL of dry CH$_2$Cl$_2$ and benzotriazole-1-yloxy-tris-pyrrolidinophosphonium hexafluorophosphate (PyBOP) (149 mg, 0.286 mmoles), benzoic acid (44 mg, 0.357 mmoles) and diisopropylethylamine (114 μL, 0.655 mmoles). The solution was stirred at room temperature for 1 h. The product was purified by column chromatography (Silica gel, Hexanes:AcOEt 3:1–2:1) as a white solid: 75 mg, 82%.

$^1$H-NMR and Mass Spectroscopy were consistent with the product.

The foregoing coupling reaction was also successfully accomplished using 1-(3-dimethylaminopropyl)-3-ethylcarbodiimide hydrochloride (EDC) as a reagent.

N-Benzoyl-(L)-α-aminosuberoylanilide, PhCONH-Asu(OH)—NHPh.

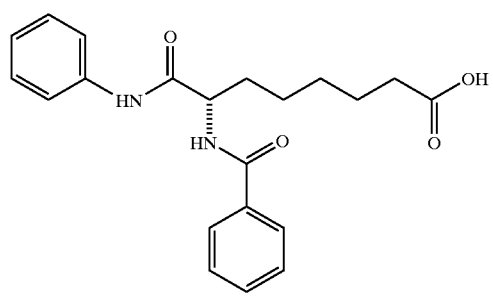

(I3)

75 mg (0.196 mmoles) of N-benzoyl-aminosuberateanilide were stirred for 6 h at 0° C. in 1M NaOH:THF:MeOH 1:1:1. After complete disappearance of the starting material, the solution was neutralized (1M HCl) and extracted with AcOEt. The organic phase was collected and dried. Solvent removal yielded the product as a white solid: 67 mg, 93%.

$^1$H-NMR and Mass Spectroscopy were consistent with the product.

N-Benzoyl-(L)-α-aminosuberoylanilide-ω-hydroxamic Acid, PhCONH-Asu(NHOH)—NHPh:

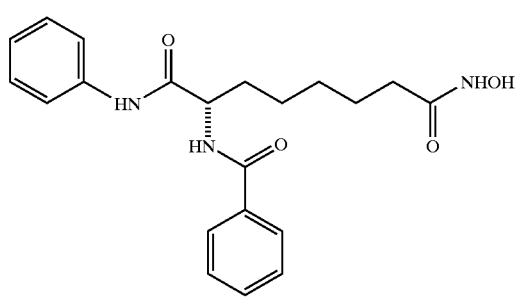

(1)

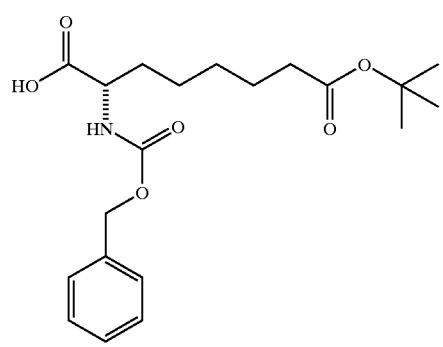

(14)

To a suspension of 26 mg of N-benzoyl-ω-methyl-(L)-α-aminosuberateanilide (I2) in 1 mL of dry $CH_2Cl_2$ was added 58 mg of $H_2$NOTBDPS ($H_2$NO-t-butyldiphenylsilyl) followed by 22 mg of EDC. The reaction was stirred at room temperature for 4 h. The intermediate protected hydroxamic acid was purified by column chromatography (silica gel, $CH_2Cl_2$:MeOH 100:0-98-2). It was deprotected by treatment with 5% TFA in $CH_2Cl_2$ for 1 h 30 min. The product was precipitated from acetone-pentane.

$^1$H-NMR ($d_6$-DMSO, 500 MHz) δ=10.29 (s, 1H), 8.53 (d, 1H), 7.90 (d, 2H), 7.60 (d, 2H), 7.53 (m, 1H), 7.46 (t, 2H), 7.28 (t, 2H), 7.03 (t, 2H), 4.53 (q, 1H), 1.92 (t, 2H), 1.78 (m, 2H), 1.50–1.25 (m, 6H). ESI-MS: 384 (M+1), 406 (M+Na), 422 (M+K).

N-Cbz-(L)-Asu(OtBu)—OH, dicyclohexylamine salt (100 mg, 0.178 mmol) was partitioned between 1 M HCl (5 mL) and EtOAc (10 mL).

The organic layer was removed, and the aqueous portion washed with EtOAc (3×3 mL). The organic fractions were combined, washed with brine (1×2 mL), and dried ($MgSO_4$). The mixture was filtered and concentrated to a colorless film (67 mg, 0.176 mmol, 99%). This compound was used immediately in the next step.

N-Benzyloxycarbonyl-ω-t-butyl-(L)-α-aminosuberateanilide, N-Cbz-(L)-Asu(OtBu)—NHPh.

EXAMPLE 2

Synthesis of Compound 2

N-Nicotinoyl-(L)-α-aminosuberoylanilide-ω-hydroxamic Acid, $C_5H_4$NCO-Asu(NHOH)—NHPh:

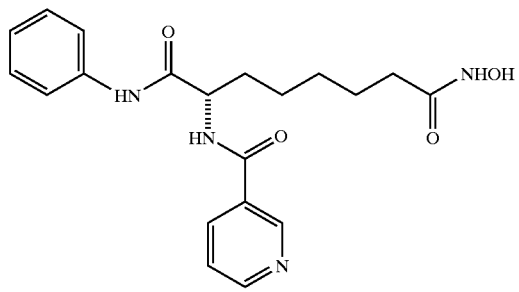

(2)

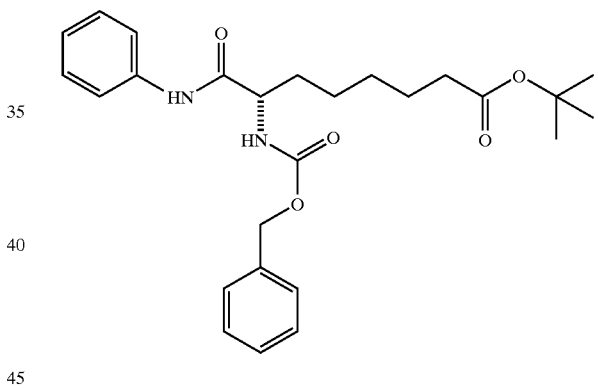

(15)

It was prepared from N-Boc-ω-methyl-L-α-aminosuberate following the same procedure used for the benzoyl analog. Yields and chromatographic behaviour were comparable. $^1$H-NMR ($d_6$-DMSO, 500 MHz) δ=10.30 (s, 1H), 10.10 (s, 1H), 9.05 (m, 1H), 8.80 (m, 1H), 8.71 (m, 1H), 8.24 (m, 1H), 7.60 (m, 2H), 7.30 (m, 2H), 7.04 (m, 1H), 4.56 (m, 1H), 1.93 (t, 2H), 1.79 (m, 2H), 1.55–1.30 (m, 6H). ESI-MS: 385 (M+1), 407 (M+Na).

EXAMPLE 3

Synthesis of Compound 3

N-Benzyloxycarbonyl-ω-t-butyl-(L)-aminosuberic Acid, N-Cbz-(L)-Asu(OtBu)—OH.

N-Cbz-(L)-Asu(OtBu)—OH (67 mg, 0.176 mmol) was dissolved in dry $CH_2Cl_2$ (2.5 mL). Aniline (17 µL, 0.187 mmol), PyBOP (97 mg, 0.187 mmol), and $iPr_2$NEt (46 µL, 0.266 mmol) were added and the mixture stirred for 2 h. The reaction was complete as indicated by TLC. The mixture was diluted with EtOAc (5 mL) and water (5 mL), and the layers separated. The aqueous portion was washed with EtOAc (3×3 mL) and the organic fractions combined. This solution was washed with 1 M HCl (1×2 mL) and brine (1×2 mL), dried ($MgSO_4$), filtered, and concentrated to a crude oil.

This was passed through a plug of silica gel (30% EtOAc/hexanes) to remove baseline impurities, affording the compound (76 mg, 0.167 mmol, 94%).

$^1$H NMR ($CDCl_3$, 400 MHz, no TMS) δ 8.20 (br s, 1H), 7.47 (d, 2H), 7.32 (m, 5H), 7.28 (t, 2H), 7.08 (t, 1H), 5.39 (d, 1H), 5.10 (m, 2H), 4.26 (m, 1H), 2,18 (t, 2H), 1.93 (m, 1H), 1.67 (m, 1H), 1.55 (m, 3H), 1.42 (s, 9H), 1.36 (m, 3H). N-Benzyloxycarbonyl-(L)-α-aminosuberateanilide, N-Cbz-(L)-Asu(OH)—NHPh.

(16)

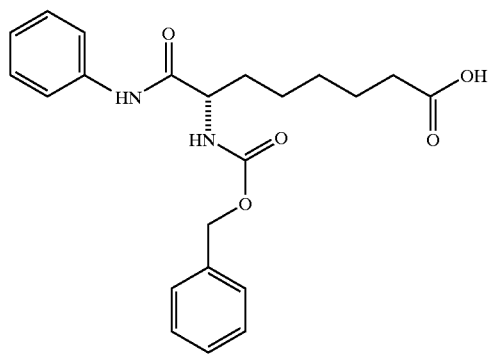

N-Cbz-(L)-Asu(OtBu)-anilide (76 mg, 0.167 mmol) was dissolved in dry $CH_2Cl_2$ (5 mL) and TFA (0.5 mL) added dropwise. The reation was complete by TLC after 3 h. The mixture was concentrated in vacuo to give the title compound (80 mg, crude). This compound was taken on without purification to the next step.

$^1$H NMR (DMSO-$d_6$, 400 MHz) δ 11.93 (br s, 1H), 9.99 (br s, 1H), 7.57 (m, 3H), 7.34 (m, 5H), 7.29 (t, 2H), 7.03 (t, 1H), 5.02 (m, 2H), 4.11 (m, 1H), 2.17 (t, 2H), 1.61 (m, 2H), 1.46 (m, 2H), 10 1.27 (m, 4H).

N-Benzyloxycarbonyl-(L)-α-aminosuberateanilide ω-Hydroxamic Acid, N-Cbz-(L)-Asu(NH—OH)—NHPh.

(3)

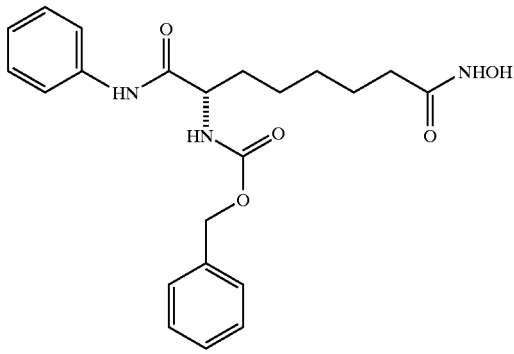

N-Cbz-(L)-Asu(OH)-anilide (80 mg, crude) and O-t-butyldiphenylsilyl-hydroxylamine (60 mg, 0.221 mmol) were dissolved in $CH_2Cl_2$ (4 mL). To this was added PyBOP (125 mg, 0.241 mmol) and $iPr_2NEt$ (52 μL, 0.302 mmol) and stirred overnight. TLC indicated reaction completion. The mixture was concentrated in vacuo and then passed through a plug of silica gel (50% EtOAc/hexanes) to remove baseline impurities. Evaporation of volatiles afforded 107 mg of material which was then dissolved in dry $CH_2Cl_2$ (5 mL) and TFA (0.25 mL) was added. Monitoring by TLC indicated completion after 1.5 h. Concentrated in vacuo to remove all volatiles. The reside was taken up in EtOAc (3 mL), and then hexanes was added slowly to result in the precipitation of a white gel. The supernatant was removed, and the precipitate washed with hexanes (3×2 mL). This material was taken to dryness under reduced pressure, to afford the title compound (40 mg, 0.097 mmol, 59%).

$^1$H NMR (DMSO-$d_6$, 400 MHz) δ 10.32 (s, 1H), 10.00 (s, 1H), 8.64 (br s, 1H), 7.57 (m, 3H), 7.37 (m, 5H), 7.30 (t, 2H), 7.04 (t, 1H), 5.02 (m, 2H), 4.12 (m, 1H), 1.93 (t, 2H), 1.62 (m, 2H), 1.45 (m, 2H), 1.29 (m, 4H); ESI-MS 414 (M+1).

EXAMPLE 4

Synthesis of Compound 4

N-Benzyloxycarbonyl-(L)-α-aminoxuberoyl-8-quinolinamide-ω-hydroxamic Acid.

(4)

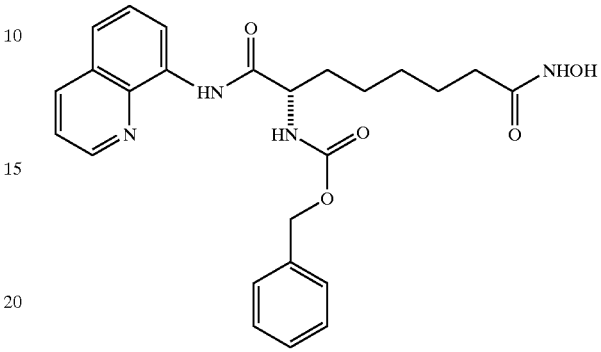

Prepared in similar manner to compound 3.

1H NMR (DMSO-d6, 400 MHz) δ 10.45 (s, 1H), 10.31 (s, 1H), 8.85 (dd, 1H), 8.63 (dd, 1H), 8.42 (dd, 1H), 8.13 (dd, 1H), 8.68 (m, 2H), 7.60 (t, 1H), 7.37 (m, 2H), 7.28 (m, 2H), 5.10 (m, 2H), 4.24 (m, 1H), 1.93 (t, 2H), 1.85 (m, 1H), 1.70 (m, 1H), 1.50 (m, 2H), 1.42 (m, 2H), 1.30 (m, 2H); ESI-MS 465 (M+1).

EXAMPLE 5

Synthesis of Compound 5

N-Benzoyl-(L)-α-aminosuberoyl-8-quinolinamide-ω-hydroxamic Acid:

(5)

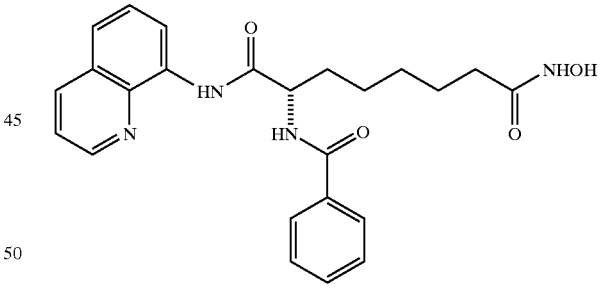

A sample of the N-Cbz-ω-t-butyl L-α-aminosuberoyl-8-quinolinamide (90 mg, 0.178 mmoles) was obtained from the previous synthesis. The Cbz group was removed by hydrogenation in MeOH on 5%Pd on C. The resulting free amine was coupled with benzoic acid using EDC in dry $CH_2Cl_2$ (69% over the two steps) After TFA deprotection of the t-butyl ester, the usual coupling with $H_2NOTBDPS$ followed by deprotection afforded the desired hydroxamic acid.

$^1$H-NMR ($d_6$-DMSO, 500 MHz) δ=10.55 (s, 1H), 10.30 (s, 1H), 9.03 (m, 1H), 8.78 (m, 1H), 8.62 (m, 1H), 8.40 (m, 1H0, 7.97 (m, 2H), 7.67–7.46 (m, 6H), 4.66 (m, 1H), 1.94 (t, 2H), 1.87 (m, 1H), 1.80–1.20 (m, 7H). ESI-MS: 435 (M+1).

EXAMPLE 6

Synthesis of Compound with Inverted Amide Group

A compound having the following formula:

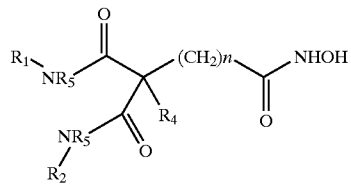

is synthesized by treating a malonic ester:

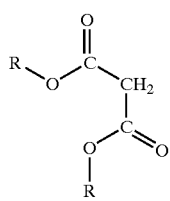

with a base, and then adding:

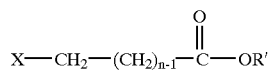

where X is a halogen, to form:

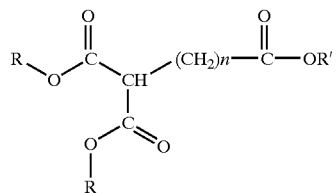

from which R is removed by reaction with an amine and a carbodiimide reagent ro form:

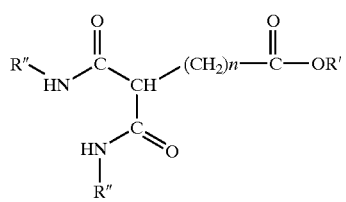

from which R' is removed and converted to hydroxamic acid (NHOH) as in the previous examples.

In the foregoing scheme, R may be t-butyl, removed with trifluoroacetic acid; R' may be methyl, removed with a base or LiI; and each R″ may be the same or different, depending on the reagent used.

EXAMPLE 7

Effect of Compound 1 (N-Benzoyl-(L)-α-aminosuberoylanilide-ω-hydroxamic Acid, PhCONH-Asu(NHOH)—NHPh) on MEL Cell Differentiation and Histone Deacetylase Activity Murine Erythroleukemia (MEL) Cell Differentiation.

The MEL cell differentiation assay was used to assess the ability of Compound 1 to induce terminal differentiation. MEL cells (logarithmically dividing) were cultured with the indicated concentrations of Compound 1. Following a 5-day culture period, cell growth was determined using a Coulter Counter and differentiation was determined microscopically using the benzidine assay to determine hemoglobin protein accumulation on a per cell basis.

It was observed, as shown in FIG. 1, that Compound 1 (200 nM) is able to induce MEL cell differentiation.

Histone Deacetylase (HDAC) Enzymatic Activity.

The effect of Compound 1 on affinity purified human epitope-tagged (Flag) HDAC1 was assayed by incubating the enzyme preparation in the absence of substrate on ice for 20 min with the indicated amounts of Compound 1. Substrate ([$^3$H]acetyl-labeled murine erythroleukemia cell-derived histone) was added and the samples were incubated for 20 min at 37° C. in a total volume of 30 μl. The reactions were then stopped and released acetate was extracted and the amount of radioactivity released determined by scintillation counting.

Figure 2:
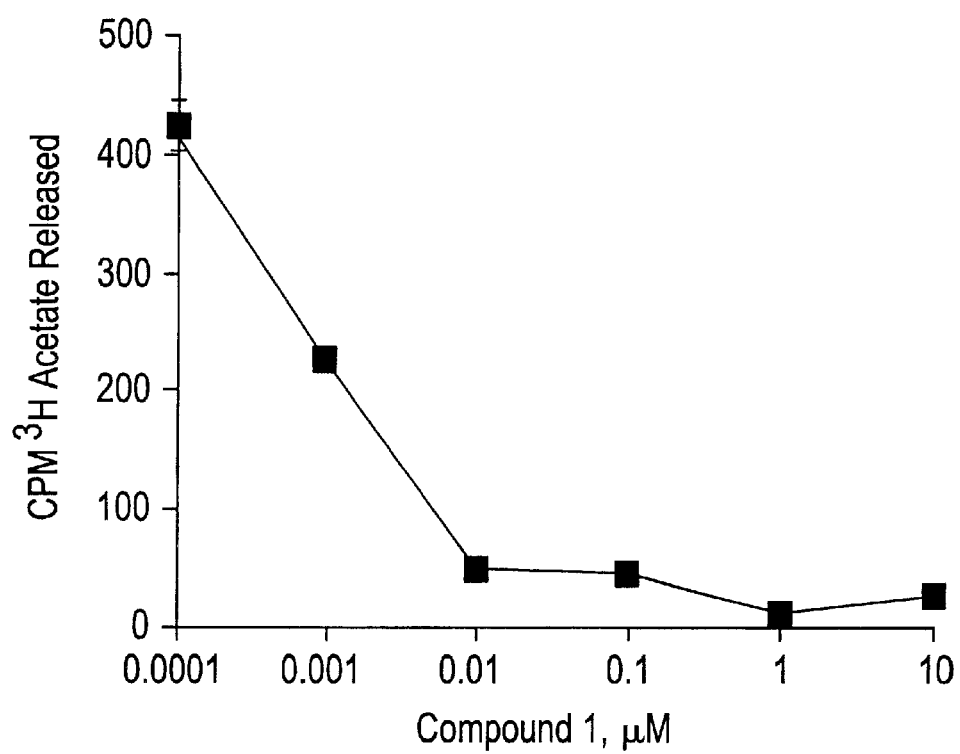
FIG. 2. The effect of Compound 1 according to the subject invention on Histone Deacetylase 1 activity.

It was observed, as shown in FIG. 2, that Compound 1 is a potent inhibitor of HDAC1 enzymatic activity ($ID_{50}$=1 nM).

EXAMPLE 8

Effect of Compound 2 (N-Nicotinoyl-(L)-α-aminosuberoylanilide-ω-hydroxamic Acid, C$_5$H$_4$NCO-Asu(NHOH)—NHPh) on MEL Cell Differentiation Murine Erythroleukemia (MEL) Cell Differentiation:

The MEL cell differentiation assay was used to assess the ability of Compound 2 to induce terminal differentiation. MEL cells (logarithmically dividing) were cultured with the indicated concentrations of Compound 2. Following a 5-day culture period differentiation was determined microscopically using the benzidine assay to determine hemoglobin protein accumulation on a per cell basis.

Figure 3:
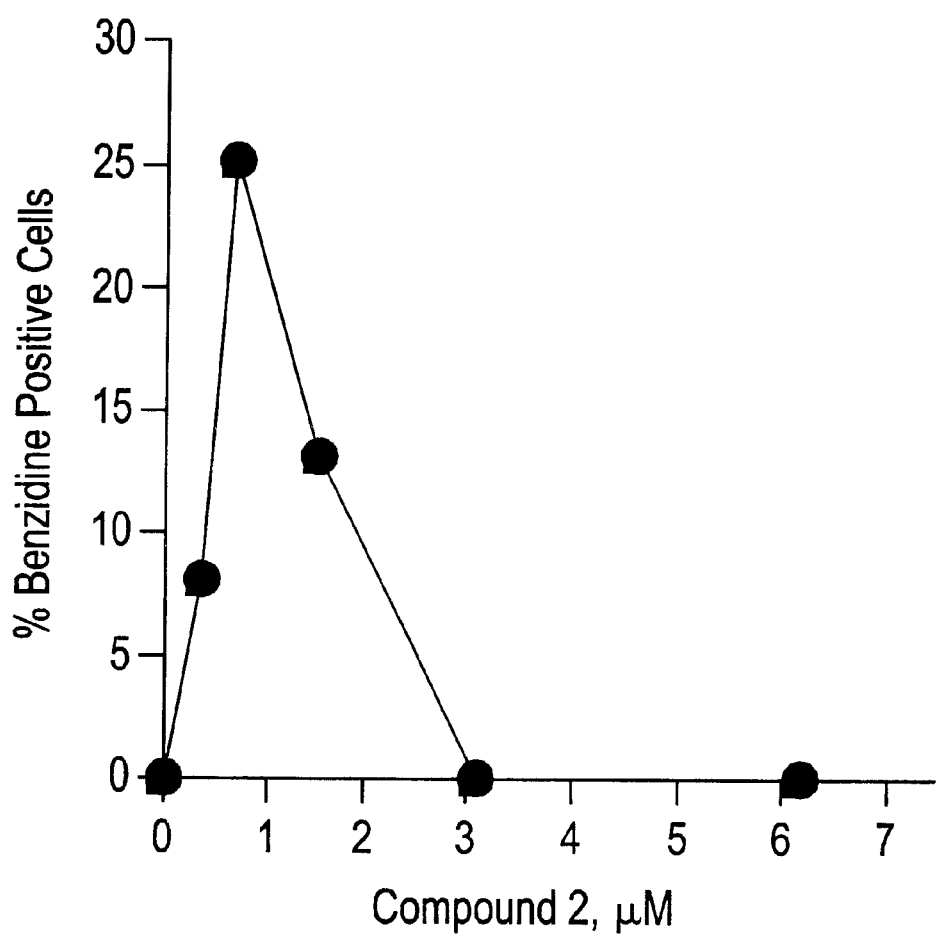
FIG. 3. The effect of Compound 2 according to the subject invention on MEL cell differentiation.

It was observed, as shown in FIG. 3, that Compound 2 (800 nM) is able to induce MEL cell differentiation.

EXAMPLE 9

Effect of Compound 3 (N-Benzyloxycarbonyl-(L)-ω-aminosuberateanilide ω-Hydroxamic Acid, N-Cbz-(L)-Asu(NH—OH)—NHPh) on MEL Cell Differentiation and Histone Deacetylase Activity Murine Erythroleukemia (MEL) Cell Differentiation:

The MEL cell differentiation assay was used to assess the ability of Compound 3 to induce terminal differentiation. MEL cells (logarithmically dividing) were cultured with the indicated concentrations of Compound 3. Following a 5-day culture period differentiation was determined microscopically using the benzidine assay to determine hemoglobin protein accumulation on a per cell basis.

Figure 4:
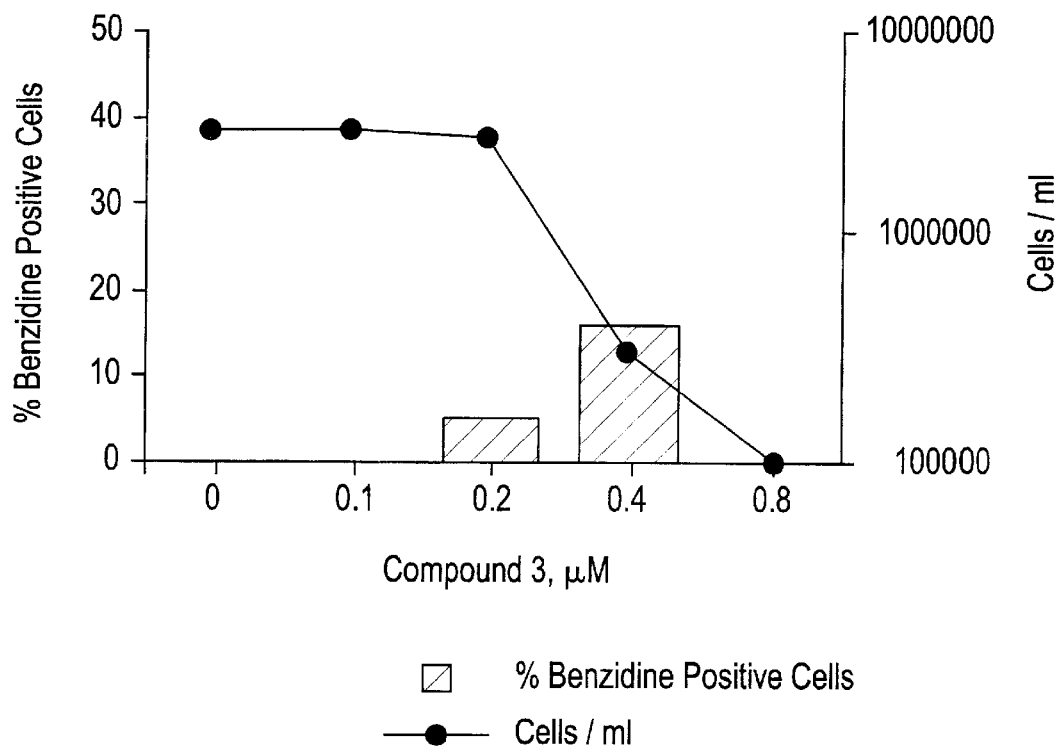
FIG. 4. The effect of Compound 3 according to the subject invention on MEL cell differentiation.

It was observed, as shown in FIG. 4, that Compound 3 (400 nM) is able to induce MEL cell differentiation.

Histone Deacetylase (HDAC) Enzymatic Activity:

The effect of Compound 3 on affinity purified human epitopetagged (Flag) HDAC1 was assayed by incubating the enzyme preparation in the absence of substrate on ice for 20 min with the indicated amounts of HPC. Substrate ([$^3$H] accetyl-labelled murine erythroleukemia cell-derived histone) was added and the samples were incubated for 20 min at 37° C. in a total volume of 30 μl. The reactions were then stopped and relaesed acetate was extracted and the amount of radioactivity released determined by scintillation counting.

Figure 5:
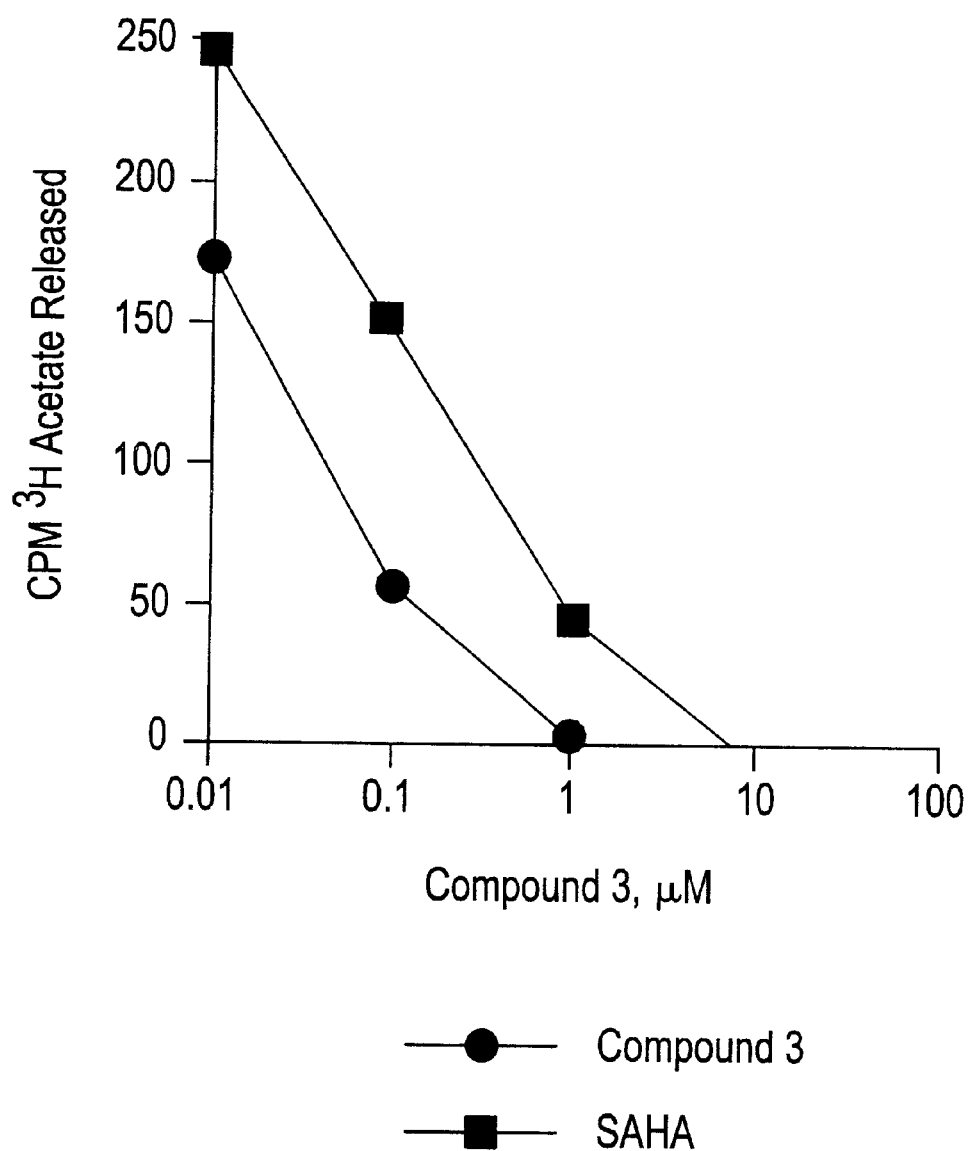
FIG. 5. The effect of Compound 3 according to the subject invention on Histone Deacetylase 1 activity.

It was observed, as shown in FIG. 5, that Compound 3 is a potent inhibitor of HDAC1 enzymatic activity ($ID_{50}$~100 nM)

EXAMPLE 10

Effect of Compound 4 (N-Benzyloxycarbonyl-(L)-α-aminoxuberoyl-8-quinolinamide-ω-hydroxamic Acid) on MEL Cell Differentiation and Histone Deacetylase Activity Murine Erythroleukemia (MEL) Cell Differentiation:

The MEL cell differentiation assay was used to assess the ability of Compound 4 to induce terminal differentiation. MEL cells (logarithmically dividing) were cultured with the indicated concentrations of Compound 4. Following a 5-day culture period differentiation was determined microscopically using the benzidine assay to determine hemoglobin protein accumulaiton on a per cell basis.

Figure 6:
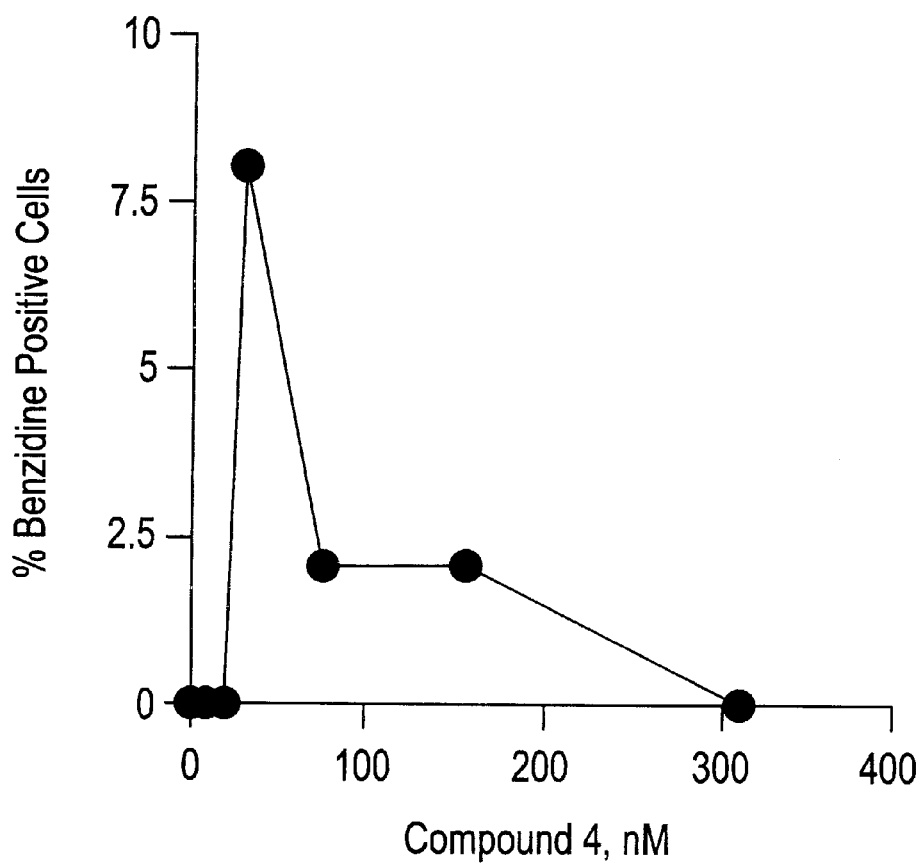
FIG. 6. The effect of Compound 4 according to the subject invention on MEL cell differentiation.

It was observed, as shown in FIG. 6, that Compound 4 (40 nM) is able to induce MEL cell differentiation.

Histone Deacetylase (HDAC) Enzymatic Activity:

The effect of Compound 4 on affinity purified human epitope-tagged (Flag) HDAC1 was assayed by incubating the enzyme preparation in the absence of substrate on ice for 20 min with indicated amounts of HPC. Substrate ([$^3$H] acetyl-labelled murine erythroleukemia cell-derived histone) was added and the samples were incubated for 20 min at 37° C. in a total volume of 30 μl. The reactions were then stopped and released acetate was extracted and the amount of radioactivity released determined by scintillation counting.

Figure 7:
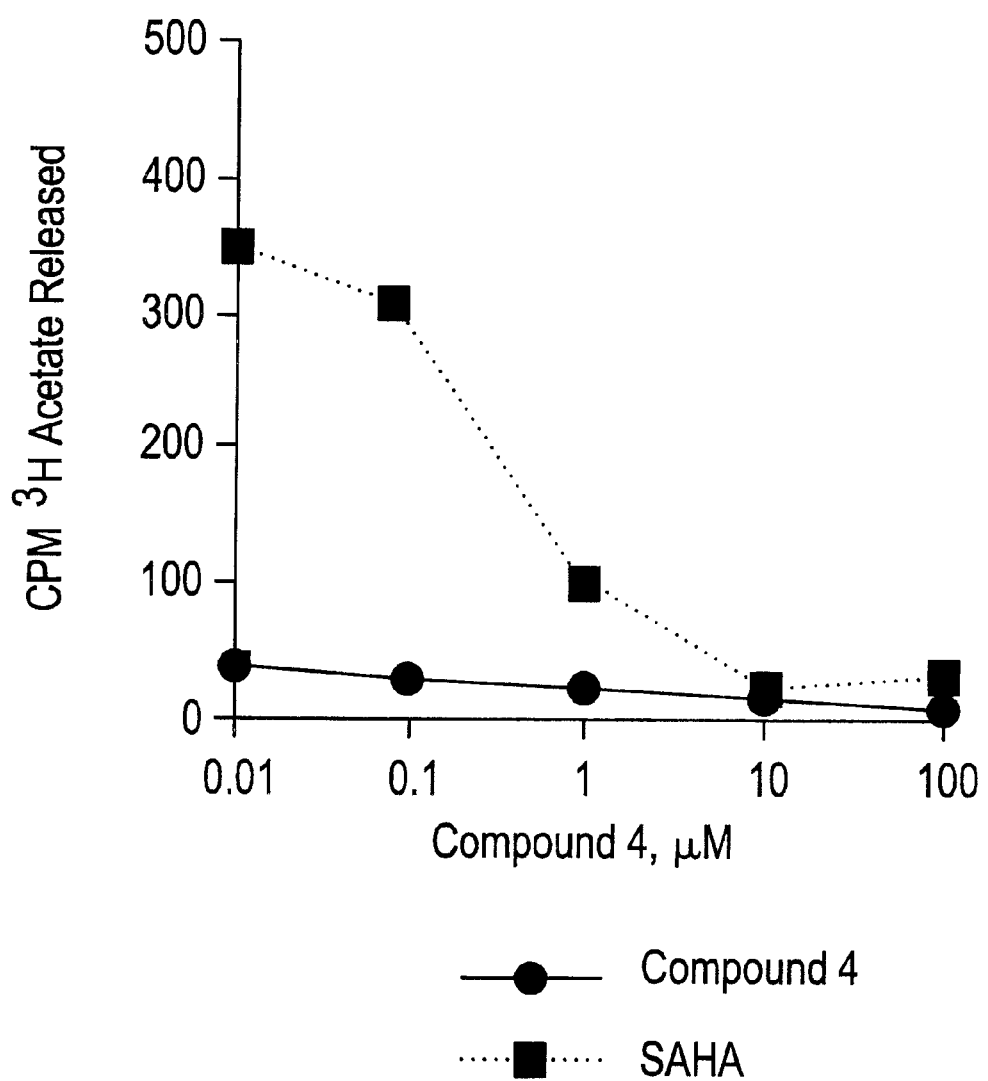
FIG. 7. The effect of Compound 4 according to the subject invention on Histone Deacetylase 1 activity.
Figure 8:
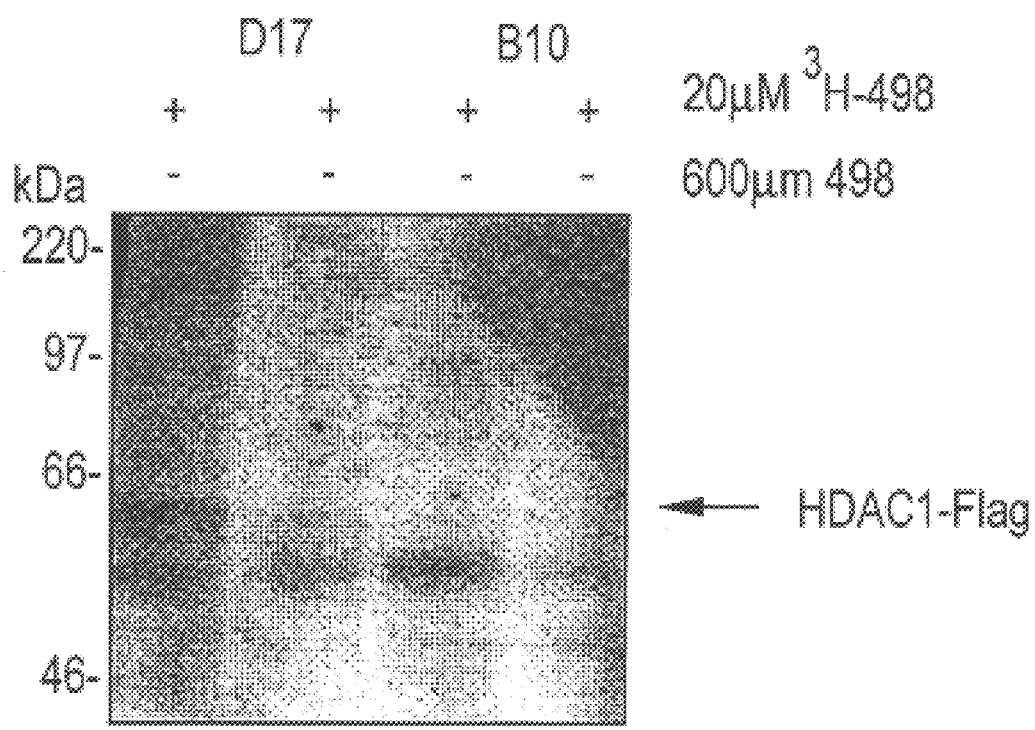
FIG. 8. A photoaffinity label (3H-498) binds directly to HDAC1.

It was observed, as shown in FIG. 7, that Compound 4 is a potent inhibitor of HDAC1 enzymatic activity ($ID_{50}$<10 nM). SAHA inhibits the activity of affinity purified HDAC1 and HDAC3 (39). Crystallographic studies with SAHA and a HDAC related protein reveal that SAHA inhibits HDAC by a direct interaction with the catalytic site (66). Additional studies demonstrate that a tritium labeled photoaffinity SAHA analog ($^3$H-498) that contains an azide moiety (67) binds directly to HDAC1 (FIG. 8). These results indicate that this class of hydroxamic acid based compound inhibits HDAC activity through a direct interaction with the HDAC protein.

Figure 9:
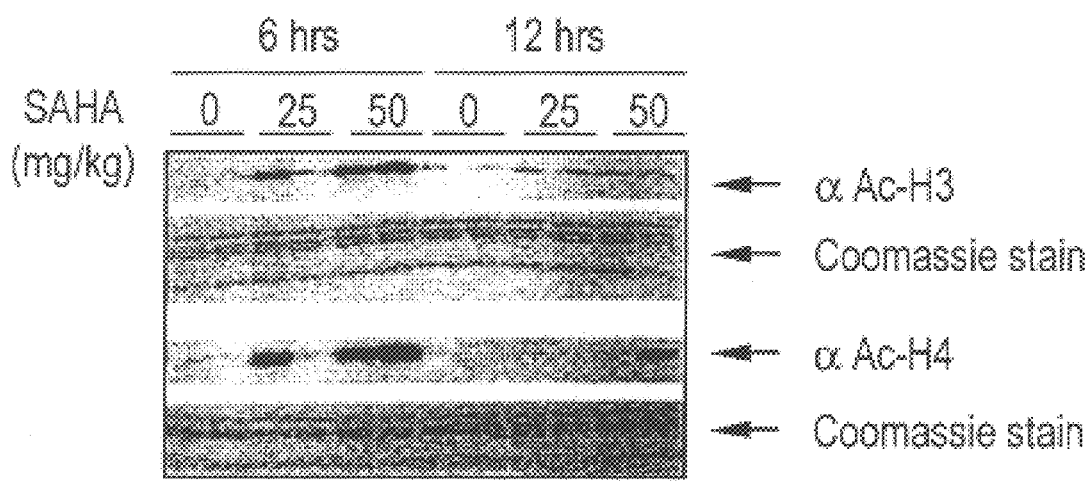
FIG. 9. SAHA causes accumulation of acetylated histones H3 and H4 in the CWR22 tumor xenograft in mice.

SAHA causes the accumulation of acetylated histones H3 and H4 in vivo. The in vivo effect of SAHA has been studied using the CWR22 human prostate xenograft in mice (68). SAHA (50 mg/kg/day) caused a 97% reduction in mean final tumor volume compared to controls with no apparent toxicity. SAHA administration at this dose caused an increase in acetylated histones H3 and H4 in the tumor xenograft (FIG. 9).

Figure 10:
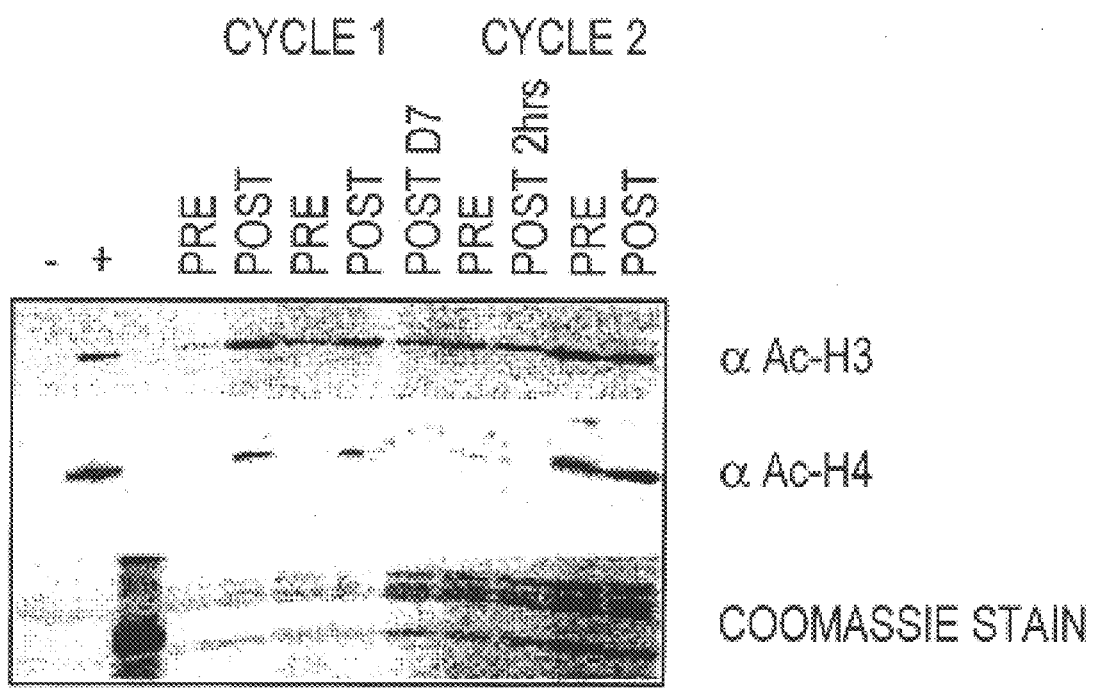
FIG. 10. SAHA causes accumulation of acetylation histones H3 and H4 in peripheral blood monnuclear cells in patients. SAHA was administered by IV infusion daily×3. Samples were isolated before (Pre), following infusion (Post) and 2 hours after infusion.
Figure 11A:
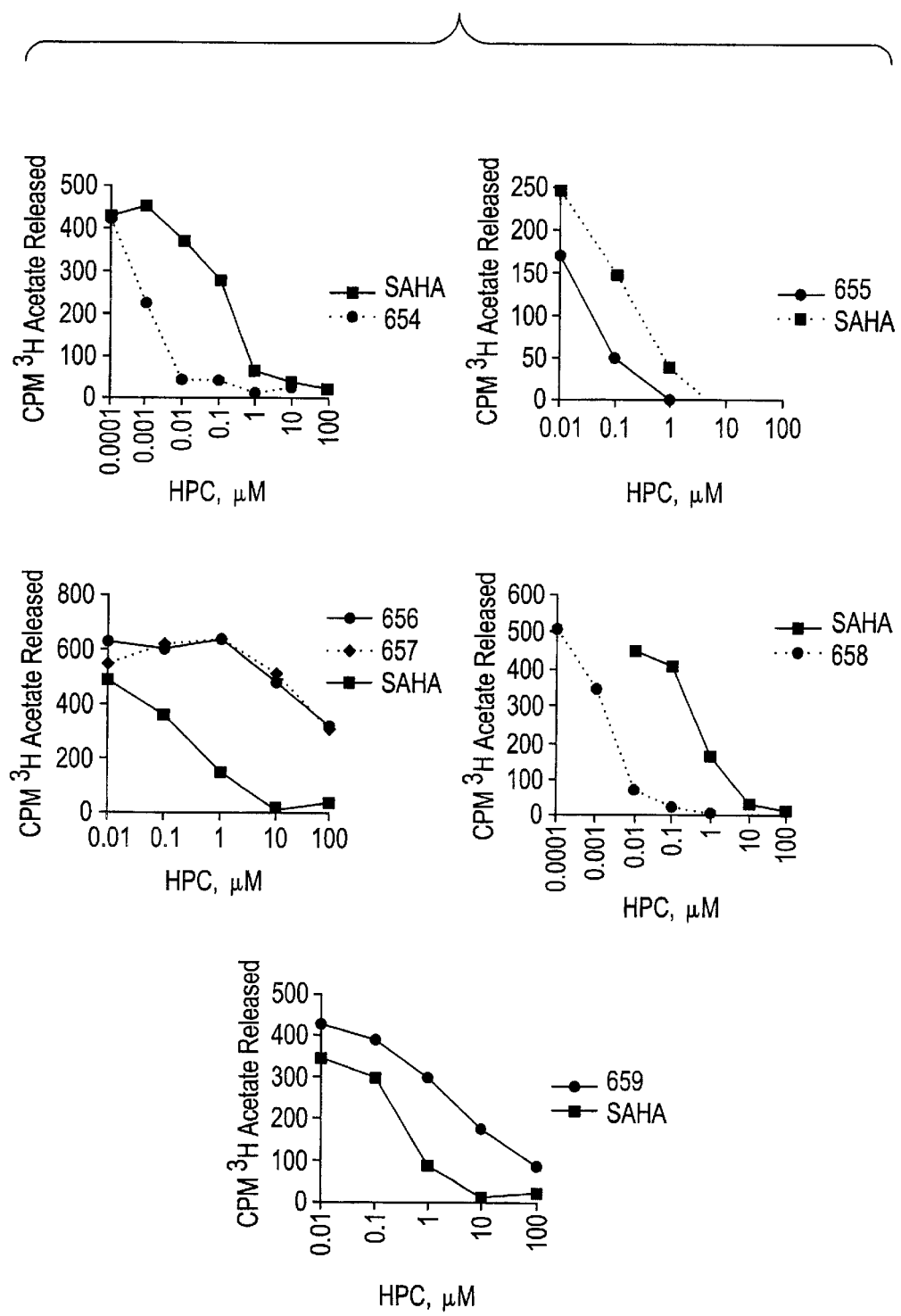
FIGS. 11a–11f. Show the effect of selected compounds on affinity purified human epitope-tagged (Flag) HDAC1.
Figure 11B:
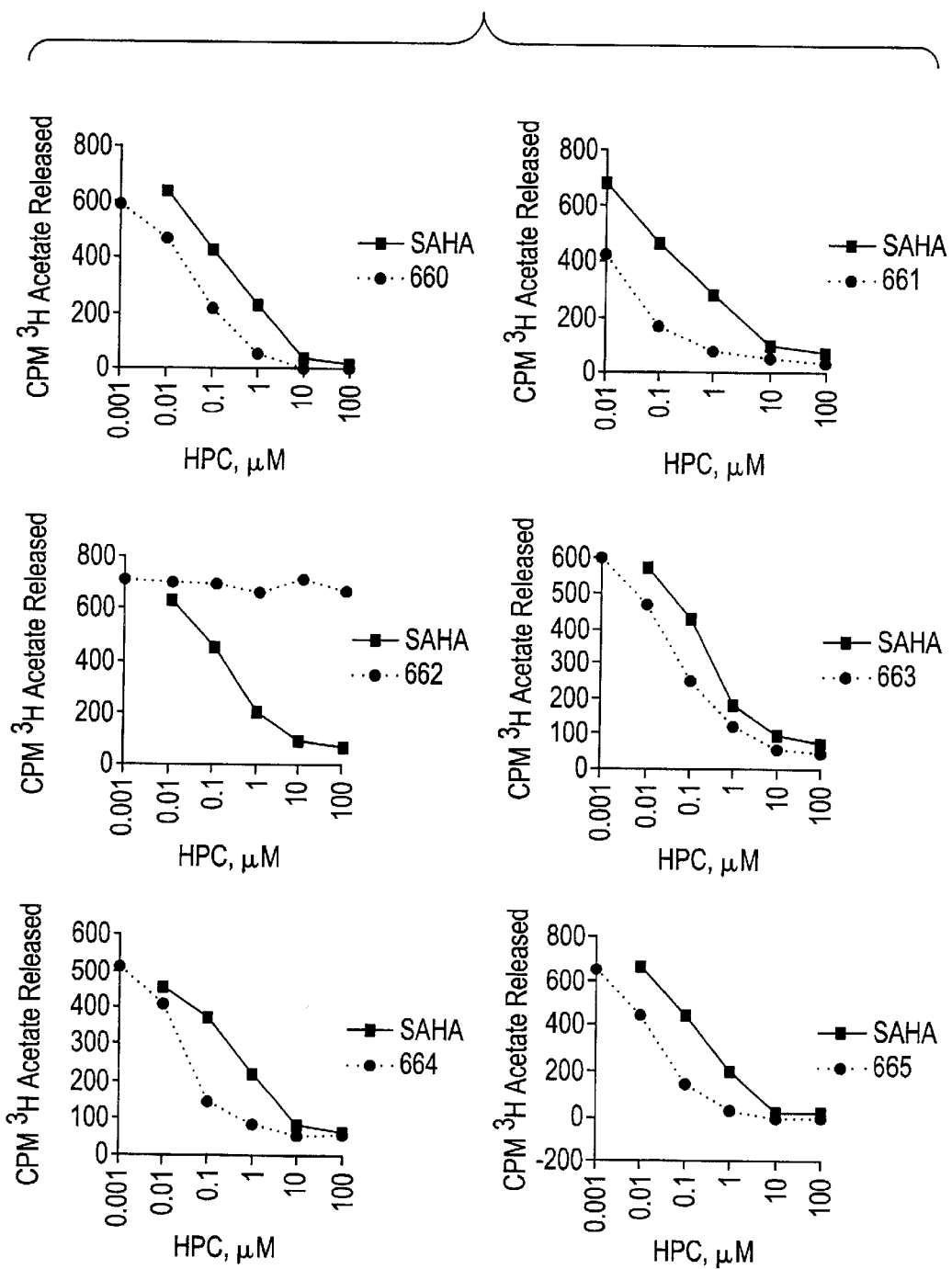
Figure 11C:
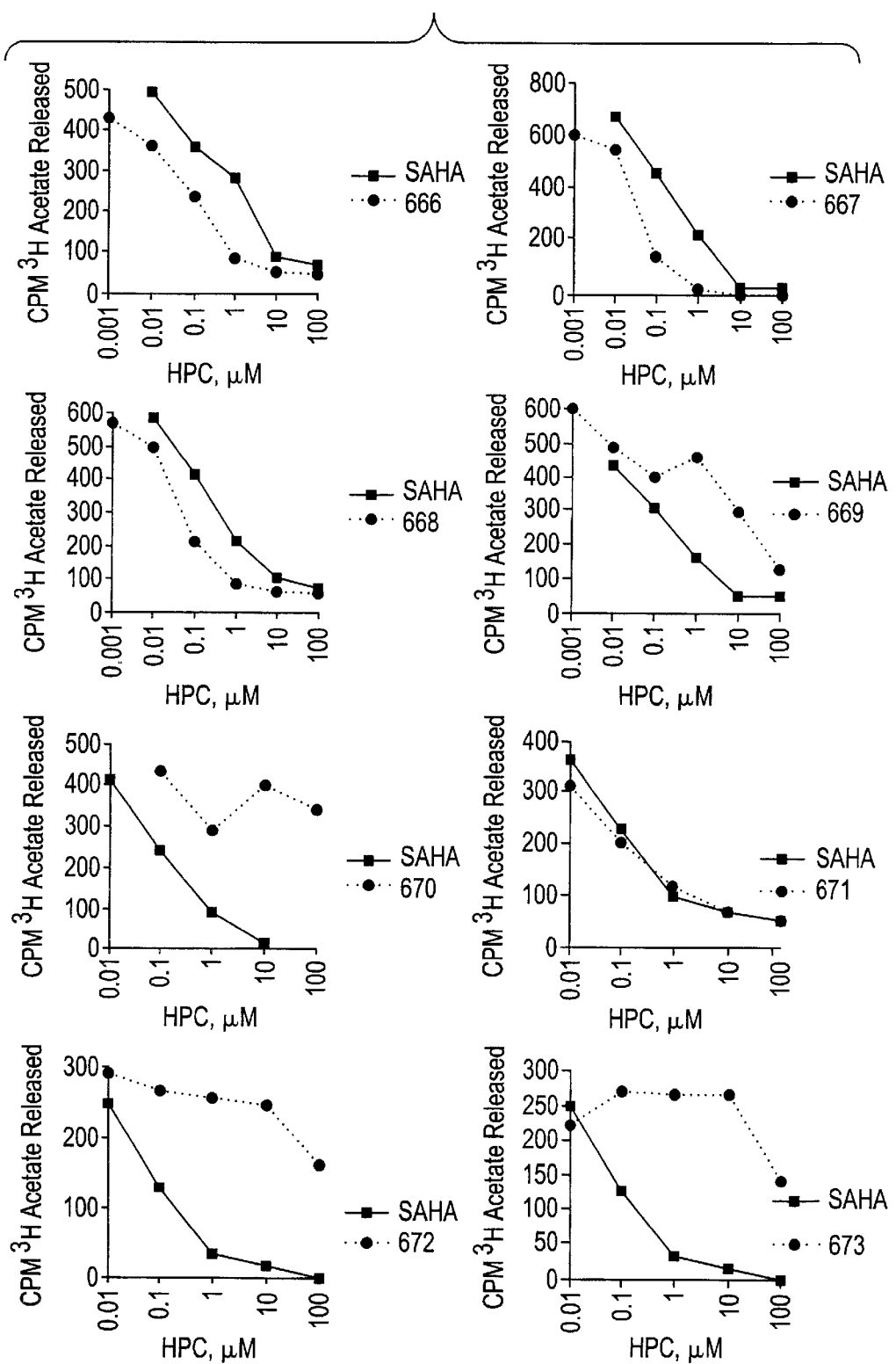
Figure 11D:
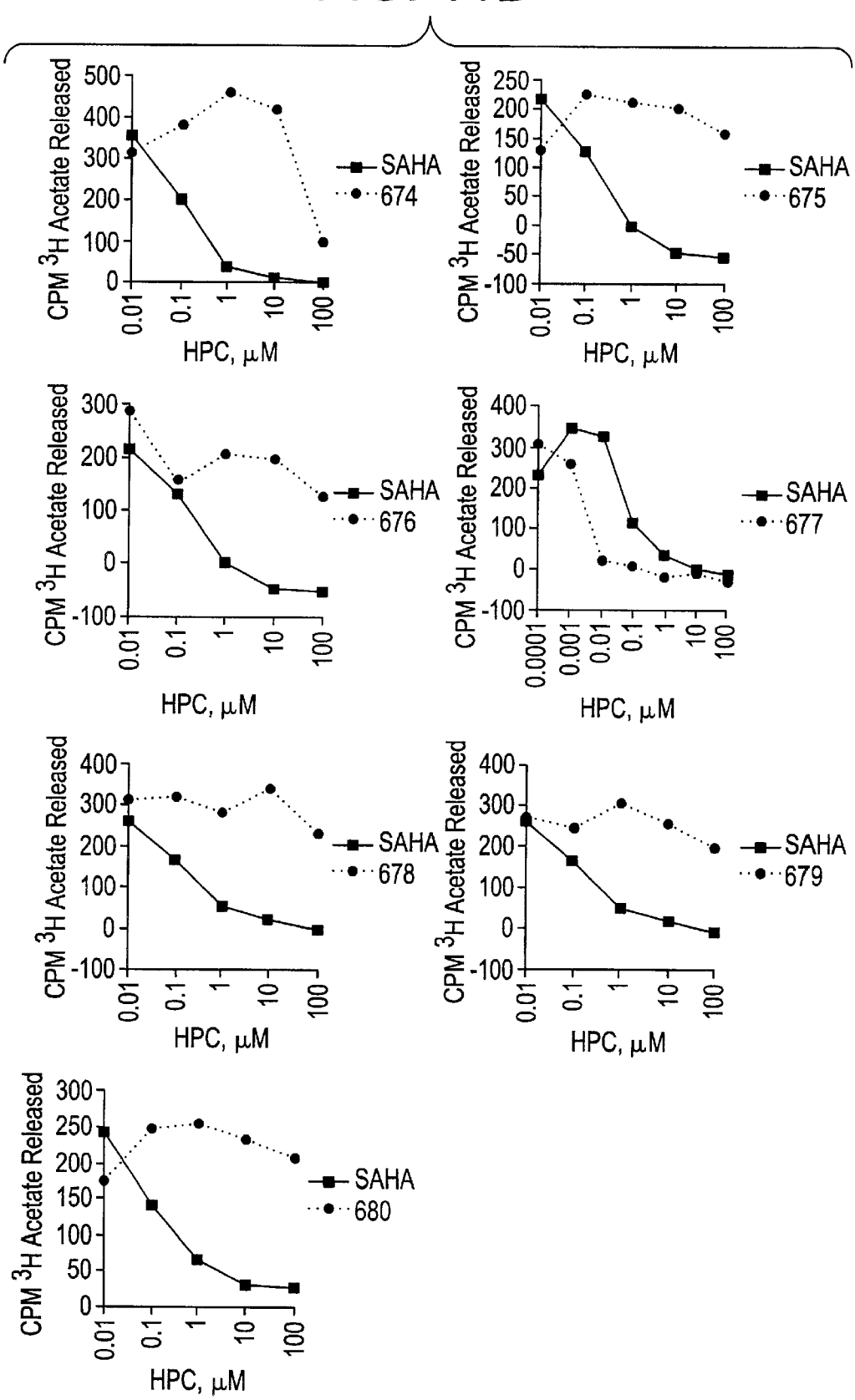
Figure 11E:
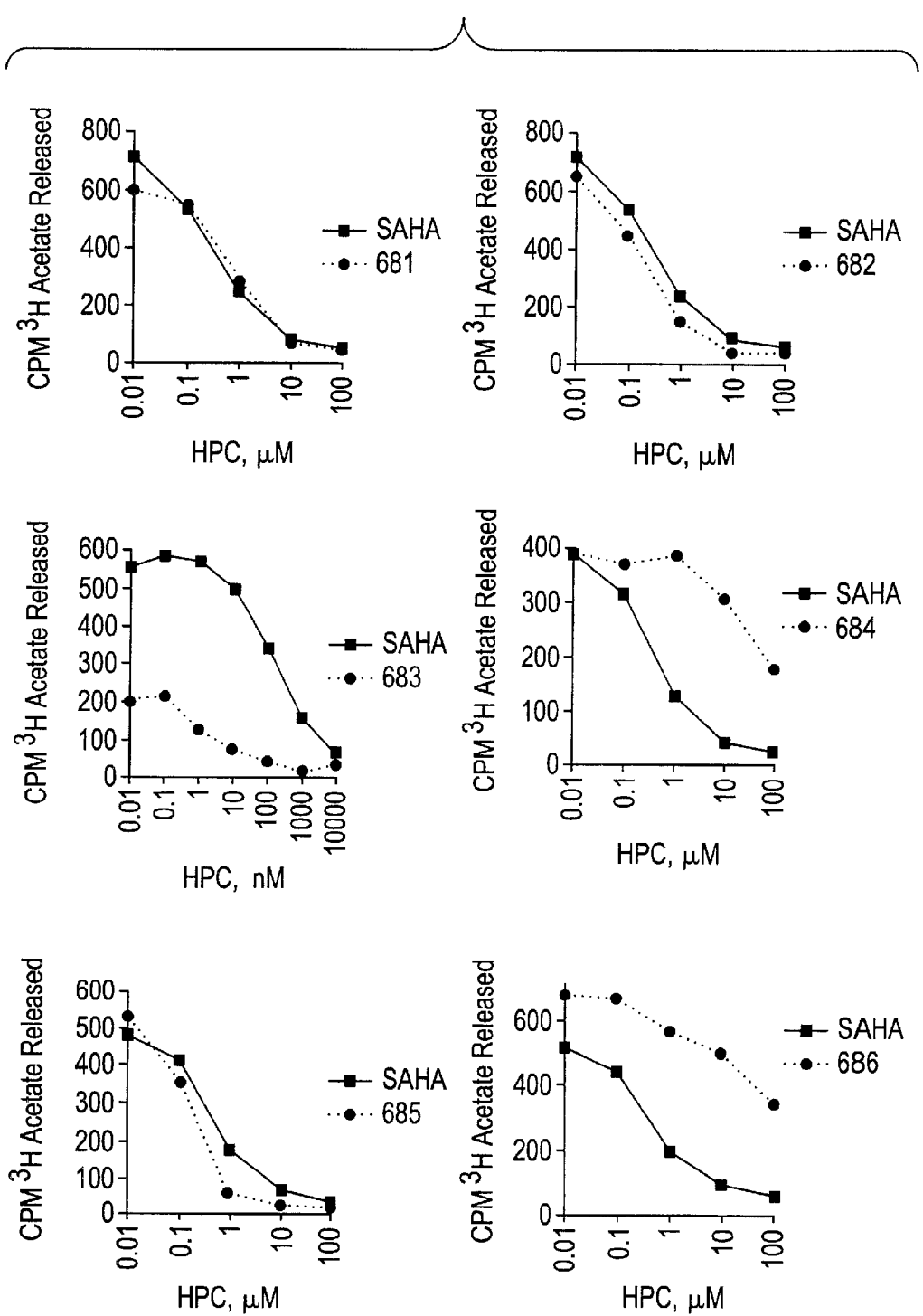
Figure 11F:
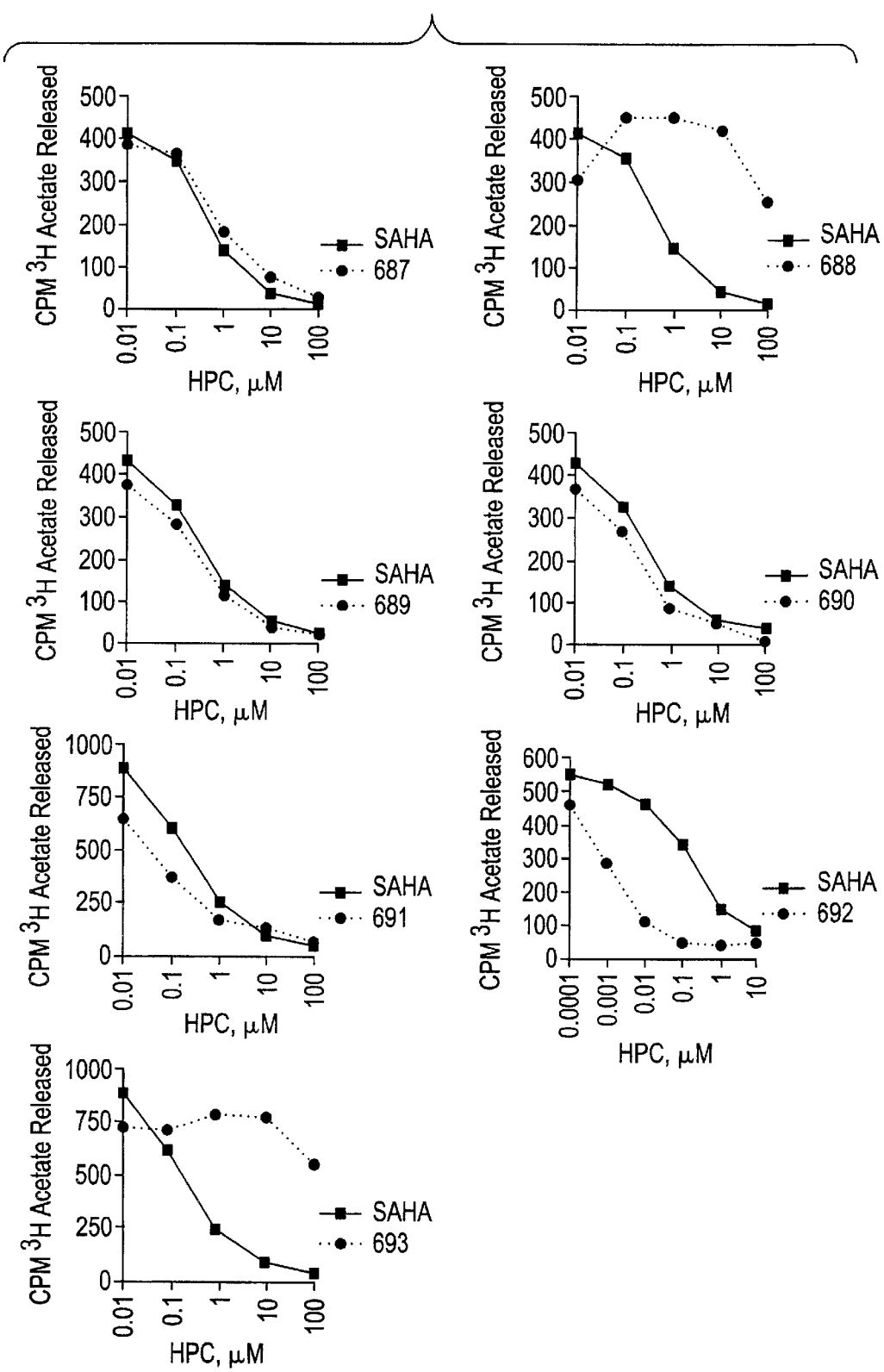

SAHA is currently in Phase I Clinical Trials in patients with solid tumors. SAHA causes an accumulation of acetylated histones H3 and H4 in the peripheral blood mononuclear cells isolated from patients undergoing treatment (FIG. 10).

Table 1 shows a summary of the results of the Examples 7–10, testing compounds 1–4, and also compares the results to the results obtained from using SAHA.

TABLE 1

Summary of Test results of compounds 1–4, and comparison to SAHA results.

| Com-pound | MEL Differentiation | | | HDAC Inhibition | |
|---|---|---|---|---|---|
| | Range | Opt. | % B+ | Range | ID50 |
| 1 | 0.1 to 50 μM | 200 nM | 44% | 0.0001 to 100 μM | 1 nM |
| 2 | 0.2 to 12.5 μM | 800 nM | 27% | | TBT |
| 3 | 0.1 to 50 μM | 400 nM | 16% | 0.01 to 100 μM | 100 nM |
| 4 | 0.01 to 50 μM | 40 nM | 8% | 0.01 to 100 μM | <10 nM |
| SAHA | | 2500 nM | 68% | 0.01 to 100 μM | 200 nM |

EXAMPLE 12

Modified Inhibitors of HDAC

In additional studies we found that compounds 6 and 7 shown below were very effective inhibitors of the enzyme HDAC. Compound 6 had $ID_{50}$ of 2.5 nM, and compound 7 had $ID_{50}$ of 50 nM.

This contrasts with an $ID_{50}$ for SAHA of 1 μM, much higher. Note that the 1 μM $ID_{50}$ for SAHA as an inhibitor of HDAC is of the same general magnitude as its 2.5 μM optimal dose for the cytodifferentiation of MEL cells, but this close similarity is not true for all the compounds examined. In some cases very effective HDAC inhibitors are less effective as cytodifferentiaters, probably because the drugs are metabolized in the cell assays. Also, all cell types are not the same, and some compounds are much better against human tumor cells such as HT-29 than they are against MEL cells. Thus, inhibition of HDAC cells is a preliminary indicator.

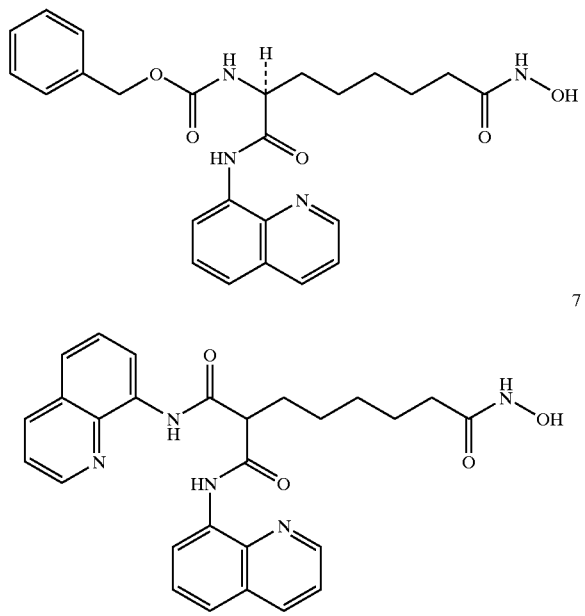

EXAMPLE 13

Evolution of Compounds without a Hydroxamic Acid Portion

Of the above compounds which are hydroxamic acids, we have found that they undergo enzymatic hydrolysis rather rapidly to the carboxylic acids, so their biological lifetimes are short. We were interested in evolving compounds which might be more stable in vivo. Thus we have developed inhibitors of HDAC that are not hydroxamic acids, and that can be used as cytodifferentiating agents with longer biological lifetimes. Furthermore, we found that the newly evolved compounds have better selectivity to HDAC than, e.g. SAHA.

We have evolved compounds that have double bonds, similarly to Trichostatin A (TSA) to see if the resulting compounds have even greater efficacy. Also, the chain in TSA is only five carbons, not the six of SAHA. In Oxamflatin there is a chain of four carbons containing a double bond and an ethinyl link between the hydroxamic acid and the first phenyl ring, and Oxamflatin has been claimed to be an effective inhibitor of HDAC. We incorporate some of these features in our compounds, including those compounds that are not hydroxamic acids.

Also disclosed are simple combinatorial methods for screening a variety of such compounds for efficacy and selectivity with respect to HDAC inhibition.

Furthermore, since there are many important enzymes that contain Zn(II), hydroxamic acids, and perhaps some of the other metal coordinating groups, can also bind to Zn(II) and other metals.

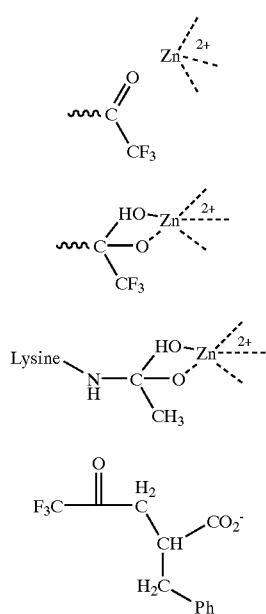

Since the target for HDAC is an acetyllysine sidechain of histone, we make compounds in which transition state analogs of the substrate are present. For example, we synthesize compounds like SAHA in which the hydroxamic acid group —CO—NHOH is replaced by a trifluoroacetyl group, —CO—CF$_3$. The resulting 8 will easily form a hydrate, and thus bind to the Zn(II) of HDAC as a mimic 9 of the transition state 10 for deacetylation. This is related to the work published by Lipscomb [56] on the binding to carboxypeptidase A of a substrate analog 11 containing a CF$_3$—CO—CH$_2$ group in place of the normal amide. The hydrate of the ketone coordinated to the Zn(II) as a mimic of the transition state for catalyzed hydrolysis of an amide substrate. Our synthesis of a particular example 12 in the fluoroketone series is shown in Scheme below:

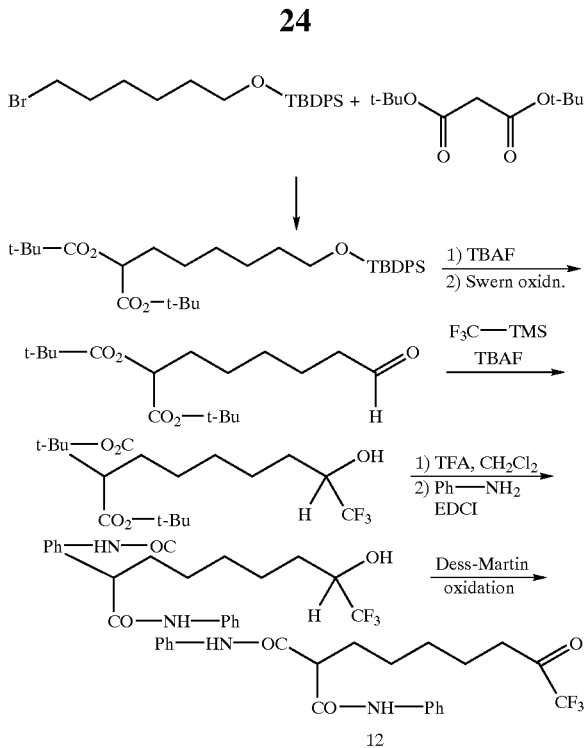

After the malonic ester alkylation, the aldehyde is prepared and then converted to the trifluoromethyl carbinol with Rupperts reagent [57, 58]. The malonic bis-anilides are prepared, and the carbinol oxidized to the ketone 12 with the Dess-Martin reagent [59]. Other approaches were tried unsuccessfully. In particular, attempts to convert a carboxylic acid derivative directly to a trifluoromethyl ketone did not work.

Compound 12 has been tested with HDAC and found to be an inhibitor of the enzyme. Thus, we also adapt this synthesis to the preparation of analogs of 12 with unsaturation, etc., in the chain, and other groups at the left end of the molecule.

EXAMPLE 14

Evolution of Compounds where the Hydroxamic Acid Group is Replaced by NH—P(O)OH—CH$_3$ An analog of SAHA in which the CH$_2$—CO—NHOH group is replaced by NH—P(O)OH—CH$_3$ may be synthesized by the general scheme shown below. The resulting compound, 13, binds to the Zn(II) of HDAC the way a related group binds to the Zn(II) of carboxypeptidase in analogs such as that prepared by Bartlett [60].

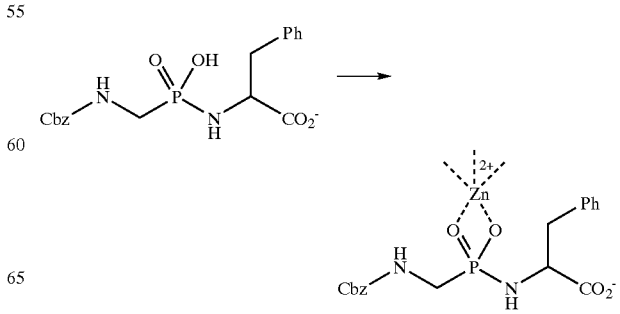

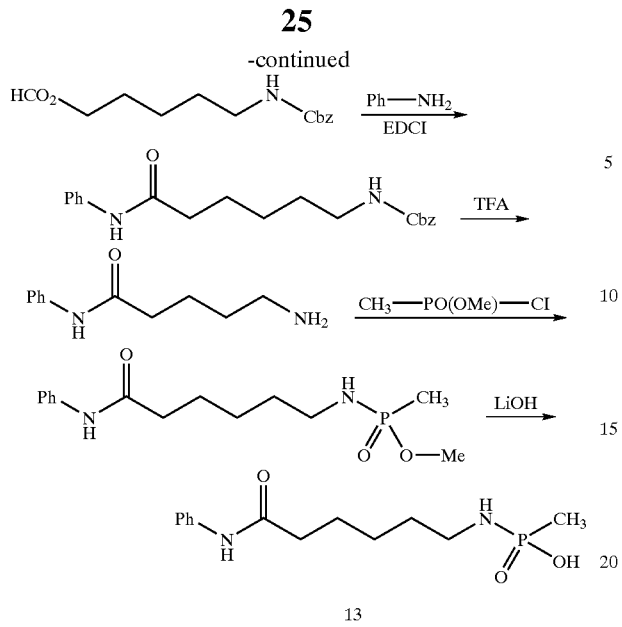

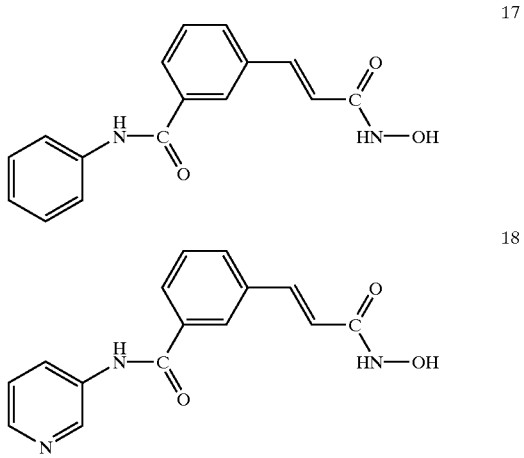

struct compounds 17 and 18. The simple syntheses, not shown in detail, only require that instead of the hydroxamic acid attached to the phenyl ring we make the aryl amides of 17 and 18.

Additional compounds may be synthesized, such as 19 and 20 to incorporate the trifluoromethyl ketone group of 12 that we know is effective as a Zn(II) binder in HDAC. The syntheses involve preparing compounds 21 and 22 and then adding $CF_3$ to form the carbinol, followed by oxidation as in the synthesis of 12. A simple synthesis involves Heck coupling of compounds 23 and 24 with ethyl acrylate, and conversion of the ester to aldehydes 21 and 22 by reduction to the carbinol and then reoxidation.

All the chains shown so far contain only carbon atoms, but thioether links may be acceptable and even useful, and they add synthetic ease. Thus, sulfonamides such as 25 and 26, related to 19 and 20, from the corresponding thiophenol and bromomethylsulfonamide. A related synthesis may be used to make the corresponding phosphonamidates 27 and 28, if this class proves to be useful HDAC inhibitors and cytodifferentiators. In this case, (N-protected) m-aminobenzoic acid is used to acylate the arylamines, then phosphorylate the anilino group.

A classic inhibitor of the Zn(II) enzyme carbonic anhydrase is a sulfonamide, whose anion binds to the Zn(II) [61]. Thus compound 14, an analog of SAHA with a sulfonamide group, is synthesized as shown below. In the last step we react a carboxylic sulfonic bis-chloride with aniline and ammonia. Since the carboxylic acid chloride reacts faster, we use the sequence of aniline, then ammonia, but the sequence may be reversed, or the mixture may be separated if the two are of similar reactivity.

In the course of the synthesis of 14, we use a thiol 15 easily made from the corresponding haloacid. Thiols are also inhibitors of Zn(II) enzymes such as carboxypeptidase A and related peptidases such as Angiotensin Converting Enzyme (ACE), so we convert 15 to 16 as an inhibitor of HDAC. A similar synthesis can be used to attach the $NH-P(O)OH-CH_3$ group to other compounds, in particular compounds 6 and 7.

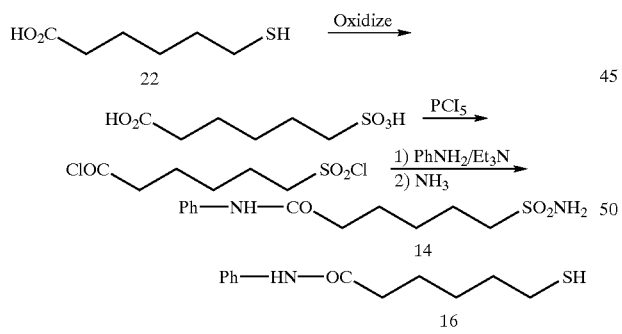

EXAMPLE 15

Varying the Linker Between the Zn(II) Binding Group and the Hydrophobic Binding Groups Based on the results with Oxamflatin, it seems that a phenyl ring can be part of the chain between the Zn(II) binding group and the left hand section of the molecule as drawn, particularly when the phenyl ring is meta substituted. Thus, we provide a synthesis to incorporate such meta substituted chains into other of our compounds. We con-

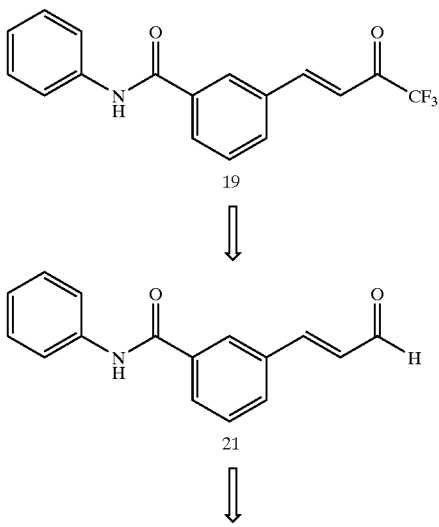

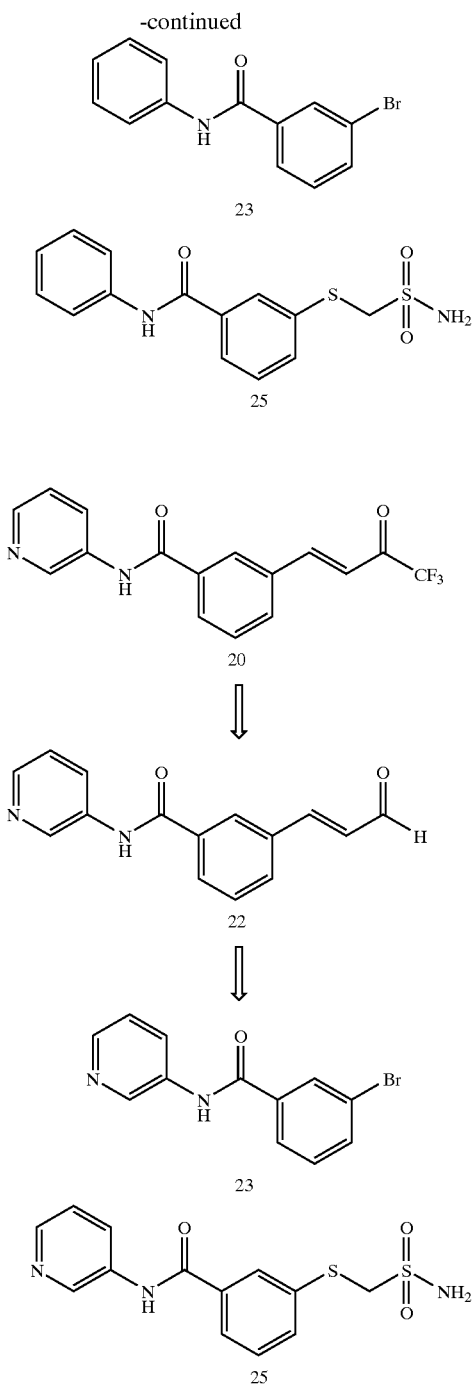

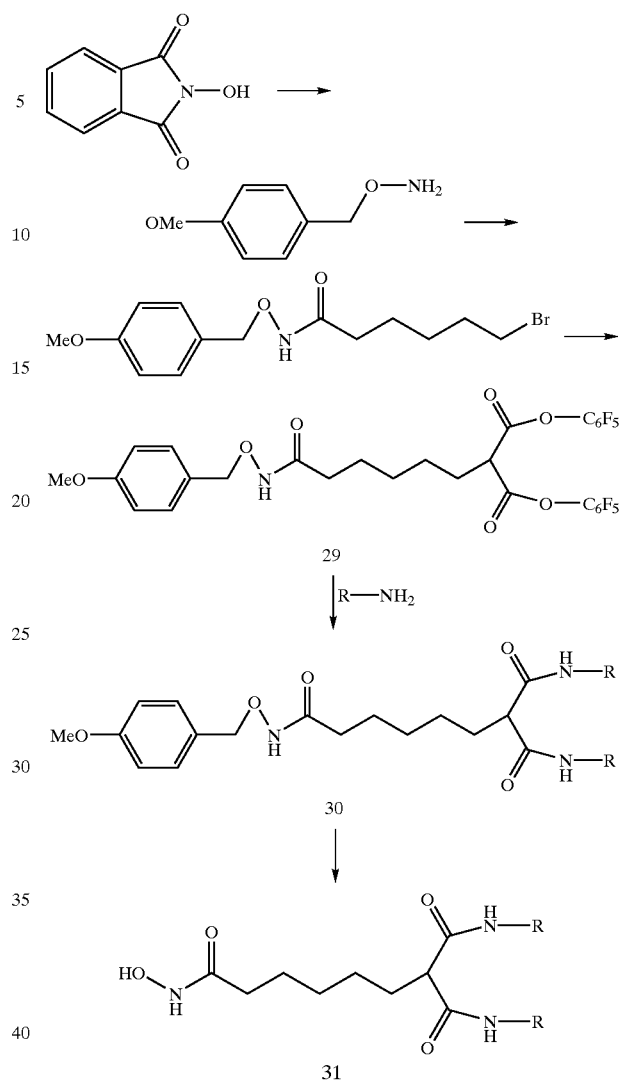

EXAMPLE 16

Varying the Left Hand of the Molecule, Carrying the Hydrophobic Groups

To vary the hydrophobic groups, we synthesized compound 29, as an intermediate that can be treated with various amines to make the compounds 30. Then deprotection of the hydroxamic acid group will generate the general class 31. The synthesis is shown in the scheme below.

In the synthesis the O-protected hydroxylamine is acylated with bromohexanoic acid, and the compound then alkylates the bis-pentafluoro ester of malonic acid. The resulting 29 then reacts with various amines, and the protecting group is removed with acid.

With this compound as the starting material, we synthesize related libraries carrying the other Zn(II) binding groups. For example, alkylation of the malonate with compound 32 lets us make a phosphonamidate library, and compound 33 will let us make a CF$_3$—CO library. In a similar way, a sulfonamide library can be made if the work described earlier indicates that this is a promising Zn(II) binding group for HDAC. Of course after malonate alkylation and aminolysis the compound from 32 will be demethylated, while that from 33 will be oxidized.

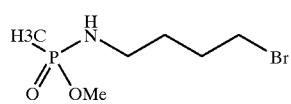

32

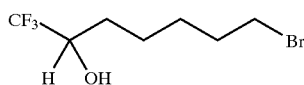

33

This also allows to expand on the structure of compound 6, the derivative of aminosuberic acid. As described, this was one of the most effective HDAC inhibitor we have examined. We prepared this compound using an enzymatic hydrolysis to achieve optical resolution and selectivity among the two carbomethoxy groups of 34, so that we could convert one of them to the aminoquinoline amide of 6 while protecting the nitrogen as a carbobenzoxy group. At the end of the synthesis we converted the remote carbomethoxy group to a hydroxamate. However, 6 is an intermediate that can be used to prepare other derivatives. The carbobenzoxy group from 6 can be removed and the amine 35 can acetylated with a variety of carboxylic acids to prepare library 36, or sulfonic acid chlorides to prepare the corresponding sulfonamides.

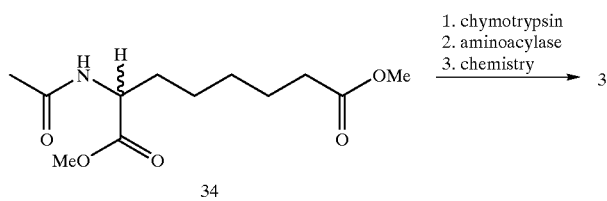

34

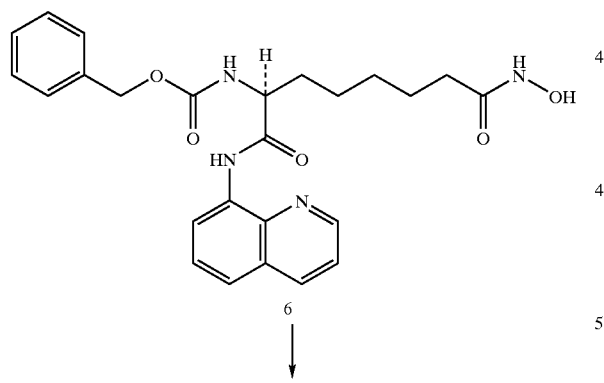

6

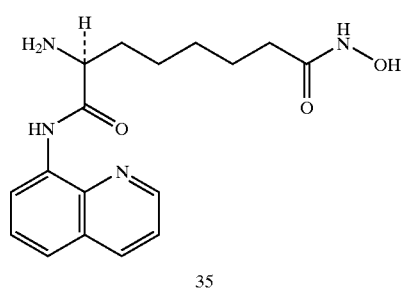

35

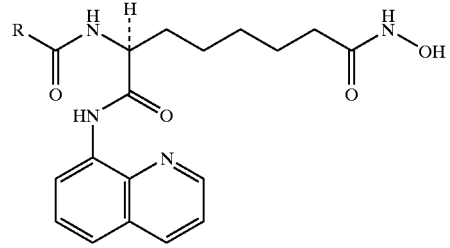

36

Also, we synthesize a different library of amides 37 related to 6, and then expand it with a library of other amides 38 by acylating the amino group after deprotection. We also synthesize a group of compounds 39 in which after the carbobenzoxy group of 37 is removed we make a library of sulfonamides using various sulfonyl chlorides. In all this, it the hydroxamic acid group may be protected.

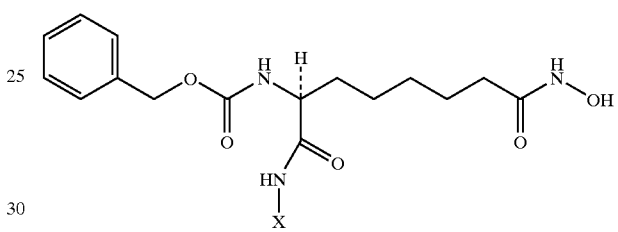

37

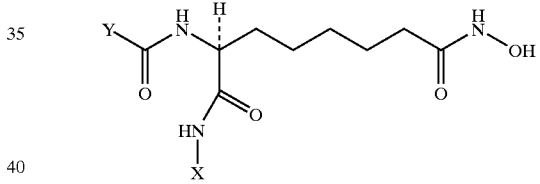

38

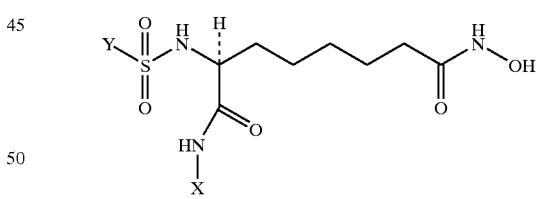

39

The foregoing synthesis schemes can be used to generate compounds having a large number of variation. Some substituent groups that are likely to result in compounds having potential good affinity to HDAC or having got differentiating activity are as follows:

Some Amines that can be Incorporated in Place of the Aniline in SAHA, or as the X Group in Compounds 37 and 38:

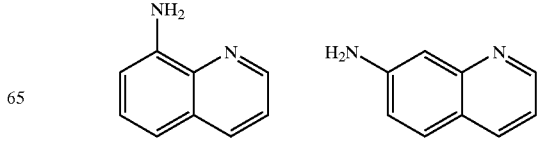

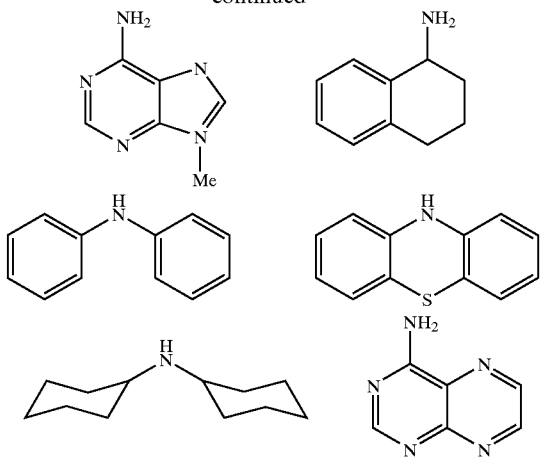

Some Carboxylic and Sulfonic Acids that can be Incorporated as Group Y—CO in Compound 38 or 39:

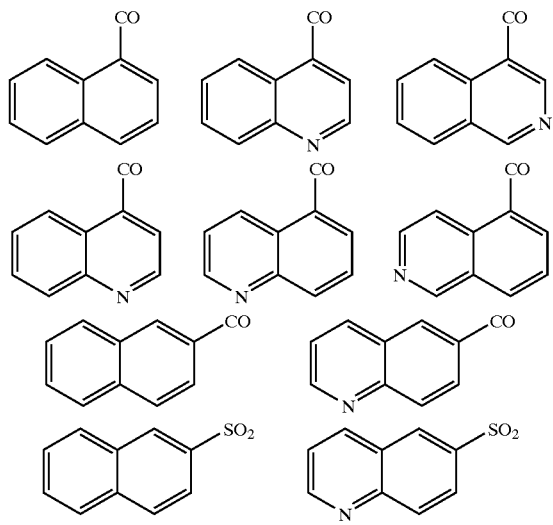

EXAMPLE 17

Synthesis using the Foregoing Schemes

Reagents and starting materials were obtained from commercial suppliers and used without further purification unless otherwise indicated. For moisture-sensitive reactions, solvents were freshly distilled prior to use: tetrahydrofuran was distilled under argon from sodium metal utilizing benzophenone as an indicator; dichloromethane and acetonitrile were distilled from powdered calcium hydride. Anhydrous benzene, anhydrous DIEA, and anhydrous pyridine were drawn by syringe from a sealed bottle purchased from Aldrich. tert-Butanol was dried over 4A molecular sieves before use. Sodium hydride was purchased as a 60% dispersion in mineral oil. Aniline, diisopropylamine, N-methylaniline, and benzyl alcohol were freshly distilled before use. Deuterated solvents were obtained from Cambridge Isotope Laboratories. Air- and/or moisture-sensitive reactions were carried out under an atmosphere of dry argon in oven- or flame-dried glassware equipped with a tightly-fitting rubber septum. Syringes and needles were oven-dried before use. Reactions at 0° C. were carried out in an ice/water bath. Reactions at −78° C. were carried out in a dry ice/acetone bath.

Chromatography

Analytical thin-layer chromatography (TLC) was conducted on glass plates precoated with silica gel 60 F-254, 0.25 mm thickness, manufactured by EM Science, Germany. Eluted compounds were visualized by one or more of the following: short-wave ultraviolet light, $I_2$ vapor, $KMnO_4$ stain, or $FeCl_3$ stain. Preparative TLC was carried out on Whatman precoated plates of either 500 μm or 1000 μm silica gel thickness. Flash column chromatography was performed on Merck Kieselgel 60, 230–400 mesh.

Instrumentation

NMR spectra were measured on Bruker DPX300 and DRX400 spectrometers; $^1H$ was observed at 300 and 400 MHz, and $^{19}F$ at 376 MHz. Chemical shifts are reported as δ values in ppm relative to the solvent residual peak. Mass spectra were obtained on a Nermag R-10-1 instrument for chemical ionization (CI) or electron impact ionization (EI) spectra, and on a Jeol JMS LCmate for electrospray ionization (ESI+) spectra. CI spectra were run with either ammonia ($NH_3$) or methane ($CH_4$) as the ionization gas.

(E,E)-7-t-Butoxycarbonyl-octa-2,4-dienedioic Acid 8-t-Butyl Ester 1-Methyl Ester (40)

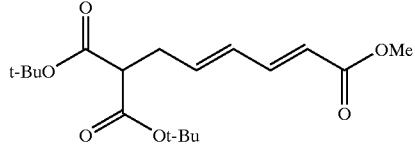

To a stirred solution of NaH (60% disp., 234 mg, 5.85 mmol) in THF (35 mL) at 0° C. was added di-t-butyl malonate (1.20 mL, 5.37 mmol) dropwise. Gas evolution was observed, and the solution was allowed to warm to ambient temperature and stirred for 6 h. A solution of methyl 6-bromo-2,4-hexadienoate (62) (1.00 g, 4.88 mmol) in THF (20 mL) was prepared in a separate flask and stirred in a water bath. To this was cannulated dropwise the malonate mixture, and the reaction allowed to proceed overnight. The reaction was quenched with sat. $NH_4Cl$ (5 mL), then $H_2O$ (10 mL) was added and the mixture extracted with $Et_2O$ (3×15 mL). The organic fractions were combined and washed with $H_2O$ (1×10 mL), then with brine, dried over $MgSO_4$, and filtered. Evaporation under reduced pressure followed by flash chromatography (0–20% EtOAc/hexanes) gave 40 as a clear colorless oil (850 mg, 2.49 mmol, 51%). TLC $R_f$ 0.66 (20% EtOAc/hexanes); $^1$H-NMR ($CDCl_3$, 400 MHz) δ 7.26 (dd, 1H), 6.26 (dd, 1H), 6.10 (m, 1H), 5.82 (d, 1H), 3.78 (s, 3H), 3.12 (t, 1H), 2.64 (t, 2H), 1.41 (s, 18H).

(E,E)-7-Carboxy-octa-2,4-dienedioic Acid 1-Methyl Ester (41)

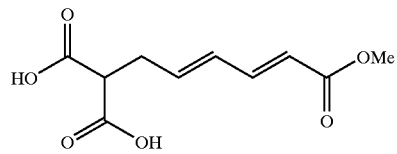

To a stirred solution of 40 (200 mg, 0.59 mmol) in $CH_2Cl_2$ (10 mL) was added TFA (1 mL). The reaction was allowed to proceed overnight. Volatiles were removed under reduced pressure to leave 41 as a white solid (112 mg, 0.49 mmol, 83%). $^1$H-NMR ($CD_3OD$, 400 MHz) δ 7.11 (dd, 1H), 6.33 (dd, 1H), 6.16 (m, 1H), 5.81 (d, 1H), 3.76 (s, 3H), 3.15 (t, 1H), 2.70 (t, 2H).

4-Pentenoic Acid Phenylamide (42)

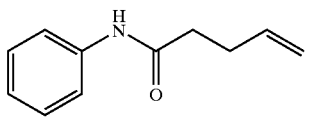

To a stirred solution of oxalyl chloride (2.0 M in $CH_2Cl_2$, 11.5 mL, 23.1 mmol) in $CH_2Cl_2$ (100 mL) and DMF (1 drop) at 0° C. was added 4-pentenoic acid (2.25 mL, 22.0 mmol). This was allowed to warm to ambient temperature. Upon cessation of gas evolution, the mixture was returned to 0° C. and a solution of aniline (2.00 mL, 22.0 mmol) and TEA (6.72 mL, 26.3 mmol) in $CH_2Cl_2$ (5 mL) was added dropwise. After warming to ambient temperature, the reaction was allowed to proceed for 3 h. The mixture was concentrated under reduced pressure, and then partitioned between HCl (1 N, 10 mL) and EtOAc (30 mL) and the layers separated. The aqueous portion was extracted with EtOAc (3×15 mL) and the organic layers combined, washed with brine, dried over $MgSO_4$, and filtered. Concentration under reduced pressure gave a yellowish solid, which was recrystallized with toluene to obtain 42 as white crystals (1.97 g, 11.24 mmol, 51%). TLC $R_f$ 0.68 (50% EtOAc/hexanes); $^1$H-NMR (300 MHz, $CDCl_3$) δ 7.49 (d, 2H), 7.29 (t, 2H), 7.08 (t, 1H), 5.88 (m, 1H), 5.10 (dd, 2 H), 4.42 (br s, 4 H).

(E,E)-Octa-2,4-dienedioic Acid 8-t-Butyl Ester 1-Methyl Ester (43)

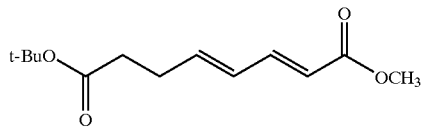

To a stirred solution of diisopropylamine (2.06 mL, 14.7 mmol) in THF (25 mL) at −78° C. was added n-BuLi (2.0 M in hexanes, 6.2 mL, 12.4 mmol) and allowed to stir 20 min at this temperature. A solution of phosphonate 43a (63) (2.66 g, 11.3 mmol) in THF (4 mL) was then added dropwise, giving a deep yellow color upon addition. After 20 min at −78° C., the mixture was warmed to 0° C. and a solution of aldehyde 43b (64) (1.78 g, 11.3 mmol) in THF (4 mL) was added dropwise. After addition the solution was allowed to warm to ambient temperature and stirred overnight. It was diluted with $Et_2O$ (30 mL) and washed with $H_2O$ (3×10 mL). The aqueous washings were combined and extracted with $Et_2O$ (2×10 mL), and the organic portions combined, washed with brine, dried over $MgSO_4$, and filtered. Evaporation under reduced pressure followed by flash chromatography (10–20% EtOAc/hexanes) gave 43 as a clear oil (1.54 g, 57%). TLC $R_f$ 0.56 (20% EtOAc/hexanes); $^1$H-NMR (400 MHz, $CDCl_3$) δ 7.22 (dd, 1H), 6.19 (dd, 1H), 6.08 (m, 1H), 5.77 (d, 1H), 2.42 (m, 2H), 2.32 (t, 2H), 1.42 (s, 9H).

(E,E)-7-Phenylcarbamoyl-hepta-2,4-dienoic Acid Methyl Ester (44)

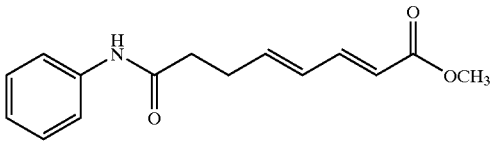

To a stirred solution of diester 43 (1.00 g, 4.61 mmol) in $CH_2Cl_2$ (40 mL) was added TFA (4.0 mL) and let react for 6 h. The mixture was concentrated under reduced pressure to remove volatiles. A white solid consisting of the crude acid (710 mg, 3.85 mmol) remained. This acid (400 mg, 2.17 mmol) was dissolved in $CH_2Cl_2$ (20 mL) and to this stirred solution were added DMAP (13 mg), aniline (218 μL, 2.39 mmol), and EDC (500 mg, 2.61 mmol). After 1.5 h, the mixture was diluted with EtOAc and washed with $H_2O$. The layers were separated, and the aqueous extracted with EtOAc (3×15 mL). The organic portions were combined and washed with HCl (1 N, 1×5 mL) and brine, dried over $MgSO_4$, and filtered. Concentration under reduced pressure left a brown solid. This was dissolved in a minimum of $CH_2Cl_2$, then passed through a plug of silica gel (20–30% EtOAc/hexanes, 200 mL) to remove baseline impurities. The eluent was concentrated to a light brown oil which was taken up in a small amount of $CH_2Cl_2$ and from which crystals were precipitated up6n the addition of hexanes/diethyl ether. The mother liquor was drawn off, the crystals rinsed with ether, and the liquid fraction concentrated and this procedure repeated several times to ultimately give 44 as off-white crystals (324 mg, 1.25 mmol, 58%). TLC $R_f$ 0.44 (50% EtOAc/hexanes); $^1$H-NMR (400 MHz, $CDCl_3$) δ 7.47 (d, 1H), 7.30 (t, 2H), 7.24 (m, 1H), 7.09 (t, 1H), 6.24 (dd, 1H), 6.14 (m, 1H), 5.81 (d, 1H), 3.72 (s, 3H), 2.60 (m, 2H), 2.47 (t, 2H).

(E,E)-7-(Methyl-phenyl-carbamoyl)-hepta-2,4-dienoic Acid Methyl Ester (45)

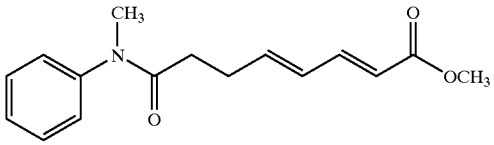

The crude acid intermediate from the first step of the preparation of 44 (200 mg, 1.09 mmol) and N-methylaniline (130 μL, 1.19 mmol) were dissolved in $CH_2Cl_2$ (10 mL) and stirred. EDC (271 mg, 1.41 mmol) and DMAP (5 mg) were then added and the reaction run overnight. The mixture was partitioned between $H_2O$ and EtOAc and the layers separated. The aqueous layer was extracted with EtOAc (3×10 mL), the organic portions combined and washed with HCl (1 N, 1×5 mL), then brine, dried over $MgSO_4$, and filtered. Evaporation under reduced pressure left pure 45 as a brown oil (286 mg, 1.05 mmol, 96%). TLC $R_f$ 0. 81 (5% MeOH/$CH_2Cl_2$); $^1$H-NMR (300 MHz, $CDCl_3$) δ 7.40 (t, 2H), 7.35 (t, 1H), 7.20 (d, 2H), 7.15 (dd, 1H), 6.20 (m, 2H), 5.76 (d, 1H), 3.70 (s, 3H), 3.24 (s, 3H), 2.42 (m, 2H), 2.18 (t, 2H).

(E,E)-7-Phenylcarbamoyl-hepta-2,4-dienoic Acid (46)

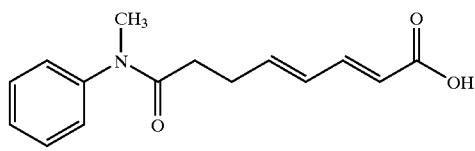

Ester 45 (260 mg, 0.95 mmol) was dissolved in MeOH (7.5 mL). A solution of LiOH.H$_2$O (200 mg, 4.76 mmol) in H$_2$O (2.5 mL) was then added and the mixture stirred for 6 h. The reaction was acidifed with HCl (1 N) until pH 2 and then extracted with EtOAc (3×10 mL). The organic fractions were combined and washed with H$_2$O and brine, dried over MgSO$_4$, and filtered. Evaporation under reduced pressure left the product pure 46 as a brown solid (200 mg, 0.77 mmol, 81%). TLC R$_f$ 0.13 (40% EtOAc/hexanes); $^1$H-NMR (300 MHz, CD$_3$OD) δ 7.47 (t, 2H), 7.41 (d, 1H), 7.28 (d, 2H), 7.19 (dd, 1H), 6.18 (dd, 1H), 6.05 (m, 1H), 3.27 (s, 3H), 3.40 (m, 2H), 2.22 (t, 2H).

(E,E)-Octa-2,4-dienedioic Acid 1-Hydroxyamide 8-Phenylamide (47)

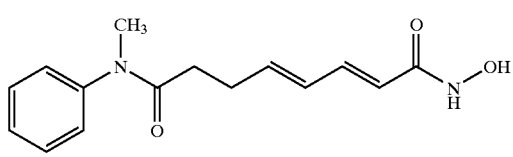

Acid 46 (200 mg, 0.77 mmol) and TBDPSO-NH$_2$ (220 mg, 0.81 mmol) were dissolved in CH$_2$Cl$_2$ (8 mL). To this stirred solution were added EDC (178 mg, 0.93 mmol) and DMAP (5 mg) and the reaction allowed to proceed overnight. The mixture was concentrated and then passed through a plug of silica gel (EtOAc). Evaporation under reduced pressure left a light brown oil (383 mg, 0.75 mmol, 97%). The protected hydroxamate (270 mg, 0.53 mmol) was dissolved in CH$_2$Cl$_2$ (10 mL) and TFA was added (0.5 mL). The solution was stirred for 2 h, and a new spot on TLC was observed which stained with FeCl$_3$. The solution was concentrated under reduced pressure and diethyl ether added, giving a residue which adhered to the flask. The liquid phase was drawn off, the residue was triturated with EtOAc, the liquid removed, and evaporation of all volatiles from the residue gave 47 as a brown gum (23 mg, 0.084 mmol, 16%). TLC R$_f$ 0.22 (5% MeOH/CH$_2$Cl$_2$); $^1$H-NMR (400 MHz, CD$_3$OD) δ 7.50 (t, 2H), 7.40 (t, 1H), 2.27 (d, 2H), 7.08 (m, 1H), 6.11 (m, 1H), 5.97 (m, 1H), 5.80 (m, 1H), 3.23 (s, 3H), 3.39 (m, 2H), 2.21 (t, 2H).

Octanedioic Acid Hydroxyamide Phenylamide (48)

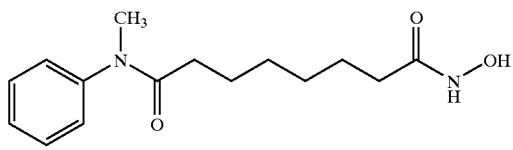

The title compound 48 was obtained as a brown gum (9 mg) by a series of steps analogous to the preparation of 47. TLC R$_f$ 0.20 (5% MeOH/CH$_2$Cl$_2$); $^1$H-NMR (400 MHz, CD$_3$OD) δ 7.51 (t, 2H), 7.41 (t, 1H), 7.30 (d, 2H), 3.29 (s, 3H), 2.11 (m, 4H), 1.58 (m, 4H), 1.22 (m, 4H).

Octanedioic Acid Benzylamide (49)

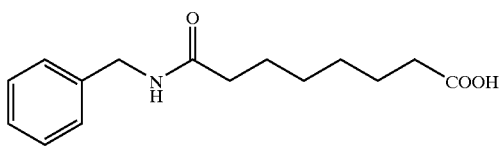

To a stirred solution of suberoyl chloride (1.00 mL, 5.55 mmol) in THF (40 mL) at 0° C. was added a solution of benzylamine (0.61 mL, 5.55 mmol) and DIEA (1.45 mL, 8.33 mmol) in THF (10 mL) dropwise. The mixture was allowed to warm to ambient temperature and stirred for 1 h. Then, HCl (10 mL, 1 N) was added and the mixture stirred for 0.5 h. The contents were diluted with EtOAc (30 mL) and the layers separated. The aqueous portion was extracted with EtOAc (3×10 mL), the organics combined, washed with brine (5 mL), and dried over MgSO$_4$. Filtration and concentration under reduced pressure left 49 as an off-white solid. $^1$H-NMR (300 MHz, DMSO-d$_6$) δ 11.98 (br s, 1H), 9.80 (t, 1H), 7.32 (m, 2H), 7.23 (m, 3H), 4.25 (d, 2H), 2.19 (t, 2H), 2.12 (t, 2H), 1.50 (m, 4H), 1.25 (m, 4H).

Octanedioic Acid Benzylamide Hydroxyamide (50)

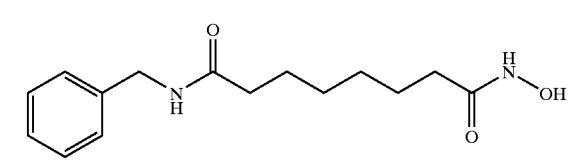

This compound was prepared from 49 through its protected hydroxamate as described for earlier compounds. Obtained 50 as a white solid. $^1$H-NMR (400 MHz, DMSO-d$_6$) δ 10.30 (s, 1H), 8.27 (t, 1H), 7.28 (m, 2H), 7.23 (m, 3H), 5.65 (d, 2H), 2.11 (t, 2H), 1.91 (t, 2H), 1.46 (m, 4H), 1.23 (m, 4H).

(7S)-7-Benzyloxycarbonylamino-7-phenylcarbamoyl-heptanoic Acid t-Butyl Ester (51)

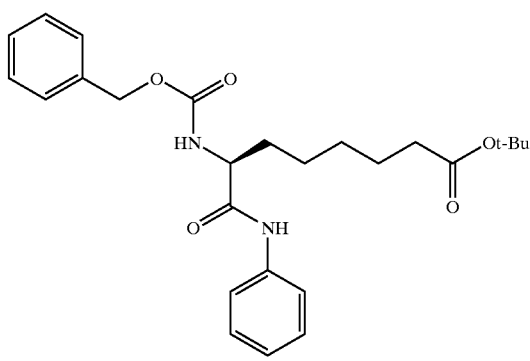

N-Cbz-L-2-aminosuberic acid 8-t-butyl ester, dicyclohexylamine salt (100 mg, 0.18 mmol) was dissolved in HCl (5 mL, 1 N) and extracted with EtOAc (3×10 mL). The extracts were combined, washed with brine, and dried over MgSO$_4$. Evaporation left the free acid as a white solid (68 mg, 0.179 mmol). This was dissolved in CH$_2$Cl$_2$ (2.5 mL), to which were added aniline (17 µL, 0.19 mmol), DIEA (46 µL, 0.27 mmol), and finally Py.BOP (97 mg, 0.19 mmol). The solution was stirred for 1 h, then concentrated, and the residue partitioned between H$_2$O (5 mL) and EtOAc (10 mL). The layers were separated, and the aqueous portion extracted with EtOAc (3×10 mL). The extracts were pooled and washed with HCl (1 N), then brine, dried over MgSO$_4$, and filtered. Concentration under reduced pressure gave a solid residue which was passed through a plug of silica gel (30% EtOAc/hexanes). The collected eluent was evaporated to give 51 as a white solid (76 mg, 0.167 mmol, 94%). TLC R$_f$ 0.38 (30% EtOAc/hexanes); $^1$H-NMR (400 MHz, CDCl$_3$) δ 8.21 (s, 1H), 7.48 (d, 2H), 7.32 (m, 5H), 7.28 (t, 2H), 7.08 (t, 1H), 5.39 (br d, 1H), 5.10 (m, 2H), 4.26 (br dd, 1H), 2.07 (t, 2H), 1.92 (m, 1H), 1.66 (m, 1H), 1.55 (m, 2H), 1.42 (s, 9H), 1.38 (m, 4H).

(7S)-7-Benzyloxycarbonylamino-7-phenylcarbamoyl-heptanoic Acid (52)

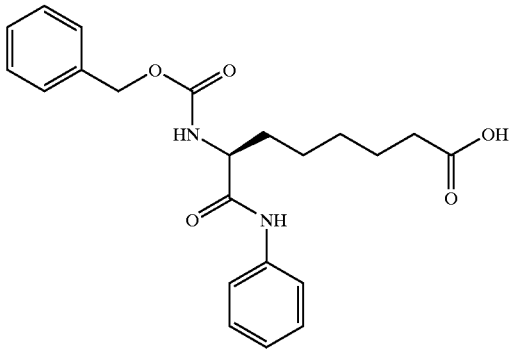

To a solution of ester 51 (76 mg, 0.167 mmol) in CH$_2$Cl$_2$ (5 mL) was added TFA (0.5 mL) and the reaction solution stirred for 5 h. The solution was concentrated under reduced pressure to give crude 52 as a white solid (80 mg) which was used in the next step without purification. TLC R$_f$ 0.32 (5% MeOH/CH$_2$Cl$_2$); $^1$H-NMR (400 MHz, DMSO-d$_6$) δ 11.93 (br s, 1H), 9.99 (s, 1H), 7.58 (d, 2H), 7.55 (d, 1H), 7.35 (m, 4H), 7.29 (t, 2H), 7.03 (t, 1H), 5.02 (m, 2H), 4.11 (br dd, 1H), 2.17 (t, 2H), 1.59 (m, 2H), 1.48 (m, 2H), 1.22 (m, 4H).

(1S)-(6-Hydroxycarbamoyl-1-phenylcarbamoyl-hexyl)-carbamic Acid Benzyl Ester (53)

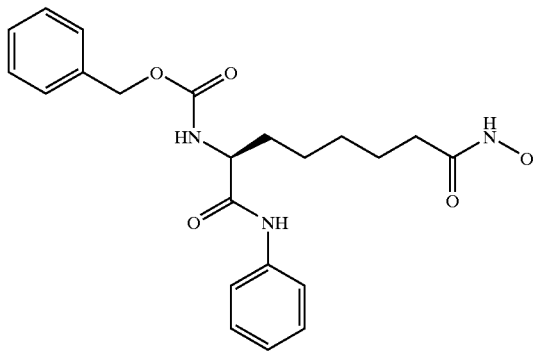

To a solution of crude acid 52 (80 mg) and TBDPSO-NH$_2$ (60 mg, 0.221 mmol) in CH$_2$Cl$_2$ were added DIEA (52 μL, 0.302 mmol) followed by Py.BOP (125 mg, 0.241 mmol). The solution was stirred for 3 h, then concentrated under reduced pressure. The residue was passed through a plug of silica gel (50% EtOAc/hexanes) and the collected eluent evaporated. A white foam (107 mg, 0.164 mmol, 82%) was obtained, this was dissolved in CH$_2$Cl$_2$ (5 mL) and TFA (0.25 mL) was added and the solution stirred for 2 h. A new spot that stained with FeCl$_3$ was indicated by TLC analysis. The mixture was concentrated under reduced pressure, and the residue was solvated in a minimum of EtOAc and the product precipitated with hexanes. The resulting white gel was rinsed with hexanes and dried under vacuum, to give 53 as a white solid (40 mg, 0.097 mmol, 58% over three steps). $^1$H-NMR (400 MHz, DMSO-d$_6$) δ 10.31 (s, 1H), 9.99 (s, 1H), 7.59 (d, 2H), 7.56 (d, 1H), 7.37 (m, 4H), 7.29 (t, 2H), 7.02 (t, 1H), 5.02 (m, 2H), 4.11 (dt, 1H), 1.90 (t, 2H), 1.61 (m, 2H), 1.47 (m, 2H), 1.30 (m, 4H). MS (ESI+) calcd for C$_{22}$H$_{27}$N$_3$O$_5$ 413, found 414 [M+H]$^+$.

(7S)-7-Benzyloxycarbonylamino-7-(quinolin-8-ylcarbamoyl)-heptanoic Acid t-Butyl Ester (54)

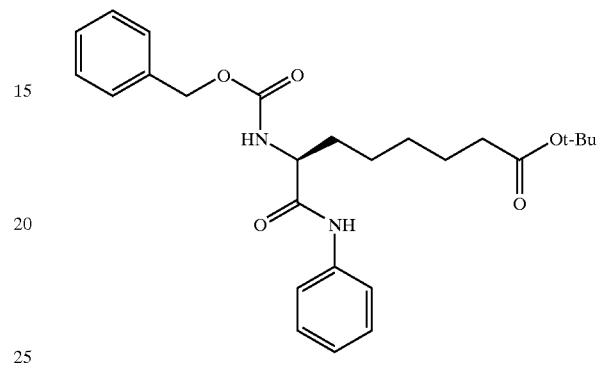

The title compound was made from N-Cbz-L-2-aminosuberic acid 8-t-butyl ester, dicyclohexylamine salt in a manner similar to that for 51. Flash chromatography (0–1% MeOH/CH$_2$Cl$_2$) gave 54 as a light brown solid (70 mg, 0.138 mmol, 82%). TLC R$_f$ 0.42 (2% MeOH/CH$_2$Cl$_2$); $^1$H-NMR (400 MHz, CDCl$_3$) δ 10.19 (s, 1H), 8.77 (dd, 1H), 8.71 (dd, 1H), 8.15 (dd, 1H), 7.52 (m, 2H), 7.45 (m, 1H), 7.33 (m, 4H), 5.50 (br d, 1H), 5.15 (m, 2H), 4.51 (br dd, 1H), 2.17 (t, 2H), 2.00 (m, 1H), 1.79 (m, 1H), 1.56 (m, 2H), 1.45 (m, 2H), 1.40 (s, 9H), 1.38 (m, 2H).

(7S)-7-Benzyloxycarbonylamino-7-(quinolin-8-ylcarbamoyl)-heptanoic Acid (55)

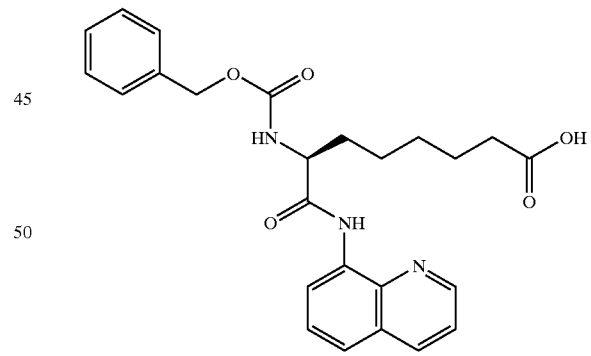

Prepared from 54 in a manner similar to that for 52. Obtained 55 as a brown solid (72 mg, 0.129 mmol). TLC R$_f$ 0.16 (50% EtOAc/hexanes); $^1$H-NMR (400 MHz, DMSO-d$_6$) δ 11.92 (br s, 1H), 10.46 (s, 1H), 8.49 (dd, 1H), 8.63 (dd, 1H), 8.42 (dd, 1H), 8.10 (d, 1H), 7.68 (dd, 1H), 7.58 (t, 1H), 7.36 (m, 2H), 7.28 (m, 2H), 5.09 (m, 2H), 4.22 (m, 1H), 2.19 (t, 2H), 1.83 (m, 1H), 1.67 (m, 1H), 1.48 (m, 2H), 1.39 (m, 2H), 1.28 (m, 2H).

(1S)-[6-Hydroxycarbamoyl-1-(quinolin-8-ylcarbamoyl)-hexyl]-carbamic Acid Benzyl Ester (56)

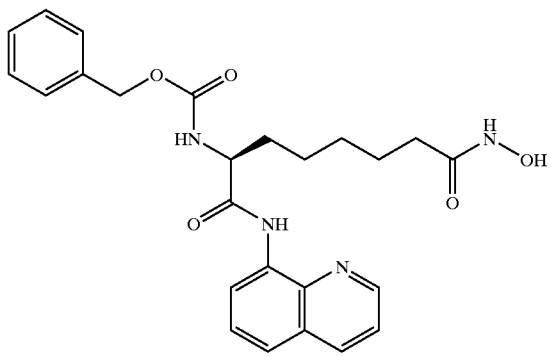

Prepared from 55 in a manner similar to that for 53. Obtained 56 as a white solid (15 mg, 0.032 mmol, 44%). $^1$H-NMR (400 MHz, DMSO-$d_6$) δ 10.46 (s, 1H), 10.31 (s, 1H), 8.85 (dd, 1H), 8.63 (dd, 1H), 8.42 (dd, 1H), 8.12 (d, 1H), 8.66 (m, 2H), 7.58 (t, 1H), 7.37 (m, 2H), 7.28 (m, 2H), 7.20–6.90 (1H), 5.10 (m, 2H), 4.10 (m, 1H), 1.92 (t, 2H), 1.82 (m, 1H), 1.68 (m, 1H), 1.49 (m, 2H), 1.40 (m, 2H), 1.26 (m, 2H). MS (ESI+) calcd for $C_{25}H_{28}N_4O_5$ 464, found 465 [M+H]$^+$.

(7S)-(Cyclohexanecarbonyl-amino)-7-phenylcarbamoyl-heptanoic Acid Methyl Ester (57)

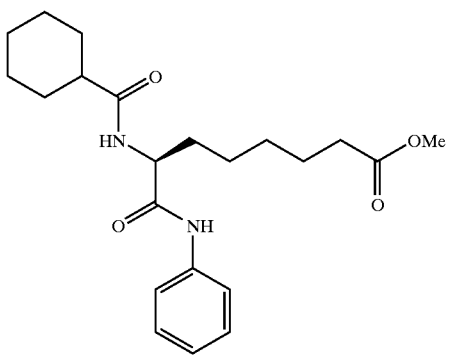

To a solution of 5 (81 mg, 0.214 mmol) in $CH_2Cl_2$ (10 mL) was added TFA (0.5 mL) and the solution stirred for 2 h. The mixture was concentrated under reduced pressure. To a solution of this amine (62 mg, 0.223 mmol) and cyclohexane carboxylic acid (31 μL, 0.245 mmol) in $CH_2Cl_2$ (4 mL) were added Py.BOP (140 mg, 0.268 mmol) and DIEA (58 μL, 0.335 mmol). The solution was stirred for 2 h, concentrated under reduced pressure, and the product purified by flash chromatography (40% EtOAc/hexanes). Evaporation left crude 57 as a white solid (95 mg) containing a small amount of unreacted cyclohexane acid impurity. This material was used in the next step without further purification. TLC $R_f$ 0.58 (50% EtOAc/hexanes); $^1$H-NMR (400 MHz, CDCl$_3$) δ 8.58 (s, 1H), 7.50 (d, 2H), 7.28 (t, 2H), 7.07 (t, 1H), 6.14 (d, 1H), 4.56 (dt, 1H), 3.64 (s, 3H), 2.28 (t, 2H), 2.13 (tt, 1H), 1.94 (m, 1H), 1.85 (m, 2H), 1.76 (m, 2H), 1.64 (m, 4H), 1.41 (m, 5H), 1.22 (m, 4H).

(7S)-(Cyclohexanecarbonyl-amino)-7-phenylcarbamoyl-heptanoic Acid (58)

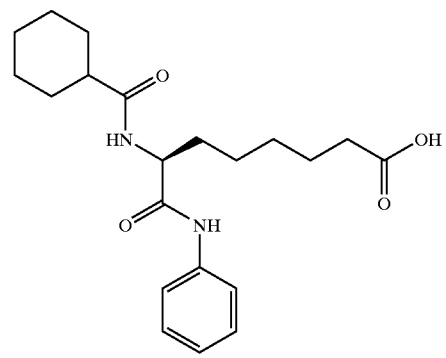

To a solution of ester 57 (95 mg) in MeOH (2.5 mL) at 0° C. was added a solution of NaOH (1 M, 2.5 mL). A white precipitate formed upon addition, which was re-dissolved by the addition of THF (2.5 mL). Additional NaOH (1 M, 1.0 mL) was added after 3 h and the temperature maintained at 0° C. Upon complete disappearance of starting material by TLC analysis, the reaction contents were acidified with HCl (1 N) to obtain a white precipitate. The supernatant was drawn off, and the solid filtered under aspiration. The combined liquors were extracted with EtOAc (3×5 mL), and the extracts combined, washed with brine, dried over MgSO$_4$, and filtered. Concentration under reduced pressure left a white solid which was combined with the filter cake and dried under vacuum to obtain the carboxylic acid 58 (75 mg, 0.200 mmol, 90%). $^1$H-NMR (400 MHz, DMSO-$d_6$) δ 11.95 (s, 1H), 9.98 (s, 1H), 7.90 (d, 1H), 7.58 (d, 1H), 7.28 (t, 2H), 7.02 (t, 1H), 4.33 (dt, 1H), 2.22 (tt, 1H), 2.17 (t, 2H), 1.67 (m, 6H), 1.60 (m, 2H), 1.46 (m, 2H), 1.22 (m, 9H).

(2S)-2-(Cyclohexanecarbonyl-amino)-octanedioic Acid 8-Hydroxyamide 1-Phenylamide (59)

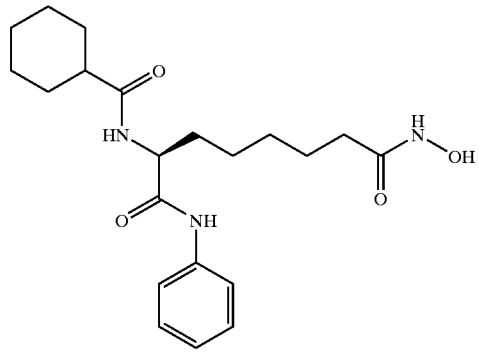

Acid 58 (70 mg, 0.187 mmol), TBDPSO-NH$_2$ (61 mg, 0.224 mmol), and DMAP (5 mg) were dissolved in $CH_2Cl_2$ (4 mL) and EDC (47 mg, 0.243 mmol) was added. The solution was stirred overnight. After concentration under reduced pressure, the material was purified by flash chromatography (50% EtOAc/hexanes). Evaporation of the combined product fractions gave a white foam (80 mg, 0.131 mmol, 70%). To a solution of this protected hydroxamate in $CH_2Cl_2$ (2 mL) and THF (3 mL) was added TFA (0.25 mL) and stirred for 1.5 h. A new spot which stained immediately with FeCl$_3$ was observed on TLC. The solution was concentrated and all volatiles removed under vacuum. The residue was triturated with EtOAc and obtain a white gel precipitate which was transferred to a plastic tube with EtOAc (5 mL). The tube was centrifuged to form a pellet, the supernatant drained, and EtOAc (10 mL) added. The pellet was resuspended with sonication, then centrifuged again, the supernatant discarded, and the residue dried under vacuum. A white solid 59 (18 mg, 0.046 mmol, 35%) was obtained. $^1$H-NMR (400 MHz, DMSO-$d_6$) δ 10.31 (s, 1H), 9.97 (s, 1H), 7.89 (d, 1H), 7.57 (d, 2H), 7.28 (t, 2H), 7.02 (t, 1H), 4.33 (dt, 1H), 2.22 (t, 2H), 1.91 (t, 2H), 1.61 (m, 6H), 1.68 (m, 2H), 1.45 (m, 2H), 1.21 (9H).

Octanedioic Acid Hydroxyamide Quinolin-8-ylamide (60)

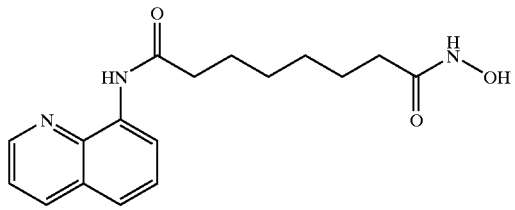

This compound was prepared from suberic acid monomethyl ester in similar fashion to 48, with the use of 8-aminoquinoline. The crude residue obtained after TFA deprotection of the protected hydroxamate was taken up in a small volume of EtOAc and precipitated with hexanes to give 60 as a white solid (18 mg, 0.057 mmol, 21% from the carboxylic acid). $^1$H-NMR (400 MHz, DMSO-$d_6$) δ 10.31 (s, 1H), 10.02 (s, 1H), 8.92 (dd, 1H), 8.61 (dd, 1H), 8.40 (dd, 1H), 7.65 (dd, 1H), 7.63 (dd, 1H), 7.56 (t, 1H), 2.56 (t, 1H), 1.93 (t, 1H), 1.63 (m, 2H), 1.49 (m, 2H), 1.28 (m, 4H). MS (ESI+) calcd for $C_{17}H_{21}N_3O_3$ 315, found 316 [M+H]$^+$.

2-t-Butoxycarbonyl-octanedioic Acid 1-t-Butyl Ester 8-Ethyl Ester (61)

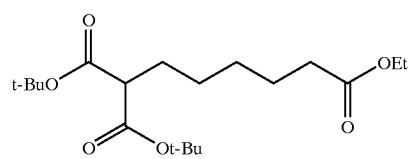

To a stirred suspension of NaH (60% disp., 197 mg, 4.913 mmol) in THF (25 mL) at 0° C. was added di-t-butyl malonate (1.00 mL, 4.466 mmol) and the mixture allowed to warm to ambient temperature. After 1 h, gas had ceased evolving and ethyl 6-bromohexanoate (0.88 mL, 4.913 mmol) was added dropwise. The reaction was brought to reflux overnight. The reaction was carefully quenched with $H_2O$ (10 mL) and diluted with EtOAc. After separation of the layers, the aqueous portion was extracted with EtOAc (3×10 mL). The extracts were pooled and washed with $H_2O$, then brine, dried over $MgSO_4$, and filtered. Concentration under reduced pressure gave a yellow oil which was passed through a plug of silica gel (10% EtOAc/hexanes). Evaporation left a light yellow syrup 61 (1.52 g, 4.24 mmol, 95%). TLC $R_f$ 0.44 (10% EtOAc/hexanes); $^1$H-NMR (400 MHz, CDCl$_3$) δ 4.10 (q, 2H), 3.08 (t, 1H), 2.26 (t, 2H), 1.76 (m, 2H), 1.60 (m, 2H), 1.43 (s, 18H), 1.32 (m, 4H), 1.23 (m, 3H).

2-Carboxy-octanedioic Acid 8-Ethyl Ester (62)

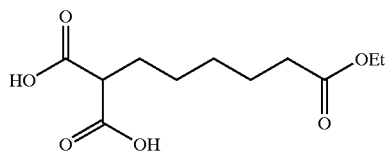

To a solution of triester 61 (500 mg, 1.395 mmol) in $CH_2Cl_2$ (20 mL) was added TFA (2.0 mL) and the reaction mixture stirred overnight. Volatile components were evaporated under vacuum, and the residue repeatedly dissolved in $CH_2Cl_2$ and evaporated to remove all traces of TFA. A solid 62 (327 mg, 1.33 mmol) was obtained and used directly in the next step without further purification. $^1$H-NMR(400 MHz, DMSO-$d_6$) δ 12.62 (br s, 2H), 4.03 (q, 2H), 3.16 (t, 1H), 2.25 (t, 2H), 1.67 (m, 2H), 1.49 (m, 2H), 1.25 (m, 4H), 1.16 (t, 3H).

7,7-Bis-(quinolin-8-ylcarbamoyl)-heptanoic Acid Ethyl Ester (65)

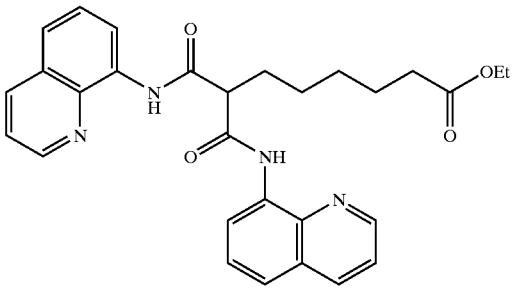

Diacid 62 (150 mg, 0.609 mmol), 8-aminoquinoline (211 mg, 1.462 mmol), and DMAP (5 mg) were dissolved in THF (6 mL). To this solution was added EDC (350 mg, 1.827 mmol) and the reaction allowed to proceed overnight. The mixture was concentrated under reduced pressure and the product purified by flash chromatography (40% EtOAc/hexanes). Evaporation of the combined product fractions left 63 as a light brown solid (100 mg, 0.201 mmol, 14%). $^1$H-NMR (400 MHz, DMSO-$d_6$) δ 10.85 (s, 2H), 8.92 (dd, 2H), 8.64 (dd, 2H), 8.40 (dd, 2H), 7.68 (dd, 2H), 7.62 (dd, 2H), 7.57 (t, 2H), 4.35 (t, 1H), 3.98 (q, 2H), 2.24 (t, 2H), 2.00 (m, 2H), 1.51 (m, 2H), 1.37 (m, 4H), 1.12 (t, 3H).

7,7-Bis-(quinolin-8-ylcarbamoyl)-heptanoic Acid (64)

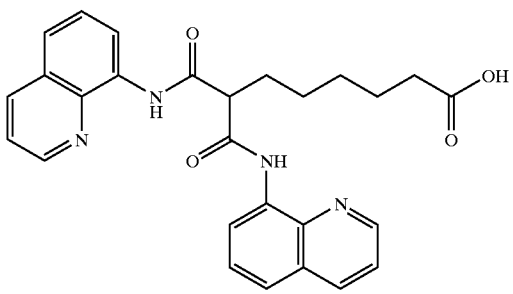

To a solution of ester 63 (94 mg, 0.212 mmol) in MeOH (3 mL) and THF (1 mL) was added a solution of LiOH.H$_2$O (44 mg, 1.062 mmol) in H$_2$O (1 mL) and the mixture was stirred for 5 h. After acidification with HCl (1 N) to pH 7, EtOAc (10 mL) was added and the layers separated. The aqueous portion was extracted with EtOAc (3×5 mL), and the extracts combined, washed with sat. NH$_4$Cl (3 mL), H$_2$O (3 mL), then brine, dried over MgSO$_4$, and filtered. Concentration under reduced pressure left 64 as a white solid (94 mg, 0.200 mmol, 94%). TLC $R_f$ 0.21 (50% EtOAc/hexanes); $^1$H-NMR (400 MHz, DMSO-$d_6$) δ 11.88 (s, 1H), 10.85 (s, 2H), 8.93 (dd, 2H), 8.65 (dd, 2H), 8.40 (dd, 2H), 7.69 (dd, 2H), 7.63 (dd, 2H), 7.58 (t, 2H), 4.35 (t, 1H), 2.16 (t, 2H), 2.00 (m, 2H), 1.49 (m, 2H), 1.38 (m, 4H).

2-(Quinolin-8-ylcarbamoyl)-octanedioic Acid 8-Hydroxyamide 1-Quinolin-8-ylamide (65)

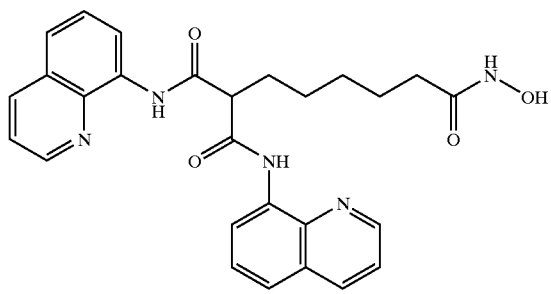

Acid 64 (94 mg, 0.200 mmol), TBDPSO-NH₂ (74 mg, 0.272 mmol), and DMAP (5 mg) were dissolved in CH₂Cl₂ (4 mL) and EDC (57 mg, 0.295 mmol) was added. The solution was stirred overnight, then concentrated under reduced pressure. Purification by flash chromatography (30–50% EtOAc/hexanes) and evaporation of the combined product fractions gave a white foam. To a solution of this protected hydroxamate in CH₂Cl₂ (4 mL) was added TFA (0.2 mL) and the solution stirred for 4 h. TLC indicated complete consumption of starting material and a new spot that stained with FeCl₃. The solution was concentrated under reduced pressure, and the residue dissolved in a minumum of EtOAc. Addition of hexanes gave a white precipitate, from which the mother liquor was removed. After rinsing with hexanes, the residue was dried under vacuum to leave 65 as a white solid (30 mg, 0.061 mmol, 22% from the carboxylic acid). ¹H-NMR (400 MHz, CDCl₃) δ 10.85 (s, 2H), 10.30 (s, 1H), 8.93 (dd, 2H), 8.65 (dd, 2H), 8.40 (dd, 2H), 7.69 (dd, 2H), 7.63 (dd, 2H), 7.58 (t, 2H), 4.35 (t, 1H), 1.99 (m, 2H), 1.92 (t, 2H), 1.48 (m, 2H), 1.35 (m, 4H). MS (ESI+) calcd for C₂₇H₂₇N₅O₄ 485, found 486 [M+H]⁺.

2-(Quinolin-3-ylcarbamoyl)-octanedioic Acid 8-Hydroxyamide 1-Quinolin-3-ylamide (68)

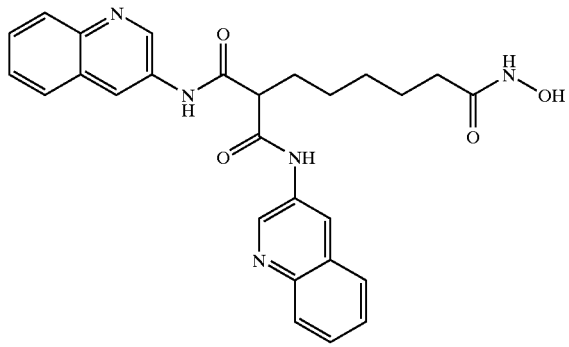

The title compound was made from diacid 62 as analogous to 65. ¹H-NMR (400 MHz, DMSO-d₆) δ 10.60 (s, 1H), 10.34 (s, 1H), 8.95 (dd, 2H), 8.74 (s, 2H), 7.93 (dd, 2H), 7.64 (dd, 2H), 7.56 (dd, 2H), 3.71 (t, 1H), 1.96 (m, 4H), 1.51 (m, 2H), 1.34 (m, 4H).

6-Bromohexanoic Acid Phenylamide (76)

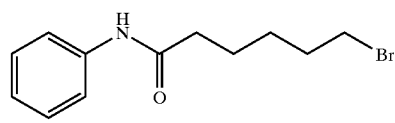

To a solution of 6-bromohexanoyl chloride (1.00 mL, 6.53 mmol) in THF (35 mL) at 0° C. was added dropwise a solution of aniline (0.60 mL, 6.53 mmol) and TEA (1.09 mL, 7.84 mmol) in THF (5 mL). The reaction mixture was allowed to warm to ambient temperature and stirred for 2 h. The mixture was filtered, the solids rinsed with EtOAc, and the filtrate reduced under vacuum. The residue was partitioned between H₂O (15 mL) and EtOAc (20 mL) and the layers separated. The aqueous portion was extracted with EtOAc (3×10 mL) and the organic layers combined, washed with HCl (1 N), brine, dried over MgSO₄, and filtered. Concentration under reduced pressure left a brown oil which was passed through a plug of silica gel (30% EtOAc/hexanes) under aspiration. Concentration under reduced pressure left 67 as a solid (1.55 g, 5.74 mmol, 88%). TLC R_f 0.36 (25% EtOAc/hexanes); ¹H-NMR (400 MHz, DMSO-d₆) δ 9.85 (s, 1H), 7.57 (d, 2H), 7.27 (t, 2H), 7.01 (t, 1H), 3.53 (t, 2H), 2.30 (t, 2H), 1.81 (t, 2H), 1.63 (m, 2H), 1.42 (m, 2H); MS (ESI+) calcd for C₁₂H₁₆BrNO 268+270, found 269+271 [M+H]⁺.

Thioacetic Acid S-(5-Phenylcarbamoyl-pentyl)ester (68)

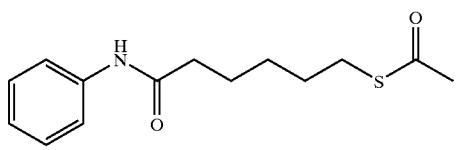

Bromide 67 (200 mg, 0.74 mmol), potassium thioacetate (110 mg, 0.96 mmol), and sodium iodide (10 mg) were combined in THF (6 mL) and the vigorously stirred mixture brought to reflux overnight. The reaction mixture was concentrated, the passed through a plug of silica gel (20% EtOAc/hexanes, 200 mL) under aspiration. Evaporation under reduced pressure left 68 as an orange crystalline solid (190 mg, 0.72 mmol, 97%). TLC R_f 0.22 (25% EtOAc/hexanes); ¹H-NMR (400 MHz, DMSO-d₆) δ 9.83 (s, 1H), 7.56 (d, 2H), 7.27 (t, 2H), 7.00 (t, 1H), 2.82 (t, 2H), 2.30 (s, 3H), 2.28 (t, 2H), 1.57 (m, 2H), 1.52 (m, 2H), 1.35 (m, 2H).

6-Methanesulfonylamino-hexanoic Acid (69)

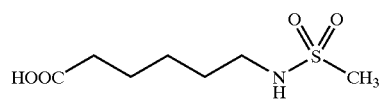

6-aminohexanoic acid (904 mg, 6.89 mmol) and NaOH (415 mg, 10.34 mmol) were dissolved in H₂O (30 mL) and cooled to 0–5° C. Methanesulfonyl chloride (0.586 mL, 7.58 mmol) was added dropwise and the reaction mixture stirred for 2 h, then warmed to ambient temperature and stirred for an additional 2 h. The mixture was acidified with HCl (1 N) and extracted with EtOAc (3×15 mL). The extracts were combined, washed with H₂O, then brine, dried over MgSO₄, and filtered. Evaporation under reduced pressure gave 69 as a white crystalline solid (207 mg, 0.99 mmol, 14%). ¹H-NMR (400 MHz, DMSO-d₆) δ 11.95 (s, 1H), 6.91 (t, 1H), 2.90 (dt, 2H), 2.87 (s, 3H), 2.20 (t, 2H), 2.48 (m, 2H), 2.43 (m, 2H), 1.27 (m, 2H).

6-Methanesulfonylamino-hexanoic Acid Phenylamide (70)

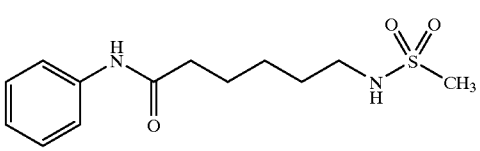

To a solution of acid 69 (100 mg, 0.48 mmol), aniline (60 μL, 0.66 mmol), and DMAP (5 mg) in THF (5 mL) was added EDC (119 mg, 0.57 mmol). The reaction mixture was stirred overnight, then partitioned between H$_2$O (10 mL) and EtOAc (15 mL). The layers were separated, and the aqueous portion extracted with EtOAc (3×10 mL). The organic fractions were combined, washed with sat. NH$_4$Cl (5 mL), then brine, dried over MgSO$_4$, and filtered. Concentration under reduced pressure gave 70 as a white crystalline solid (130 mg, 0.46 mmol, 95%). $^1$H-NMR (400 MHz, DMSO-d$_6$) δ 9.84 (s, 1H), 7.57 (d, 2H), 7.26 (t, 2H), 7.00 (t, 1H), 6.92 (t, 1H), 2.91 (dt, 2H), 2.85 (s, 3H), 1.58 (m, 2H), 1.47 (m, 2H), 1.31 (m, 2H).

9,9,9-Trifluoro-8-oxononanoic Acid Methyl Ester (71)

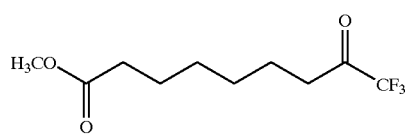

To a solution of suberic acid monomethyl ester (1.00 g, 5.31 mmol) in THF (15 mL) was added oxalyl chloride (2 mL) followed by DMF (1 drop). The solution was stirred for 2 h, then concentrated under reduced pressure. Volatiles were removed under high vacuum overnight, leaving a yellow oil (1.08 g, 5.22 mmol, 98%). This crude acid chloride was then transformed into the trifluoromethyl ketone by a literature method as follows. (65) To a solution of the acid chloride (1.08 g, 5.22 mmol) in CH$_2$Cl$_2$ (45 mL) at 0° C. were added trifluoroacetic anhydride (4.64 mL, 32.81 mmol) and pyridine (3.54 mL, 43.74 mmol). The mixture was allowed to warm to ambient temperature and stirred for 2 h. After returning to 0° C., ice-cold H$_2$O (20 mL) was added carefully. Additional H$_2$O (100 mL) was added and the layers separated. The aqueous phase was extracted with CH$_2$Cl$_2$ (2×30 mL) and the organic layers combined, washed with brine, dried over MgSO$_4$, and filtered. Evaporation under reduced pressure left a brown oil, which was purified by flash chromatography (2–4% MeOH/CH$_2$Cl$_2$) to give 71 as a clear oil (641 mg, 2.67 mmol, 49%). TLC R$_f$ 0.24 (2% MeOH/CH$_2$Cl$_2$); $^1$H-NMR (400 MHz, CDCl$_3$) δ 3.67 (s, 3H), 2.71 (t, 2H), 2.31 (t, 2H), 1.65 (m, 4H), 1.35 (m, 4H).

9,9,9-Trifluoro-8-oxo-nonanoic Acid Phenylamide (72)

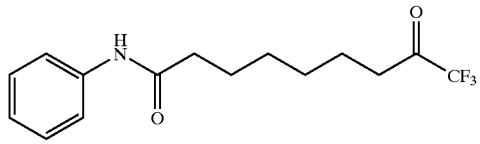

To a solution of ester 71 (300 mg, 1.25 mmol) in THF (18 mL) was added a solution of LiOH.H$_2$O (262 mg, 6.24 mmol) in H$_2$O (6 mL) and the suspension was stirred overnight. The mixture was then acidified with HCl (1 N) to pH 2 and then extracted with EtOAc (3×15 mL). The extracts were combined, washed with brine, dried over MgSO$_4$, and filtered. Concentration under reduced pressure left a white solid (211 mg, 0.93 mmol, 75%). To a solution of this acid (109 mg, 0.48 mmol), EDC (111 mg, 0.58 mmol), and DMAP (5 mg) in CH$_2$Cl$_2$ (5 mL) was added aniline (49 µL, 0.53 mmol) and the reaction allowed to proceed overnight. The solution was partitioned between H$_2$O (5 mL) and EtOAc (10 mL). The layers were separated, and the aqueous phase extracted with EtOAc (3×5 mL). The organic portions were combined, washed with brine, dried over MgSO$_4$, and filtered. Evaporation under reduced pressure left a solid which was purified by preparative TLC (30% EtOAc/hexanes) with isolation of the least polar band by EtOAc extraction. The extract was concentrated to give 72 as a yellowish solid (92 mg, 0.31 mmol, 65%). TLC R$_f$ 0.48 (50% EtOAc/hexanes); $^1$H-NMR (400 MHz, CDCl$_3$) δ 7.51 (d, 2H), 7.32 (t, 2H), 7.10 (t, 1H), 2.72 (t, 2H), 2.36 (t, 2H), 1.72 (m, 4H), 1.40 (m, 4H); $^{19}$F NMR (? MHz, CDCl$_3$) –78.40 (s, 3F); MS (APCI+) calcd for C$_{15}$H$_{19}$F$_3$NO$_2$ 301, found 325 [M+Na]$^+$.

(5-Phenylcarbamoyl-pentyl)-carbamic Acid t-Butyl Ester (73)

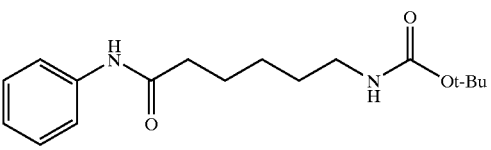

To a solution of N-Boc-6-aminohexanoic acid (2.50 g, 10.81 mmol), EDC (2.69 g, 14.05 mmol), and DMAP (20 mg) in CH$_2$Cl$_2$ (100 mL) was added aniline (1.04 mL, 11.35 mmol) and the mixture stirred overnight. The solution was evaporated under reduced pressure to a small volume, then partitioned between H$_2$O (20 mL) and EtOAc (30 mL). The layers were separated, and the aqueous phase extracted with EtOAc (3×15 mL). The organic portions were combined, washed with sat. NH$_4$Cl (5 mL), then brine, dried over MgSO$_4$, and filtered. Concentration under reduced pressure left pure 73 as a white solid (3.14 g, 10.25 mmol, 95%). TLC R$_f$ 0.40 (50% EtOAc/hexanes); $^1$H-NMR (400 MHz, DMSO-d$_6$) δ 9.81 (s, 1H), 7.56 (d, 2H), 7.26 (t, 2H), 7.00 (t, 1H), 6.74 (t, 1H), 2.89 (dt, 2H), 2.27 (t, 2H), 1.56 (m, 2H), 1.38 (m, 2H), 1.35 (s, 9H), 1.25 (m, 2H).

6-Aminohexanoic Acid Phenylamide, TFA Salt (74)

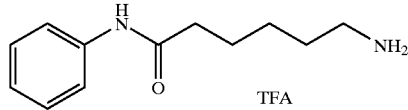

To a solution of carbamate 73 (300 mg, 0.98 mmol) in CH$_2$Cl$_2$ (15 mL) was added TFA (0.75 mL) and the solution stirred overnight. Complete consumption of starting material was confirmed by TLC. The mixture was evaporated under reduced pressure to remove all volatiles, leaving an off-white solid (295 mg, 0.92 mmol, 94%). Crude 74 was used without further purification.

N-(N-Phenylcarbamoyl-5-pentyl)phosphoramidic Acid Dimethyl Ester (75)

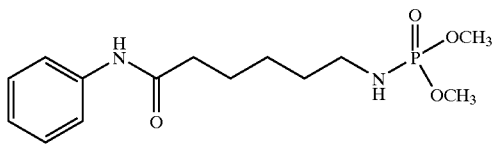

To a stirred suspension of ammonium salt 74 (197 mg, 0.62 mmol) and DIEA (148 µL, 0.85 mmol) in CH$_2$Cl$_2$ (7 mL) at 0° C. was added dropwise dimethyl chlorophosphate (77 µL, 0.72 mmol). The mixture was allowed to warm to ambient temperature and stirred overnight. The solution was diluted with H$_2$O (10 mL) and the layers separated. The aqueous phase was extracted with CH$_2$Cl$_2$ (3×10 mL), the organic portions combined, washed with sat. NH$_4$Cl (5 mL), then brine, dried over MgSO$_4$, and filtered. After concentration, the residue was purified by flash chromatography (2–5% MeOH/CH$_2$Cl$_2$), and the fractions containing the more polar of the two UV-active bands on TLC were combined and concentrated, giving 75 as a clear oil (40 mg, 0.13 mmol, 20%). TLC R$_f$ 0.23 (5% MeOH/CH$_2$Cl$_2$); $^1$H-NMR (400 MHz, DMSO-d$_6$) δ 9.84 (s, 1H), 7.57 (d, 2H), 7.26 (t, 2H), 7.00 (t, 1H), 4.90 (dt, 1H), 3.51 (d, 6H), 2.71 (m, 2H), 2.28 (t, 2H), 1.56 (m, 2H), 1.40 (m, 2H), 1.29 (m, 2H).

Methyl N-(5-N-Phenylcarbamoylpentyl)methylphosphonamidate (76)

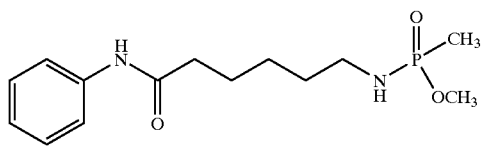

To a suspension of ammonium salt 74 (155 mg, 0.48 mmol) in CH$_3$CN (8 mL) were added DIEA (0.21 mL) and methyl methylphosphonochloridate (77 mg, 0.600 mmol). The reaction mixture was stirred overnight, during which time it clarified. The solution was partitioned between H$_2$O (10 mL) and EtOAc (15 mL) and the layers separated. The aqueous portion was extracted with EtOAc (3×10 mL) and the organics combined, washed with sat. NH$_4$Cl (1×5 mL), then brine, dried over MgSO, apd filtered. The product was purified by flash chromatography (3–10% MeOH/CH$_2$Cl$_2$), and the fractions containing the more polar spot were combined and concentrated to give 76 as a clear oil (102 mg, 0.34 mmol, 71%). TLC R$_f$ 0.16 (5% MeOH/CH$_2$Cl$_2$); $^1$H-NMR (400 MHz, DMSO-d$_6$) δ 9.85 (s, 1H), 7.57 (d, 2H), 7.26 (t, 2H), 7.00 (t, 1H), 4.52 (dt, 1H), 3.43 (d, 3H), 2.73 (m, 2H), 2.28 (t, 2H), 1.57 (m, 2H), 1.38 (m, 2H), 1,28 (m, 2H), 1.26 (d, 3H).

EXAMPLE 18

Synthesis of Compound 77

Diethyl 3-Bromophenylmalonate

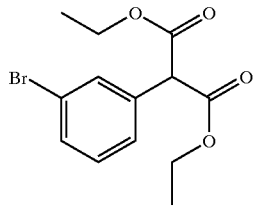

Diethyl 3-bromophenyl malonate was prepared according to the procedures of Cehnevert, R. and Desjardins, M. *Can. J. Chem.* 1994. 72, 3212–2317. $^1$H NMR (CDCl$_3$, 300 MHz) δ 7.6 (s, 1H), 7.50 (d, 1H, J=7.9 Hz), 7.37 (d, 1H, J=7.9 Hz), 7.26 (t, 1H, J=7.9 Hz), 4.58 (s, 1H), 4.22 (m, 4H), 1.29 (t, J=10 Hz).

3-Bromophenyl Malonyl di(Phenylamide)

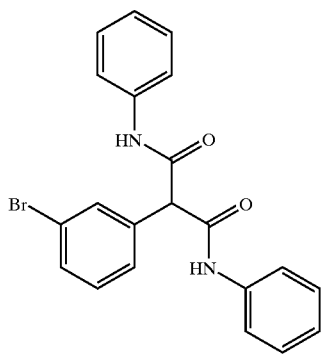

Diethyl 3-bromophenyl malonate (1 g, 3.2 mmol) was added to aniline (5 mL). The reaction mixture was purged with Ar (g) and brought to reflux for 2 h. After cooling, the reaction mixture was diluted with 10% HCl (20 mL) and ethyl acetate (50 mL). The organic layer was separated and concentrated to afford 3-bromophenyl malonyl di(phenylamide) as a white powder. (540 mg. 1.3 mmol, 42%). $^1$H NMR (d6-DMSO, 300 MHz) δ 10.3 (bs, 2H), 7.65 (s, 1H), 7.60 (d, 4H, J=7.9 Hz), 7.54 (d, 1H, J=7.9 Hz), 7.46 (d, 1H, J=7.8 Hz), 7.35 (t, 1H, J=7.8 Hz), 7.31 (t, 4H, J=7.8 Hz), 7.06 (t, 2H, J=7.6 Hz), 4.91 9s, 1H).

3-(Malonyl di(Phenylamide))cinnamic Acid

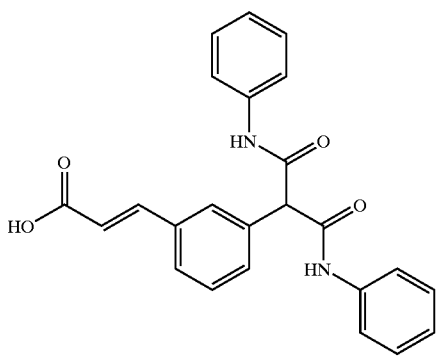

3-bromophenyl malonyl di(phenylamide) (500 mg, 1.22 mmol), acrylic acid (115 mg, 1.6 mmol, 1.3 equiv.), Pd(OAc)$_2$ (2 mg), tri-o-tolyl phosphone (20 mg),tributyl amine (0.6 mL) and xylenes (5 mL) were heated to 120° C. for 6 h in a sealed vessel. After cooling, the reaction was diluted with 5% HCl (10 mL) and ethyl acetate (50 mL). The organic layer was separated, filtered and on standing 3-(malonyl di(phenylamide))cinnamic acid precipitated as a white powder (450 mg, 1.12 mmol, 92%). $^1$H NMR (d6-DMSO, 300MHz, δ 12.4 (bs, 1H), 10.3 (bs, 2H), 7.73 (s, 1H), 7.7–7.5 (m, 6H), 7.52 (d, 1H, J=7.7 Hz), 7.43 (t, 1H, J=7.6 Hz), 7.31 (t, 4H, J=7.5 Hz), 7.06 (t, 2H, J=7.4 Hz), 6.52 (d, 1H, J=16 Hz), 4.95 (s, 1H). APCI-MS 401 (M+1).

3-(Malonyl di(Phenylamide))cinnamyl Hydroxamic Acid (77)

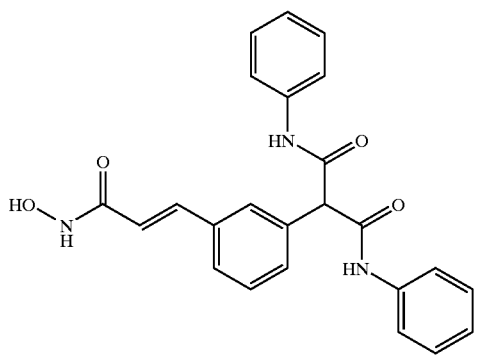

3-(malonyl di(phenylamide)) cinnamic acid (200 mg, 0.5 mmol) was dissolved in dry $CH_2CL_2$ (10 mL). Isobutylchloroformate (0.10 mL, 0.77 mmol) and triethyl amine (0.20 mL) were added at 0° C. with stirring. After 2 h at 25° C., O-(t-butyldiphenyl silyl)hydroxylamine was added and the mixture was stirred an additional 4 h. The crude reaction mixture was applied directly to a pad a silica gel (15 g) and elution with 20% ethyl acetate/hexanes afforded the corresponding silyl protected hydroxamic acid ($R_f$ =0.58, 50% ethyl acteate/hexanes) as a foam. This was treated directly with 10% trifluoracetic acid in dichloromethane (10 mL) for 4 h. The solvents were concentrated at 50° C. by rotavap and the residue was suspended in ethyl ether (10 mL). Filtration of the resultant precipitate afforded compound 77 as a white powder (150 mg, 0.365 mmol, 73%). $^1$H NMR (d6-DMSO, 300 MHz, δ 10.8 (bs, 0.5H), 10.2 (bs, 2H), 9.06 (bs, 0.5H), 7.7–7.55 (m,5H), 7.53–7.38 (m, 4H), 7.31 (t, 4H, J=7.7 Hz), 7.06 (t, 2H, J=7.3 Hz), 6.50 (d, 1H, J=16 Hz), 4.92 (s, 1H). APCI-MS 416 (M+1).

The effect of compound 77 on MEL cell differentiation and Histone Deacetylase activity is shown in Table 2. Compound 77 corresponds to structure 683 in Table 2. As evident from Table 2, compound 77 is expected to be a highly effective cytodifferentiating agent.

Results

All the compounds which were prepared were tested. Table 2 below shows the results of testing of only a subgroup of compounds. Table 2 is compiled from experiments similar to the experiments described in Examples 7–10 above. The tested compounds were assigned structure numbers as shown in Table 2. The structure numbers were randomly assigned and do not correlate to the compound numbers used elsewhere in this disclosure.

The results shown in Table 2 verify the general accuracy of the predictive principals for the design of compounds having cell differentiation and HDAC inhibition activity discussed above in this disclosure. Based on the principals and synthesis schemes disclosed, a number of additional compounds can readily be designed, prepared and tested for cell differentiation and HDAC inhibition activity.

FIGS. 11a–f show the effect of selected compounds on affinity purified human epitope-tagged (Flag) HDAC1. The effect was assayed by incubating the enzyme preparation in the absence of substrate on ice for 20 minutes with the indicated amounts of compound. Substrate ([$^3$H]acetyl-labeled murine erythroleukemia cell-derived histones) was added and the samples were incubated for 20 minutes at 37° C. in a total volume of 30 μl. The reactions were then stopped and released acetate was extracted and the amount of redioactivity released determined by scintillation counting. This is a modification of the HDAC Assay described in Richon et al. 1998 (39).

TABLE 2

Inhibition data of selected compounds.

| NO: | Structure | MEL Diff | | | | HDAC inh | |
|---|---|---|---|---|---|---|---|
| | | Range | Opt. | % B+ | cells/ml x 10$^{-5}$ | Range | ID50 |
| SAHA (390) | | 0.5 to 50 μM | 2.5 μM | 68 | 3.6 | 0.001 to 100 μM | 200 nM |
| 654 | | 0.1 to 50 μM | 200 nM | 44 | 9 | 0.0001 to 100 μM | 1 nM |

TABLE 2-continued

Inhibition data of selected compounds.

| NO: | Structure | MEL Diff Range | Opt. | % B+ | cells/ml × 10⁻⁵ | HDAC inh Range | ID50 |
|---|---|---|---|---|---|---|---|
| 655 | | 0.1 to 50 μM | 400 nM | 16 | 3.3 | 0.01 to 100 μM | 100 nM |
| 656 | | 0.4 to 50 μM | | 0 | | 0.01 to 100 μM | >100 μM |
| 657 | | 0.4 to 50 μM | | 0 | | 0.01 to 100 μM | >100 μM |
| 658 | | 0.01 to 50 μM | 40 nM | 8 | 13 | 0.0001 to 100 μM | 2.5 nM |
| 659 | | 4.5 to 50 μM | | 0 | | 0.01 to 100 μM | 10 μM |

TABLE 2-continued

Inhibition data of selected compounds.

| NO: | Structure | MEL Diff Range | Opt. | B+ % | cells/ml × 10⁻⁵ | HDAC inh Range | ID50 |
|---|---|---|---|---|---|---|---|
| 660 | (phenyl-NH-C(=O)-CH(NH-C(=O)-3-pyridyl)-(CH2)4-C(=O)-NH-OH) | 0.2 to 12.5 μM | 800 nM | 27 | | 0.001 to 100 μM | 50 nM |
| 661 | (quinolin-8-yl-NH-C(=O)-CH(NH-C(=O)-Ph)-(CH2)4-C(=O)-NH-OH) | 0.1 to 50 μM | 500 nM | 7 | | 0.01 to 100 μM | 20 nM |
| 662 | (phenyl-NH-C(=O)-(CH2)6-NH-S(=O)2-CH3) | 0.2 to 50 μM | | 0 | | 0.001 to 100 μM | >100 μM |
| 663 | (cyclohexyl-NH-C(=O)-CH(NH-C(=O)-Ph)-(CH2)4-C(=O)-NH-OH) | 0.2 to 50 μM | 200 nM | 43 | 7 | 0.001 to 100 μM | 100 nM |
| 664 | (phenyl-NH-C(=O)-CH(NH-C(=O)-quinolin-3-yl)-(CH2)4-C(=O)-NH-OH) | 0.2 to 50 μM | 400 nM | 33 | 22 | 0.001 to 100 μM | 50 nM |

TABLE 2-continued

Inhibition data of selected compounds.

| NO: | Structure | MEL Diff Range | Opt. | % B+ | cells/ml × 10⁻⁵ | HDAC inh Range | ID50 |
|---|---|---|---|---|---|---|---|
| 665 | | 0.1–50 μM | 150 nM | 24 | 30 | 0.001 to 100 μM | 50 nM |
| 666 | | 0.1–50 μM | 150 nM | 31 | 28 | 0.001 to 100 μM | 100 nM |
| 667 | | 0.02–10 μM | 80 nM | 27 | 2 | 0.001 to 100 μM | 50 nM |
| 668 | | 0.02 to 10 μM | 10 μM | 11 | 4.7 | 0.001 to 100 μM | 100 nM |
| 669 | | 0.8 to 50 μM | 4 μM | 11 | 16.0 | 0.001 to 100 μM | 10 μM |

TABLE 2-continued

Inhibition data of selected compounds.

| NO: | Structure | MEL Diff Range | Opt. | % B+ | cells/ml × 10⁻⁵ | HDAC inh Range | ID50 |
|---|---|---|---|---|---|---|---|
| 670 | (phenyl-NH-C(O)-(CH2)5-C(O)-CF3) | 0.4 to 50 μM | No effect up to 25 μM | — | 13.0 | 0.001 to 100 μM | >100 μM |
| 671 | (5-dimethylamino-naphthalene-2-sulfonamide-(CH2)4-C(O)-NHOH) | 0.4 to 50 μM | 3.1 μM | 35 | 12.5 | 0.001 to 100 μM | 200 nM |
| 672 | (phenyl-NH-C(O)-(CH2)5-NH-P(O)(OCH3)(CH3)) | 0.8 to 50 μM | | 0 | No Inh | 0.01 to 100 μM | 100 μM |
| 673 | (phenyl-NH-C(O)-(CH2)5-NH-P(O)(OCH3)(OCH3)) | 0.8 to 50 μM | | 0 | No Inh | 0.01 to 100 μM | 100 μM |
| 674 | (bis-imidazolyl carbinol linked structure) | 0.8 to 50 μM | | 0 | Dead at 25 μM | 0.01 to 100 μM | 50 μM |
| 675 | (phenyl-NH-C(O)-(CH2)5-S-C(O)-CH3) | 0.8 to 50 μM | | 0 | No Inh | 0.001 to 100 μM | >100 μM |
| 676 | (phenyl-NH-C(O)-(CH2)5-Br) | 0.8 to 50 μM | | 0 | No Inh | 0.01 to 100 μM | 100 μM |

TABLE 2-continued

Inhibition data of selected compounds.

| NO: | Structure | MEL Diff | | | | HDAC inh | |
| | | Range | Opt. | B+ | cells/ml × $10^{-5}$ | Range | ID50 |
| --- | --- | --- | --- | --- | --- | --- | --- |
| 677 | (quinolin-3-yl and quinolin-3-yl malonamide with suberoylhydroxamic acid) | 0.05 to 25 μM | 1.6 μM | 23 | 4.5 | 0.001 to 100 μM | 5 nM |
| 678 | PhNH-C(O)-(CH2)4-SO2-NH2 | 0.8 to 50 μM | | 0 | No Inh | 0.001 to 100 μM | >100 μM |
| 679 | PhNH-C(O)-(CH2)4-imidazole | 0.8 to 50 μM | | 0 | No Inh | 0.001 to 100 μM | >100 μM |
| 680 | PhNH-C(O)-(CH2)6-S-C(O)CH3 | | | | | 0.01 to 100 μM | >100 μM |
| 681 | (quinolin-8-yl and quinolin-8-yl, phenyl-substituted malonamide with suberoylhydroxamic acid) | 0.8 to 50 μM | 3 μM | 3 | 2.5 | 0.01 to 100 μM | 200 nM |

TABLE 2-continued

Inhibition data of selected compounds.

| NO: | Structure | MEL Diff Range | Opt. | % B+ | cells/ml × $10^{-5}$ | HDAC inh Range | ID50 |
|---|---|---|---|---|---|---|---|
| 682 | 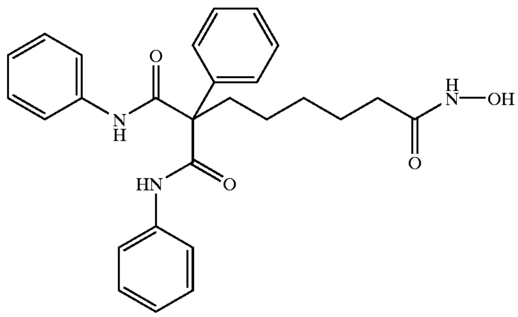 | 0.8 to 50 μM | 50 μM | 8 | 1.1 | 0.01 to 100 μM | 150 nM |
| 683 | 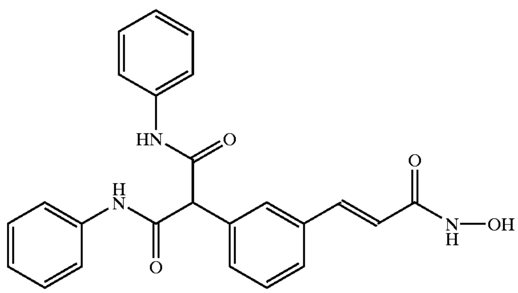 | 0.01 to 0.1 μM | 20 nM | 9 | 9.0 | 0.0001 to 100 μM | 1 nM |
| 684 | 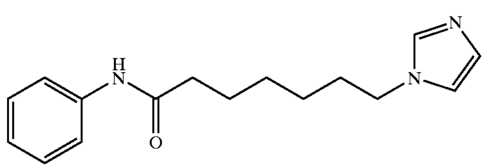 | 0.4 to 50 μM | | 0 | No inh | 0.01 to 100 μM | 100 μM |
| 685 | 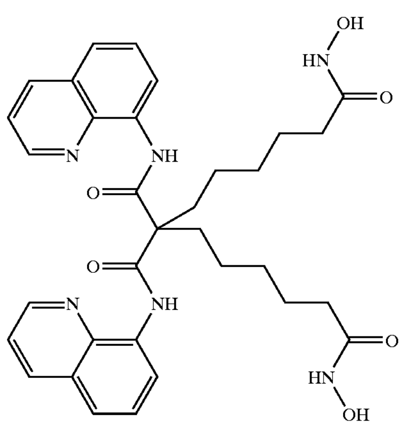 | 0.125 to 5 μM | 1.0 μM | 20 | 1.0 | 0.01 to 100 μM | 150 nM |
| 686 | 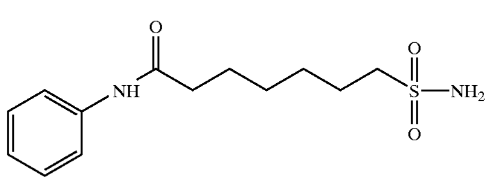 | 0.4 to 50 μM | | 0 | No inh | 0.01 to 100 μM | 100 μM |

TABLE 2-continued

Inhibition data of selected compounds.

| NO: | Structure | MEL Diff Range | Opt. | % B+ | cells/ml × 10⁻⁵ | HDAC inh Range | ID50 |
|---|---|---|---|---|---|---|---|
| 687 | | 0.125 to 5 μM | | 0 | No inh | 0.01 to 100 μM | 200 nM |
| 688 | | 0.4 to 50 μM | | 0 | No inh | 0.01 to 100 μM | >100 μM |
| 689 | | 5.0 to 40 μM | 35 μM | 48 | 2.0 | 0.01 to 100 μM | 200 nM |
| 690 | | 5.0 to 40 μM | 10 μM | 38 | 2.5 | 0.01 to 100 μM | 150 nM |
| 691 | | 1.0 to 25 μM | | 0 | No inh | 0.01 to 100 μM | 100 nM |

TABLE 2-continued

Inhibition data of selected compounds.

| NO: | Structure | MEL Diff Range | Opt. | % B+ | cells/ml × $10^{-5}$ | HDAC inh Range | ID50 |
|---|---|---|---|---|---|---|---|
| 692 | 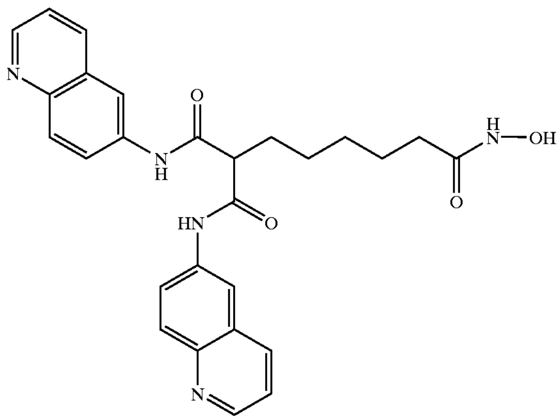 | 0.03 to 5 $\mu M$ | 1 $\mu M$ | 27 | 18.0 | 0.01 to 100 $\mu M$ | 1 nM |
| 693 | 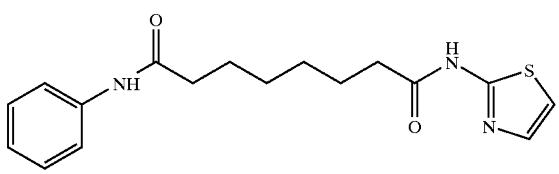 | 0.4 to 50 $\mu M$ | | 0 | No inh | 0.01 to 100 $\mu M$ | >100 $\mu M$ |

BIBLIOGRAPHY

1. Sporn, M. B., Roberts, A. B., and Driscoll, J. S. (1985) in Cancer: Principles and Practice of Oncology, eds. Hellman, S., Rosenberg, S. A., and DeVita, V. T., Jr., Ed. 2, (J. B. Lippincott, Philadelphia), P. 49.
2. Breitman, T. R., Selonick, S. E., and Collins, S. J. (1980) Proc. Natl. Acad. Sci. USA 77: 2936–2940.
3. Olsson, I. L. and Breitman, T. R. (1982) Cancer Res. 42: 3924–3927.
4. Schwartz, E. L. and Sartorelli, A. C. (1982) Cancer Res. 42: 2651–2655.
5. Marks, P. A., Sheffery, M., and Rifkind, R. A. (1987) Cancer Res. 47: 659.
6. Sachs, L. (1978) Nature (Lond.) 274: 535.
7. Friend, C., Scher, W., Holland, J. W., and Sato, T. (1971) Proc. Natl. Acad. Sci. (USA) 68: 378–382.
8. Tanaka, M., Levy, J., Terada, M., Breslow, R., Rifkind, R. A., and Marks, P. A. (1975) Proc. Natl. Acad. Sci. (USA) 72: 1003–1006.
9. Reuben, R. C., Wife, R. L., Breslow, R., Rifkind, R. A., and Marks, P. A. (1976) Proc. Natl. Acad. Sci. (USA) 73: 862–866.
10. Abe, E., Miyaura, C., Sakagami, H., Takeda, M., Konno, K., Yamazaki, T., Yoshika, S., and Suda, T. (1981) Proc. Natl, Acad, Sci. (USA) 78: 4990–4994.
11. Schwartz, E. L., Snoddy, J. R., Kreutter, D., Rasmussen, H., and Sartorelli, A. C. (1983) Proc. Am. Assoc. Cancer Res. 24: 18.
12. Tanenaga, K., Hozumi, M., and Sakagami, Y. (1980) Cancer Res. 40: 914–919.
13. Lotem, J. and Sachs, L. (1975) Int. J. Cancer 15: 731–740.
14. Metcalf, D. (1985) Science, 229: 16–22.
15. Scher, W., Scher, B. M., and Waxman, S. (1983) Exp. Hematol. 11: 490–498.
16. Scher, W., Scher, B. M., and Waxman, S. (1982) Biochem. & Biophys. Res. Comm. 109: 348–354.
17. Huberman, E. and Callaham, M. F. (1979) Proc. Natl. Acad. Sci. (USA) 76: 1293–1297.
18. Lottem, J. and Sachs, L. (1979) Proc. Natl. Acad. Sci. (USA) 76: 5158–5162.
19. Terada, M., Epner, E., Nudel, U., Salmon, J., Fibach, E., Rifkind, R. A., and Marks, P. A. (1978) Proc. Natl. Acad. Sci. (USA) 75: 2795–2799.
20. Morin, M. J. and Sartorelli, A. C. (1984) Cancer Res. 44: 2807–2812.
21. Schwartz, E. L., Brown, B. J., Nierenberg, M., Marsh, J. C., and Sartorelli, A. C. (1983) Cancer Res. 43: 2725–2730.
22. Sugano, H., Furusawa, M., Kawaguchi, T., and Ikawa, Y. (1973) Bibl. Hematol. 39: 943–954.
23. Ebert, P. S., Wars, I., and Buell, D. N. (1976) Cancer Res. 36: 1809–1813.
24. Hayashi, M., Okabe, J., and Hozumi, M. (1979) Gann 70: 235–238.
25. Fibach, E., Reuben, R. C., Rifkind, R. A., and Marks, P. A. (1977) Cancer Res. 37: 440–444.
26. Melloni, E., Pontremoli, S., Damiani, G., Viotti, P., Weich, N., Rifkind, R. A., and Marks, P. A. (1988) Proc. Natl. Acad. Sci. (USA) 85: 3835–3839.
27. Reuben, R., Khanna, P. L., Gazitt, Y., Breslow, R., Rifkind, R. A., and Marks, P. A. (1978) J. Biol. Chem. 253: 4214–4218.
28. Marks, P. A. and Rifkind, R. A. (1988) International Journal of Cell Cloning 6: 230–240.

29. Melloni, E., Pontremoli, S., Michetti, M., Sacco, O., Cakiroglu, A. G., Jackson, J. F., Rifkind, R. A., and Marks, P. A. (1987) Proc. Natl. Acad. Sciences (USA) 84: 5282–5286.
30. Marks, P. A. and Rifkind, R. A. (1984) Cancer 54: 2766–2769.
31. Egorin, M. J., Sigman, L. M. VanEcho, D. A., Forrest, A., Whitacre, M. Y., and Aisner, J. (1987) Cancer. Res. 47: 617–623.
32. Rowinsky, E. W., Ettinger, D. S., Grochow, L. B., Brundrett, R. B., Cates, A. E., and Donehower, R. C. (1986) J. Clin. Oncol. 4: 1835–1844.
33. Rowinsky, E. L. Ettinger, D. S., McGuire, W. P., Noe, D. A., Grochow, L. B., and Donehower, R. C. (1987) Cancer Res. 47: 5788–5795.
34. Callery, P. S., Egorin, M. J., Geelhaar, L. A., and Nayer, M. S. B. (1986) Cancer Res. 46: 4900–4903.
35. Young, C. W. Fanucchi, M. P., Walsh, T. B., Blatzer, L., Yaldaie, S., Stevens, Y. W., Gordon, C., Tong, W., Rifkind, R. A., and Marks, P. A. (1988) Cancer Res. 48: 7304–7309.
36. Andreeff, M., Young, C., Clarkson, B., Fetten, J., Rifkind, R. A., and Marks, P. A. (1988) Blood 72: 186a.
37. Marks, P. A., Richon, V. M., Breslow, R., Rifkind, R. A., *Life Sciences* 1999, 322: 161–165.
38. Yoshida et al., 1990, *J. Biol. Chem.* 265:17174–17179.
39. Richon, V. M., Emiliani, S., Verdin, E., Webb, Y., Breslow, R., Rifkind, R. A., and Marks, P. A., Proc. Natl. Acad. Sci. (USA) 95: 3003–3007 (1998).
40. Nishino, N. et. al. *Chem. Pharm. Bull.* 1996, 44, 212–214.
41. U.S. Pat. No. 5,369,108, issued Nov. 29, 1994.
42. Kijima et al., 1993, *J. Biol. Chem.* 268:22429–22435.
43. Lea et al., 1999, *Int. J. Oncol.* 2:347–352.
44. Kim et al., 1999, *Oncogene* 15:2461–2470.
45. Saito et al., 1999, *Proc. Natl. Acad. Sci.* 96:4592–4597.
46. Lea and Tulsyan, 1995, *Anticancer Res.* 15:879–883.
47. Nokajima et al., 1998, *Exp. Cell Res.* 241:126–133.
48. Kwon et al., 1998, *Proc. Natl. Acad. Sci. USA* 95:3356–3361.
49. Richon et al, 1996, *Proc. Natl. Acad. Sci. USA* 93:5705–5708.
50. Kim et al., 1999, *Oncogene* 18:2461–2470.
51. Yoshida et al., 1995, *Bioessays* 17:423–430.
52. Yoshida & Beppu, 1988, *Exp. Cell. Res.* 177:122–131.
53. Warrell et al., 1998, *J. Natl. Cancer Inst.* 90:1621–1625.
54. Desai et al., 1999, *Proc. AACR* 40: abstract #2396.
55. Cohen et al., *Antitumor Res.*, submitted.
56. D. W. Christianson and W. N. Lipscomb, "The Complex Between Carboxypeptidase A and a Possible Transition-State Analogue: Mechanistic Inferences from High-Resolution X-ray Structures of Enzyme-inhibitor Complexes," *J. Am. Chem. Soc.* 1986, 108, 4998–5003.
57. G. H. S. Prakash and A. K. Yudin, "Perfluoroalkylation with Organosilicon Reagents," *Chem. Rev.* 1997, 97, 757–786.
58. J.-C. Blazejewski, E. Anselmi, and M. P. Wilmshurst, "Extending the Scope of Ruppert's Reagent: Trifluoromethylation of Imines," *Tet. Letters* 1999, 40, 5475–5478.
59. R. J. Linderman and D. M. Graves, "Oxidation of Fluoroalkyl-Substituted Carbinols by the Dess-Martin Reagent," *J. Org. Chem.* 1989, 54, 661–668.
60. N. E. Jacobsen and P. A. Bartlett, "A Phosphonamidate Dipeptide Analogue as an Inhibitor of Carboxypeptidase A," *J. Am. Chem. Soc.* 1981, 103, 654–657.
61. S. Lindskog, L. E. Henderson, K. K. Kannan, A. Liljas, P. 0. Nyman, and B. Strandberg, "Carbonic Anhydrase", in *The Enzymes*, 3rd edition, P. D. Boyer, ed., 1971, vol. V, pp. 587–665, see p. 657.
62. Durrant, G.; Greene, R. H.; Lambeth, P. F.; Lester, M. G.; Taylor, N. R., *J. Chem. Soc., Perkin Trans. I* 1983, 2211–2214.
63. Burden, R. S.; Crombie, L., J. Chem. Soc. (C) 1969, 2477–2481.
64. Farquhar, D.; Cherif, A.; Bakina, E.; Nelson, J. A., *J. Med. Chem.*, 1998, 41, 965–972.
65. Boivin, J.; El Kaim, L.; Zard, S. Z., *Tet. Lett.* 1992, 33, 1285–1288.
66. Finnin, M. S. et al., Structures of a histone deacetylase homologue bound to the TSA and SAHA inhibitors. *Nature* 401, 188–93 (1999).
67. Webb, Y. et al., Photoaffinity labeling and mass spectrometry identify ribosomal protein S3 as a potential target for hybrid polar cytodifferentiation agents. *J. Biol. Chem.* 274, 14280–14287 (1997).
68. Butler, L. M. et al., Suberoylanilide hydroxamic acid (SAHA), an inhibitor of histone deacetylase, suppresses the growth of the CWR22 human prostate cancer xenograft. submitted (2000).

What is claimed is:

1. A compound having the formula:

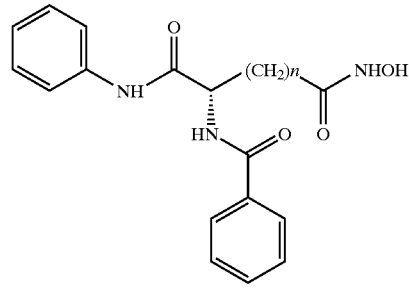

wherein n is an integer from 3 to 10 or an enantiomer or a pharmaceutically acceptable salt thereof.

2. The compound of claim 1, wherein n=5.

3. A compound having the formula:

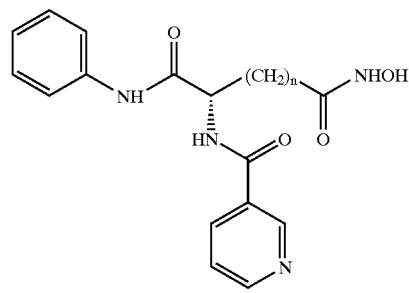

wherein n is an integer from 3 to 10 or an enantiomer or a pharmaceutically acceptable salt thereof.

4. The compound of claim 3, wherein n=5.

5. A compound having the formula:

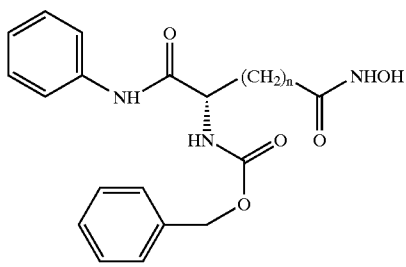

wherein n is an integer from 3 to 10 or an enantiomer or a pharmaceutically acceptable salt thereof.

6. The compound of claim 5, wherein n=5.

7. A compound having the formula:

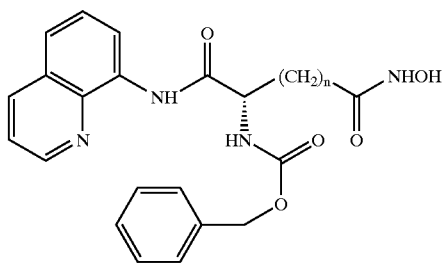

wherein n is an integer from 3 to 10 or an enantiomer or a pharmaceutically acceptable salt thereof.

8. The compound of claim 7, wherein n=5.

9. A compound having the formula:

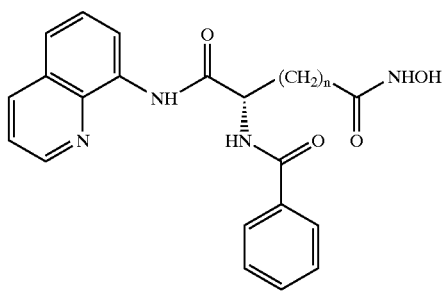

wherein n is an integer from 3 to 10 or an enantiomer or a pharmaceutically acceptable salt thereof.

10. The compound of claim 9, wherein n=5.

11. A compound having the formula:

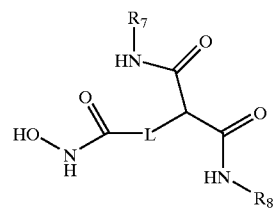

wherein L is a linker selected from the group consisting of —(CH$_2$)—, —(CH=CH)—, -phenyl-, -cycloalkyl-, or any combination thereof; and wherein each of R$_7$ and R$_8$ are independently substituted or unsubstituted, aryl, naphtha, pyridineamino, 9-purine-6-amine, thiazoleamino group, aryloxy, arylalkyloxy, or pyridine group.

12. The compound of claim 11, wherein the linker L is

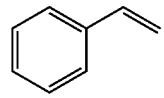

13. A compound having the formula:

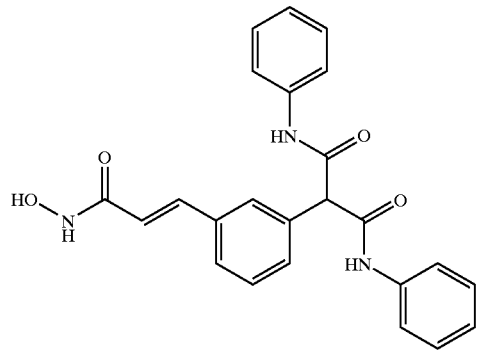

or a pharmaceutically acceptable salt thereof.

14. A compound having the formula:

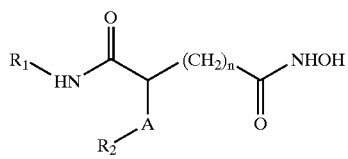

wherein A is an amide moiety, R$_1$ and R$_2$ are each selected from substituted or unsubstituted aryl, naphtha, pyridineamino, 9-purine-6-amine, thiazoleamino, aryloxy, arylalkyloxy or pyridine and n is an integer from 3 to 10 or a pharmaceutically acceptable salt thereof.

15. A compound of claim 14 having the following formula:

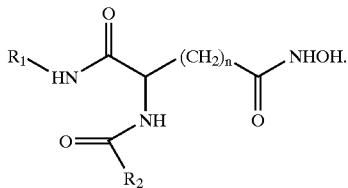

16. A compound of claim 14 having the following formula:

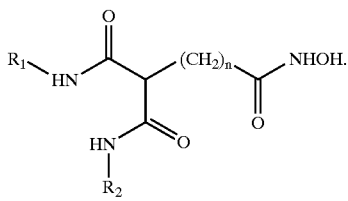

17. A compound having the formula:

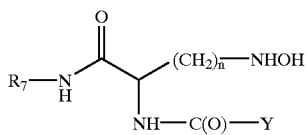

wherein $R_7$ is selected from substituted or unsubstituted aryl, naphtha, pyridineamino, 9-purine-6-amine, thiazoleamino, aryloxy, arylalkyloxy or pyridine and n is an integer from 3 to 10 and Y is selected from

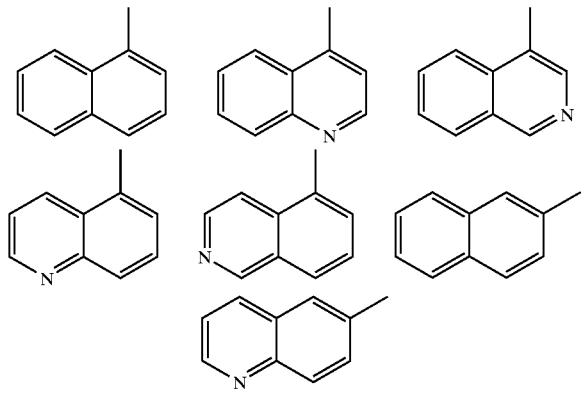

or a pharmaceutically acceptable salt thereof.

18. A compound having the formula:

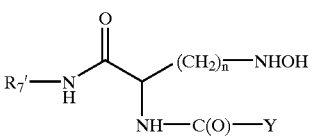

wherein n is an integer from 3 to 10, Y is selected from

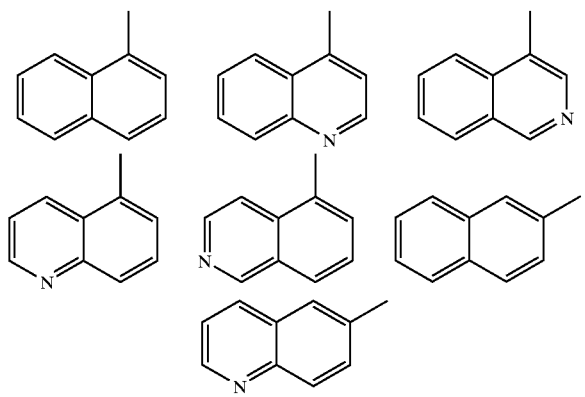

$R_7'$ is selected from

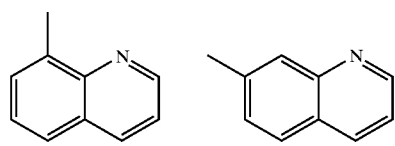

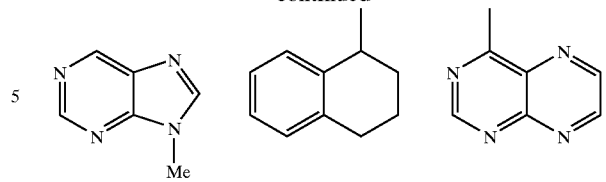

or a pharmaceutically acceptable salt thereof.

19. A compound having the formula:

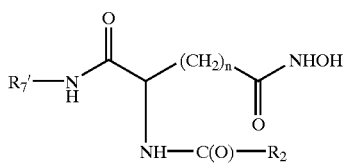

wherein $R_2$ is selected from substituted or unsubstituted aryl, substituted or unsubstituted naphtha, pyridineamino, 9-purine-6-amine, thiazoleamino, substituted or unsubstituted aryloxy, substituted or unsubstituted arylalkyloxy or pyridine and n is an integer from 3 to 10 and $R_7'$ is selected from

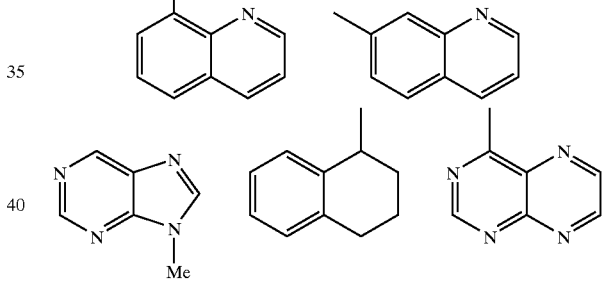

or a pharmaceutically acceptable salt thereof.

20. A compound having the formula:

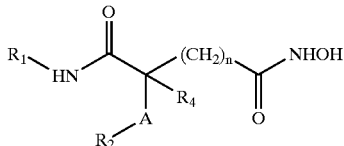

wherein A is an amide moiety, $R_1$ and $R_2$ are each selected from substituted or unsubstituted aryl, naphtha, pyridineamino, 9-purine-6-amine, thiazoleamino, aryloxy, arylalkyloxy or pyridine, $R_4$ is hydrogen, a halogen, a phenyl or a cycloalkyl moiety and n is an integer from 3 to 10 or a pharmaceutically acceptable salt thereof.

21. A compound of claim 20 having the following formula:

22. A compound of claim 20 having the following formula:

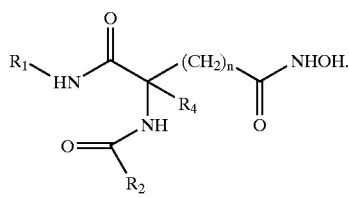

23. A compound having the formula:

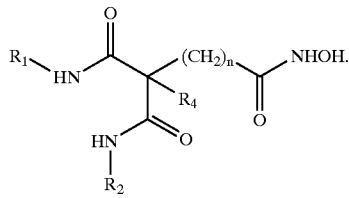

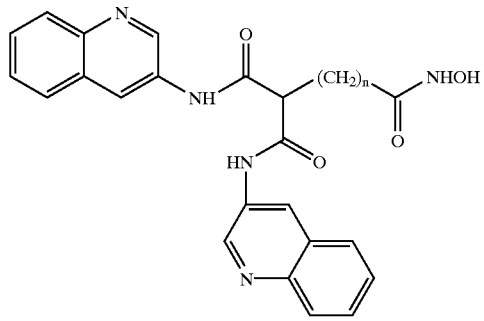

wherein n is an integer from 3 to 10 or a pharmaceutically acceptable salt thereof.

24. A compound of claim 23 wherein n=5.

25. A compound having the formula:

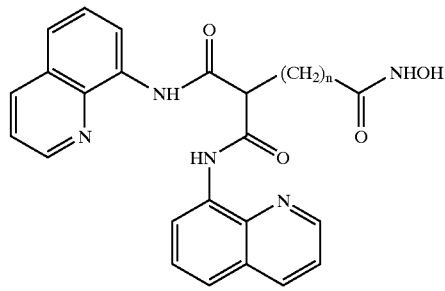

wherein n is an integer from 3 to 10 or a pharmaceutically acceptable salt thereof.

26. A compound of claim 25 wherein n=5.

27. A compound having the formula:

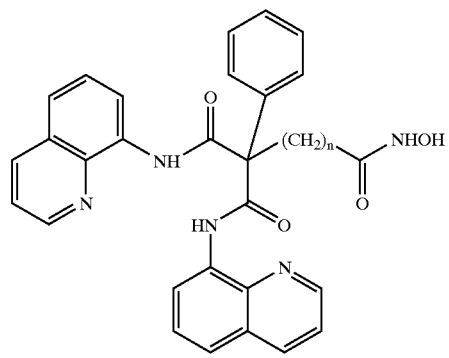

wherein n is an integer from 3 to 10 or a pharmaceutically acceptable salt thereof.

28. A compound of claim 27 wherein n=5.

29. A compound having the formula:

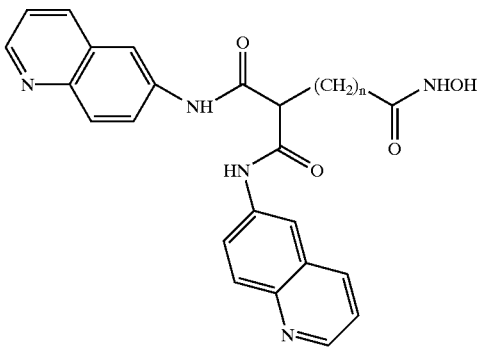

wherein n is an integer from 3 to 7 or a pharmaceutically acceptable salt thereof.

30. A compound of claim 29 wherein n=5.

31. A compound having the formula:

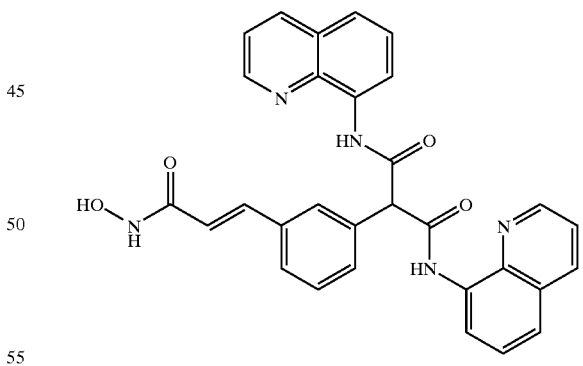

or a pharmaceutically acceptable salt thereof.

32. A pharmaceutical composition comprising a pharmaceutically effective amount of the compound of any one of claims 1, 2, 3, 4, 5, 6, 7, 8, 9, 10, 11, 12, 13, or 14–31 and a pharmaceutically acceptable carrier.

33. A method of selectively inducing terminal differentiation of neoplastic cells and thereby inhibiting proliferation of such cells which comprises contacting the cells under suitable conditions with an effective amount of the compound of any one of claims 1, 2, 3, 4, 5, 6, 7, 8, 9, 10, 11, 12, 13, or 14–31.

34. A method of inducing differentiation of tumor cells in a tumor comprising contacting the cells with an effective amount of the compound of any one of claims 1, 2, 3, 4, 5, 6, 7, 8, 9, 10, 11, 12, 13, or 14–31.

35. A method of inhibiting the activity of histone deacetylase comprising contacting the histone deacetylase with an effective amount of the compound of any one of claims 1, 2, 3, 4, 5, 6, 7, 8, 9, 10, 11, 12, 13, or 14–31 so as to thereby inhibit the activity of histone deacetylase.

* * * * *

UNITED STATES PATENT AND TRADEMARK OFFICE
CERTIFICATE OF CORRECTION

PATENT NO.   : 6,511,990 B1
DATED        : January 28, 2003
INVENTOR(S)  : Breslow et al.

It is certified that error appears in the above-identified patent and that said Letters Patent is hereby corrected as shown below:

Column 49,
Table 2, delete the chemical structure shown for compound 654

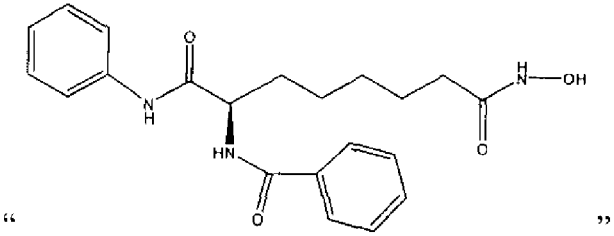

and insert the following chemical structure:

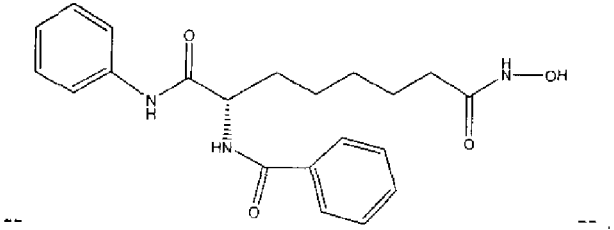

Column 51,
Table 2, delete the chemical structure shown for compound 656

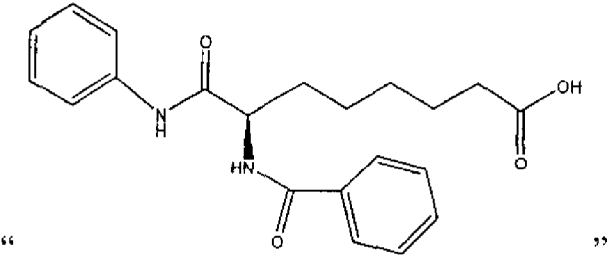

and insert the following chemical structure:

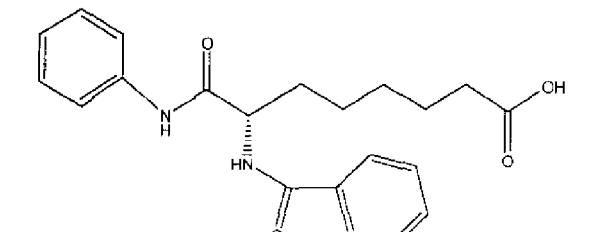

UNITED STATES PATENT AND TRADEMARK OFFICE
CERTIFICATE OF CORRECTION

PATENT NO.    : 6,511,990 B1
DATED         : January 28, 2003
INVENTOR(S)   : Breslow et al.

It is certified that error appears in the above-identified patent and that said Letters Patent is hereby corrected as shown below:

Column 51 (cont'd),
Table 2, delete the chemical structure shown for compound 657

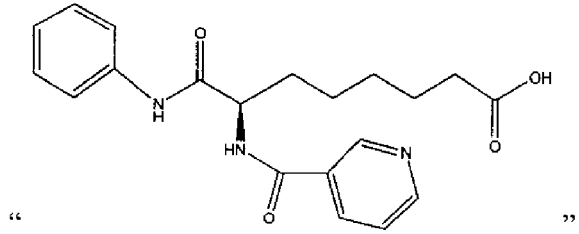

and insert the following chemical structure:

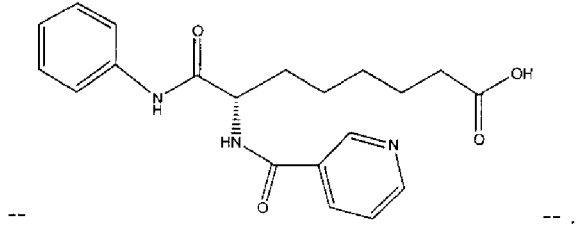

Column 53,
Table 2, delete the chemical structure shown for compound 660

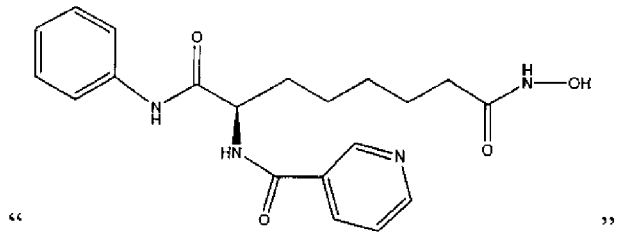

and insert the following chemical structure:

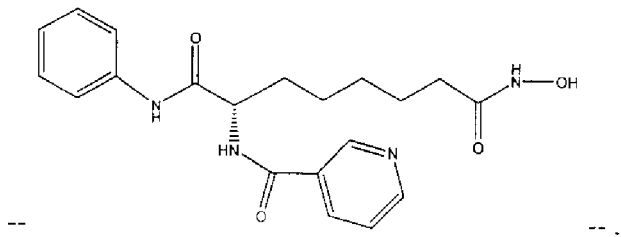

UNITED STATES PATENT AND TRADEMARK OFFICE
CERTIFICATE OF CORRECTION

PATENT NO.    : 6,511,990 B1                                           Page 3 of 4
DATED         : January 28, 2003
INVENTOR(S)   : Breslow et al.

It is certified that error appears in the above-identified patent and that said Letters Patent is hereby corrected as shown below:

Column 53 (cont'd),
Table 2, delete the chemical structure shown for compound 661

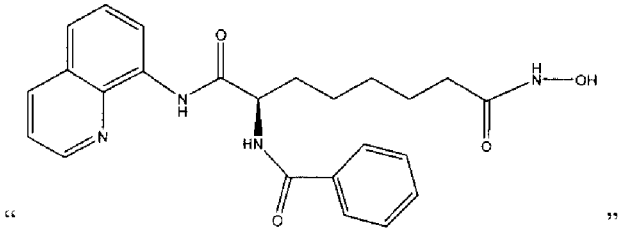

" "

and insert the following chemical structure:

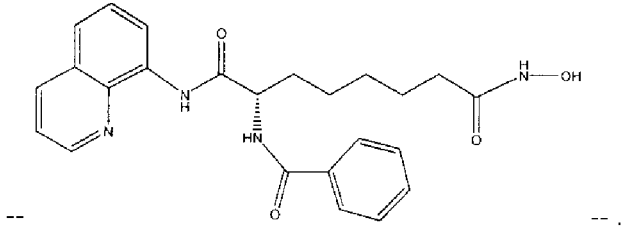

-- -- .

UNITED STATES PATENT AND TRADEMARK OFFICE
CERTIFICATE OF CORRECTION

PATENT NO. : 6,511,990 B1
DATED : January 28, 2003
INVENTOR(S) : Breslow et al.

It is certified that error appears in the above-identified patent and that said Letters Patent is hereby corrected as shown below:

Column 53 (cont'd),
Table 2, delete the chemical structure shown for compound 663

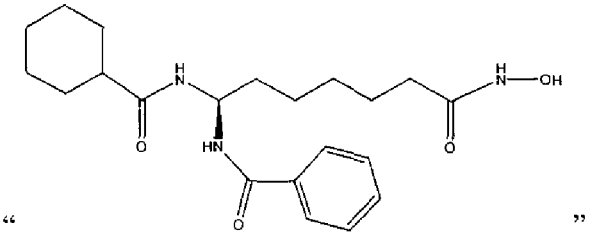

" "

and insert the following chemical structure:

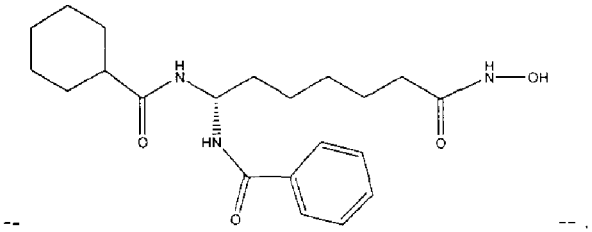

-- -- .

Signed and Sealed this

Twenty-eighth Day of June, 2005

JON W. DUDAS
*Director of the United States Patent and Trademark Office*